US011534467B2

(12) United States Patent
Duportet et al.

(10) Patent No.: US 11,534,467 B2
(45) Date of Patent: *Dec. 27, 2022

(54) MODULATION OF MICROBIOTA FUNCTION BY GENE THERAPY OF THE MICROBIOME TO PREVENT, TREAT OR CURE MICROBIOME-ASSOCIATED DISEASES OR DISORDERS

(71) Applicant: Eligo Bioscience, Paris (FR)

(72) Inventors: Xavier Duportet, Paris (FR); Antoine Decrulle, Paris (FR); Cristina Del Carmen Gil-Cruz, St. Gallen (CH); Christian Ivan Pérez-Shibayama, St. Gallen (CH); Burkhard Ludewig, St. Gallen (CH); Jesus Fernandez Rodriguez, Paris (FR); Andreas Brodel, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/716,313

(22) Filed: Apr. 8, 2022

(65) Prior Publication Data

US 2022/0233610 A1    Jul. 28, 2022

Related U.S. Application Data

(63) Continuation of application No. 17/501,110, filed on Oct. 14, 2021, which is a continuation of application No. 17/225,869, filed on Apr. 8, 2021, now Pat. No. 11,224,621.

(60) Provisional application No. 63/137,998, filed on Jan. 15, 2021, provisional application No. 63/137,989, filed on Jan. 15, 2021, provisional application No. 63/132,190, filed on Dec. 30, 2020, provisional application No. 63/007,191, filed on Apr. 8, 2020.

(51) Int. Cl.
C12N 15/74 (2006.01)
A61K 35/74 (2015.01)
C12N 15/70 (2006.01)
C12N 15/90 (2006.01)

(52) U.S. Cl.
CPC .............. *A61K 35/74* (2013.01); *C12N 15/70* (2013.01); *C12N 15/74* (2013.01); *C12N 15/902* (2013.01)

(58) Field of Classification Search
CPC ........... C12N 9/22; C12N 15/74; A61K 35/74
See application file for complete search history.

(56) References Cited

U.S. PATENT DOCUMENTS

| 5,863,560 A | 1/1999 | Osborne |
| 7,482,115 B2 | 1/2009 | Scott et al. |
| 11,224,621 B2 | 1/2022 | Duportet et al. |
| 2011/0218216 A1 | 9/2011 | Vivek et al. |
| 2015/0064138 A1 | 3/2015 | Lu et al. |
| 2020/0248192 A1* | 8/2020 | Decrulle .............. C12N 15/74 |

FOREIGN PATENT DOCUMENTS

| WO | 2014124226 A1 | 8/2014 |
| WO | WO2017009399 A1 | 1/2019 |
| WO | WO2020181178 A1 | 9/2020 |
| WO | WO2020181180 A1 | 9/2020 |
| WO | WO2020181193 A1 | 9/2020 |
| WO | WO2020181195 A1 | 9/2020 |
| WO | WO2020181202 A1 | 9/2020 |

OTHER PUBLICATIONS

Abudayyeh ey al., RNA targeting with CRISPR-Cas13a, Nature. Oct. 12, 2017; 550(7675): 280-284.
Anne et al., Protein Secretion in Gram-Positive Bacteria: From Multiple Pathways to Biotechnology, Springer International Publishing Switzerland 2016, Current Topics in Microbiology and Immunology, 1-42.
Anzalone et al., Search-and-replace genome editing without double-strand breaks or donor DNA, Nature. Dec. 2019 ; 576(7785): 149-157.
Camprubi-Font et al., Genetic and Phenotypic Features to Screen for Putative Adherent-Invasive *Escherichia coli*. Frontiers in Microbiology, Feb. 21, 2019, vol. 10, Article 108, 1-11.
Camprubi-Font et al., Amino Acid Substitutions and Differential Gene Expression of Outer Membrane Proteins in Adherent-Invasive *Escherichia coli*, Frontiers in Microbiology, Aug. 6, 2019, vol. 10, Article 1707, 1-10.
Chen et al., Precise and programmable C:G to G:C base editing in genomic DNA, bioRxiv preprint doi: https://doi.org/10.1101/2020.07.21.213827; this version posted Jul. 21, 2020, 1-19.
Chen et al., Programmable C:G to G:C genome editing with CRISPR-Cas9-directed base excision repair proteins, Nature Communications | (2021) 12:1384 | https://doi.org/10.1038/s41467-021-21559-9 | www.nature.com/naturecommunications, 1-7.

(Continued)

*Primary Examiner* — Karen Cochrane Carlson
(74) *Attorney, Agent, or Firm* — Arrigo, Lee, Guttman & Mouta-Bellum, LLP

(57) ABSTRACT

The invention encompasses compositions, kits and methods for modifying bacteria, preferably naturally occurring bacteria, in situ. These can be used to treat, prevent or cure microbiome-associated diseases or disorders by modulating the molecules expressed and/or secreted by bacterial populations of the microbiome in a specific manner. The genomic modifications can modify the interactions between part or all of these populations and the host in a way that decreases their deleterious potential on host health. The compositions, kits and methods of the invention do not result in the direct death of these populations or a direct significant inhibition of their growth. The invention further includes methods for screening for genetic modifications in the bacteria, for determining the efficiency of vectors at inducing these genetic mutations, and for determining the effects of these mutations on bacterial growth.

23 Claims, 14 Drawing Sheets

Specification includes a Sequence Listing.

(56) References Cited

OTHER PUBLICATIONS

Costa et al., Secretion systems in Gram-negative bacteria: structural and mechanistic insights, Nature Reviews | Microbiology vol. 13 | Jun. 2015 | 343-359.
Cox et al., RNA Editing with CRISPR-Cas13, Science. Nov. 24, 2017; 358(6366): 1019-1027.
Del Solar et al., Replication and Control of Circular Bacterial Plasmids, Microbiology and Molecular Biology Reviews, vol. 62, No. 2 Jun. 1998, p. 434-464.
Dreux et al., Point Mutations in FimH Adhesin of Crohn's Disease-Associated Adherent-Invasive *Escherichia coli* Enhance Intestinal Inflammatory Response, PLoS Pathog 9(1): e1003141, 1-17, Published Jan. 24, 2013.
Farzadfard et al., Genomically Encoded Analog Memory with Precise In vivo DNA Writing in Living Cell Populations, Science. Nov. 14, 2014; 346(6211), 1-18.
Fillol-Salom et al., Phage-inducible chromosomal islands are ubiquitous within the bacterial universe, The ISME Journal (2018) 12:2114-2128.
Fonfara et al., Phylogeny of Cas9 determines functional exchangeability of dual-RNA and Cas9 among orthologous type II CRISPR-Cas systems, Nucleic Acids Research, 2014, vol. 42, No. 4 2577-2590.
Garcia et al., Peripheral tolerance to insulin is encoded by mimicry in the microbiome, bioRxiv preprint first posted online Dec. 19, 2019; doi: http://dx.doi org/10.1101/2019.12.18.881433, 1-14.
Guadelli et al., Programmable base editing of A•T to G•C in genomic DNA without DNA cleavage, Nature. Nov. 23, 2017; 551(7681): 464-471.
Gil-Cruz et al., Microbiota-derived peptide mimics drive lethal inflammatory cardiomyopathy, Science 366, 881-886 (2019).
Greiling et al., Commensal orthologs of the human autoantigen Ro60 as triggers of autoimmunity in lupus, Sci Transl Med. Mar. 28, 2018; 10(434), 1-33.
Grunewald et al., A dual-deaminase CRISPR base editor enables concurrent adenine and cytosine editing, Nat Biotechnol. Jul. 2020 ; 38(7): 861-864.
Henkel et al., Toxins from Bacteria, EXS. 2010 ; 100: 1-29.
Jinek et al., A programmable dual RNA-guided DNA endonuclease in adaptive bacterial immunity, Science. Aug. 17, 2012; 337(6096): 816-821.
Karberg et al., Group II introns as controllable gene targeting vectors for genetic amnipulation of bacteria, Nature Biotechnology, vol. 19, Dec. 2001, 1162-1167.
Komor et al., Programmable editing of a target base in genomic DNA without double-stranded DNA cleavage, Nature. ; 533(7603): 420-424, available in PMC Oct. 20, 2016.
Koonin et al., Diversity, classification and evolution of CRISPR-Cas systems, Curr Opin Microbiol. Jun. 2017 ; 37: 37-78.
Krupovik et al., A classification system for virophages and satellite viruses, Arch Virol (2016) 161:233-247.
Kues et al., Replication of Plasmids in Gram-Negative Bacteria, Microbiological Reviews, Dec. 1989, vol. 53, No. 4, p. 491-516.
Kurt et al., CRISPR C-to-G base editors for inducing targeted DNA transversions in human cells, Nat Biotechnol. Jan. 2021 ; 39(1): 41-46.
Li et al., Targeted, random mutagenesis of plant genes with dual cytosine and adenine base editors, Nature Biotechnology vol. 38, pp. 875-882 (2020).
Maini Rekdal et al., Discovery and inhibition of an interspecies gut bacterial pathway for Levodopa metabolism, Science 364, 1055 (2019) Jun. 14, 2019, 1-11.
Makarova et al., Evolutionary classification of CRISPR-Cas systems: a burst o, f class 2 and derived variants, Nature Reviews Microbiology vol. 18, pp. 67-83 (2020).
Massip et al., Deciphering the interplay between the genotoxic and probiotic activities of *Escherichia coli* Nissle 1917, PLoS Pathog 15(9): e1008029, 1-24, Published: Sep. 23, 2019.
Meric et al., Disease-associated genotypes of the commensal skin bacterium *Staphylococcus epidermidis*, Nature Communications, (2018) 9:5034, 1-11.
Myers et al., Optimal alignments in linear space, CABIOS, vol. 4, No. 1. 1988, pp. 11-17.
Needleman et al., A General Method Applicable to the Search for Similarities in the Amino Acid Sequence of Two Proteins, J. Mol. Biol. (1970) 48, 443-453.
Negi et al., Gut bacterial peptides with autoimmunity potential as environmental trigger for late onset complex diseases: In-silico study, PLoS One 12(7): e0180518, Published Jul. 5, 2017.
Rees et al., Base editing: precision chemistry on the genome and transcriptome of living cells, Nat Rev Genet. Dec. 2018 ; 19(12): 770-788.
Ruff et al., Pathogenic Autoreactive T and B Cells Cross-React with Mimotopes Expressed by a Common Human Gut Commensal to Trigger Autoimmunity, Cell Host & Microbe 26, 100-113, Jul. 10, 2019.
Sharon et al., Functional genetic variants revealed by massively parallel precise genome editing, Cell. Oct. 4, 2018; 175(2): 544-557.
Simon et al., Retrons and their applications in genome engineering, Nucleic Acids Research, 2019, vol. 47, No. 21 11007-11019, Published online Oct. 10, 2019.
Tam et al., *Staphylococcus aureus* Secreted Toxins & Extracellular Enzymes, Microbiol Spectr. Mar. 2019 ; 7(2):1-59.
Tomida et al., Pan-Genome and Comparative Genome Analyses of Propionibacterium acnes Reveal Its Genomic Diversity in the Healthy and Diseased Human Skin Microbiome, mBio 4(3):e00003-13. doi:10.1128/mBio.00003-13, May/Jun. 2013.
Wang et al., Lysis Timing and Bacteriophage Fitness, Genetics 172: 17-26 ( Jan. 2006).
Wannier et al., Improved bacterial recombineering by parallelized protein discovery, bioRxiv preprint doi: https://doi.org/10.1101/2020.01.14.906594, uploaded on Feb. 26, 2020.
Weigele et al., Biosynthesis and Function of Modified Bases in Bacteria and Their Viruses, Chem. Rev. 2016, 116, 12655-12687, Published: Jun. 20, 2016.
Yan et al., Cas13d is a compact RNA-targeting type VI CRISPR effector positively modulated by a WYL domain-containing accessory protein. Mol Cell. Apr. 19, 2018; 70(2): 327-339.
Zhao et al., New base editors change C to A in bacteria and C to G in mammalian cells, Nature Biotechnology vol. 39, pp. 35-40 (2021).
Zimmerman et al., Mapping human microbiome drug metabolism by gut bacteria and their genes, Nature. Jun. 2019 ; 570(7762): 462-467.
Zou et al., A SNP of bacterial blc disturbs gut lysophospholipid homeostasis and induces inflammation through epithelial barrier disruption, EBioMedicine 52(2020)102652, 1-17.
Bikard et al., Exploiting CRISPR-Cas nucleases to produce sequence-specific antimicrobials, Nature Biotechnology, vol. 32, No. 11, 1146-51, Nov. 2014.
Brezgin et al., Dead CasSystems: Types, Principles, and Applications, INternational Journal of Molecular Sciences 2019, 20, 6041, 1-26, Nov. 30, 2019.
Cobb et al., CRISPR-Cas9 modified bacteriophage for treatment of *Staphylococcus aureus* induced osteomyelitis and soft tissue infection, PLOS One14(11):e0220421, 1-17, Nov. 22, 2019.
Huss et al.,Engineered bacteriophages as programmable biocontrol agents, Current Opinion in Biotechnology 2020, 61, 115-121, Dec. 17, 2019.
Lam et al.,Phage-delivered CRISPR-Cas9 for strain-specific depletion and genomic deletions in the gut microbiota, bioRxiv, doi.org/10.1101/2020.07.09.193847, 1-60, Jul. 9, 2020.
Park et al., Genetic engineering of a temperate phage-based delivery system for CRISPR/Cas9 antimicrobials ahgainst *Staphylococcus aureus*, Scientific Reports 7:44929, 1-12, Mar. 21, 2017.
European Patent Offfice, International Search Report, PCT/EP2021/059229, dated Jul. 19, 2021.
Jiang et al. 2013; RNA-guided editing of bacterial genomes using CRISPR-Cas systems. Nature Biotechnology. 31 (3): 233-239, plus 2 pages of Online Methods.
Sheth et al. 2017; Manipulating bacterial communities by in situ microbiome engineering. Tends Genet. 32(4): 189-200.

(56) References Cited

OTHER PUBLICATIONS

Voorhees et al. 2020; Challenges & opportunities for phage-based in situ microbiome engineering in the gut. Journal of Controlled Release.326: 106-119.
Ramachandran et al. 2019; Editing the microbiome the CRIS PR way. Phil. Trans. R. Soc. B 374:20180103; pp. 1-10.
Guadelli et al. 2017; Programmable base editing of A-T to G-C in genomic DNA without DNA cleavage. Nature. 551:464-490.
Komar et al. 2016; Programmable editing of a target base in genomic DNA without double-strand DNA cleavage. Nature. 533:420-436.
Nishida et al. 2016; Targeted nucleotide editing using hybrid prokaryotic and vertebrate adaptive immune systems. Science. 353: aaf8729-1-aaf8729-8.
Tong et al. 2019; Highly efficient DSB-free base editing for streptomycetes with CRISPR-BEST. PNAS. 116(41): 20366-20375.

\* cited by examiner

MODULATION OF MICROBIOTA FUNCTION BY GENE THERAPY OF THE MICROBIOME TO PREVENT, TREAT OR CURE MICROBIOME-ASSOCIATED DISEASES OR DISORDERS

CROSS REFERENCE TO RELATED APPLICATIONS

This application is a continuation of U.S. application Ser. No. 17/501,110, filed Oct. 14, 2021, which is a continuation of U.S. application Ser. No. 17/225,869, filed Apr. 8, 2021, now U.S. Pat. No. 11,224,621, which claims the benefit of U.S. application 63/007,191 filed Apr. 8, 2020, U.S. application 63/132,190 filed Dec. 30, 2020, U.S. application 63/137,998 filed Jan. 15, 2021, and U.S. application 63/137,989 of Jan. 15, 2021, all of which are herein incorporated by reference in their entirety.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Apr. 8, 2022, is named EB2020-02_US-reg_Sequence_listing.txt and is 629,761 bytes in size.

TECHNICAL FIELD

The present invention relates to compositions, kits and methods for modifying bacteria, preferably naturally occurring bacteria, in situ.

BACKGROUND OF THE INVENTION

The human microbiota comprises bacteria, archaea, viruses, and microbial eukaryotes living in our bodies. The taxonomic composition of these communities has been extensively studied and is significantly associated with a variety of diseases and traits. This microbiota indeed consists of thousands of different bacterial species that carry hundreds of billions of genes, which is called the microbiome. This microbiome encodes for a variety of molecules (proteins, lipids, sugars, RNA, etc.) and functions that are essential and beneficial for their host, for instance the enrichment of glycans metabolism, amino acids and xenobiotics but also the regulation of our immune system. It is also responsible for the synthesis of vitamins, isoprenoids and other nutrients which results in human overall metabolism representing an amalgamation of microbial and human attributes.

Widespread deployment of sequencing technologies has revealed that most bacterial species harbor extensive genetic variation not only between hosts, but often within a host over time, and even within a host at a given time.

Isolation and sequencing of numerous strains highlight the genetic heterogeneity within a single bacterial species. Between different strains within a single bacterial species, this variation comprises single-nucleotide variants, short insertions and deletions (indels), and larger structural variants, which include duplications, deletions, insertions, inversions but also horizontal gene transfer such as prophage or plasmid acquisition and recombination events with such exogenous DNA.

Due to such variations, such strains, when co-existing in a single host, often compete with each other for their existence in a specific microbiome niche.

Interestingly, there is a growing body of recent studies based on metagenome sequencing that demonstrate that the presence of specific strains (and therefore of specific genetic signatures in the microbiome) can be directly linked to a number of pathologies, including autoimmunity, infections, inflammation, neurodegenerative diseases or tumorigenesis.

To treat microbiome-associated diseases or disorders, current approaches try to remove unwanted bacteria (and therefore the deleterious genes they carry) by using subtractive methods such as antibiotics, replicative phages, lysins, which result in the killing of deleterious bacteria but also non-deleterious bacteria.

While such strategies have proven to be beneficial on the short term by significantly reducing the load of entire bacterial populations, it can both:

induce a strong dysbiosis and indirectly lead to the short-term overgrowth of non-targeted deleterious bacterial species or strains. For example, bacteria such as *Clostridium difficile* are known to fill the bacterial void created by antibiotic treatment. Thus, the killing of a particular targeted species or strain of bacteria within the microbiome can create a void that can be filled by harmful bacteria both in the short-term and in the long term. These bacteria can be of the same or a different species as the targeted species.

lead to the emergence of antimicrobial resistance in the long term and therefore become inefficient in excluding the species or strain(s) carrying the genetic elements associated with the pathology. For example, antibiotic use has been associated with the replacement of antibiotic-sensitive strains of *Staphylococcus aureus* with antibiotic-resistant strains of *Staphylococcus aureus*. Therefore, The durable elimination of an engrafted bacterial population in the microbiome can be challenging to achieve, as the microbiome is naturally in a state of equilibrium with different populations (strain or species) occupying different geographic and metabolic niches. A non-specific treatment like an antibiotic typically leads to a return to the equilibrium that existed before treatment after a few weeks or months. On occasion, the equilibrium will be perturbed for longer periods of time and a dysbiosis can occur. A targeted elimination of a population by phage therapy (wild-type phages to engineered phages, packaged phagemids), lysins, antimicrobial peptides, or any other targeted killing approaches can be equally challenging as targeted bacterial survivors will tend to quickly regrow to occupy the niche that was left empty.

The durable elimination of a bacterial population in the microbiome can be challenging to achieve, as the microbiome is naturally in a state of equilibrium with different populations (strain or species) occupying different geographic and metabolic niches. A non-specific treatment like an antibiotic typically leads to a return to the equilibrium that existed before treatment after a few weeks or months. On occasion, the equilibrium will be perturbed for longer periods of time and a dysbiosis can occur. A targeted elimination of a population by phage therapy (wild-type phages to engineered phages, packaged phagemids), lysins, antimicrobial peptides, or any other targeted killing approaches can be equally challenging as targeted bacterial survivors will tend to quickly regrow to occupy the niche that was left empty.

For these reasons, the genetic modification of a target bacterial population in-situ whether at the strain or species level, can be an interesting alternative. It can lead to the modification of a deleterious population to remove its deleterious effect without killing the target bacteria, and in some cases even without affecting its fitness therefore not disturbing the equilibrium of the ecosystem.

In this way, no void would be created that could be filled by harmful bacteria nor would it lead to treatment resistance. Such an approach would represent a very powerful and elegant approach to treat, prevent or cure a number of microbiome-associated diseases or disorders, especially in the case of long term or chronic pathologies. The invention fulfills this need.

BRIEF SUMMARY OF INVENTION

The invention relates to methods, kits and compositions for modifying a naturally occurring bacteria in situ. In one embodiment, the method, in particular the non-therapeutic method, comprises genetically modifying a DNA sequence in the naturally occurring bacteria in situ without introducing a double strand break in the DNA sequence. Preferably, the genetic modification does not lead to the death of bacteria.

In one embodiment, the method, in particular the non-therapeutic method, comprises contacting said naturally occurring bacteria with a vector encoding enzymes or systems for inducing genetic modifications. The invention also concerns a vector encoding enzymes or systems for inducing genetic modifications, for use in a therapeutic method of modifying a naturally occurring bacteria in situ and/or in vivo.

In one embodiment, said vector further comprises a conditional origin of replication which is inactive in the targeted bacteria but is active in a donor bacterial cell. In a particular embodiment, said conditional origin of replication is an origin of replication, the replication of which depends upon the presence of a given protein, peptid, nucleic acid, RNA, molecule or any combination thereof. In a particular embodiment, said conditional origin of replication is active in said donor bacterial cell because said donor bacterial cell expresses said given protein, peptid, nucleic acid, RNA, molecule or any combination thereof. In a particular embodiment, said conditional origin of replication is an origin of replication derived from phage-inducible chromosomal islands (PICIs). In a particular embodiment, said conditional origin of replication is active in said donor bacterial cell because said donor bacterial cell expresses a rep protein, in particular a primase-helicase. In a particular embodiment, said conditional origin of replication is derived from the origin of replication from the PICI of the *Escherichia coli* strain CFT073. In a particular embodiment, said conditional origin of replication comprises or consists of the sequence SEQ ID NO: 7 or SEQ ID NO: 8.

In one embodiment, said vector is devoid of an antibiotic resistance marker.

In one embodiment, said vector is located inside a delivery vehicle that allows the transfer of the vector into bacteria, more particularly inside a bacterial virus particle. In one embodiment, the method comprises contacting said naturally occurring bacteria with a vector located inside a delivery vehicle that allows the transfer of the vector into bacteria. Preferably, the vector located inside a delivery vehicle is a phagemid and, preferably, the delivery vehicle is a bacterial virus particle or a capsid.

In a particular embodiment, said vector is inside a bacterial virus particle, more particularly is in the form of a packaged phagemid. In one embodiment, the method comprises transducing said naturally occurring bacteria with a packaged phagemid. Preferably, the phagemid comprises a nucleic acid sequence encoding a modified nuclease that is modified to be unable to perform DNA double strand break while retaining its DNA binding capacity and that is fused to a domain to perform other types of function, such as for instance a domain to perform base editing. Preferably, the phagemid comprises a nucleic acid sequence encoding a nuclease that is an RNA guided nuclease. Preferably, the phagemid comprises a nucleic acid sequence encoding a dCas9 (dead-Cas9) or nCas9 (nickase Cas9). In one embodiment, the phagemid comprises a nucleic acid sequence encoding a dCas9 and a deaminase domain, or a nCas9 and a deaminase domain.

In one embodiment, the genetic modification is at least one point mutation(s).

In one embodiment, the genetic modification is at least one insertion or at least one deletion.

In one embodiment, the genetic modification is at least one point mutation(s), insertion and/or deletion inside a coding sequence leading to a frameshift mutation.

In one embodiment, the bacteria with the genetic modification does not have a reduced in vivo growth rate and/or fitness as compared to the same bacteria without the genetic modification.

In one embodiment, the genetic modification is in a bacterial toxin gene. In one embodiment, the genetic modification is in the ClbP gene in pks+ *E. coli* and results in a single amino acid mutation and the inactivation of the genotoxic activity of Colibactin toxin, but maintains the antagonistic activity. Preferably, the genetic modification is at S95 or K98 of the ClbP gene. More preferably, the genetic modification is selected from the group consisting of S95A, S95R and K98T[1].

In one embodiment, the genetic modification is in the *Bacteroides faecis* or *Bacteroides thetaiotaomicron* beta-galactosidase gene, said beta-galactosidase gene being typically of sequence SEQ ID NO: 2322, and typically encoding a protein of sequence SEQ ID NO: 2323. Preferably, the *Bacteroides faecis* or *Bacteroides thetaiotaomicron* beta-galactosidase protein with the genetic modification shows lower homology with human MYH6 cardiac peptide, said human MYH6 cardiac peptide being typically of sequence SEQ ID NO: 2324, as compared to the *Bacteroides faecis* or *Bacteroides thetaiotaomicron* beta-galactosidase protein without the genetic modification[2].

In one embodiment, the method comprises genetically modifying at least one DNA sequence or gene in the naturally occurring bacteria in situ in a subject, in particular in a human. In one embodiment, the method comprises modulating host—microbiome interaction by genetically modifying naturally occurring bacteria in situ wherein said naturally occurring bacteria is involved in microbiome associated disorder or disease.

In one embodiment, the method comprises genetically modifying a DNA sequence responsible for a microbiome associated disorder or disease in the naturally occurring bacteria in situ without introducing a double strand break in the DNA sequence. In one embodiment, the genetic modification reduces the effects of the microbiome associated disorder or disease, and the genetic modification does not lead to the death of bacteria. Preferably, the bacteria with the genetic modification does not have a reduced in vivo growth rate as compared to the same bacteria without the genetic modification.

In one embodiment, the method is to prevent or intervene in the course of an auto-immune disease or reaction in a predisposed host by modifying the immunogenic profile of a bacterial population of the host microbiome. In one embodiment, the method comprises contacting the bacterial population with a vector that generates a genetic modification in a DNA sequence coding for an immunogenic component expressed or secreted by the bacteria in at least some of the bacteria of said population without cleaving the DNA sequence. The invention also concerns a vector generating a genetic modification in a DNA sequence coding for an immunogenic component expressed or secreted by bacteria in at least some of the bacteria of a bacterial population of a host microbiome without cleaving the DNA sequence, for use to prevent or intervene in the course of an auto-immune disease or reaction in a predisposed host, wherein said vector modifies the immunogenic profile of said bacterial population. Preferably, the genetic modification of the DNA sequence coding for the immunogenic component results in loss of the immunogenic effect of said immunogenic component, wherein said genetic modification does not lead to the direct death of the bacteria. Preferably, the genetic modification of the DNA sequence coding for the immunogenic component results in the inability of the immune system to recognize the immunogenic component. Preferably, the bacteria with the genetic modification does not have a reduced in vivo growth rate as compared to the same bacteria without the genetic modification.

In one embodiment, the method comprises contacting said naturally occurring bacteria with a vector encoding enzymes or systems for inducing genetic modifications.

In one embodiment, said vector further comprises a conditional origin of replication which is inactive in the targeted bacteria but is active in a donor bacterial cell. In a particular embodiment, said conditional origin of replication is an origin of replication, the replication of which depends upon the presence of a given protein, peptid, nucleic acid, RNA, molecule or any combination thereof. In a particular embodiment, said conditional origin of replication is active in said donor bacterial cell because said donor bacterial cell expresses said given protein, peptid, nucleic acid, RNA, molecule or any combination thereof. In a particular embodiment, said conditional origin of replication is an origin of replication derived from phage-inducible chromosomal islands (PICIs). In a particular embodiment, said conditional origin of replication is active in said donor bacterial cell because said donor bacterial cell expresses a rep protein, in particular a primase-helicase. In a particular embodiment, said conditional origin of replication is derived from the origin of replication from the PICI of the *Escherichia coli* strain CFT073. In a particular embodiment, said conditional origin of replication comprises or consists of the sequence SEQ ID NO: 7 or SEQ ID NO: 8.

In one embodiment, said vector is devoid of an antibiotic resistance marker.

In one other embodiment, said vector comprises an auxotrophic marker.

In one embodiment, said vector is located inside a delivery vehicle that allows the transfer of the vector into bacteria, more particularly inside a bacterial virus particle.

In one embodiment, the method comprises contacting said naturally occurring bacteria with a vector located inside a delivery vehicle that allows the transfer of the vector into bacteria.

Preferably, the delivery vehicle with the vector is a packaged phagemid.

In a particular embodiment, said packaged phagemid comprises a phagemid encoding an enzyme that modifies the genome of said bacterial. Preferably, said enzyme is a base editor or a prime editor.

In one embodiment, the method comprises transducing said bacteria with a packaged phagemid comprising a phagemid encoding an enzyme that modifies the genome of said bacteria. Preferably, the method comprises transducing said bacteria with a packaged phagemid comprising a phagemid encoding an enzyme that is a base editor. Preferably, the method comprises transducing said bacteria with a packaged phagemid comprising a phagemid encoding an enzyme that is a prime editor.

In one embodiment, the modification is at least one point mutation(s) in a protein-encoding nucleic acid sequence that results in a change of amino acid in a mimic peptide and renders the mimic peptide not immunogenic i.e. not recognized by the immune system.

In one other embodiment, the genetic modification results in a change of sugar profile on the bacterial membrane.

In one other embodiment, the genetic modification results in a change of amino acid in a protein sequence that in turn results in a change of sugar profile on the bacterial membrane In one other embodiment, the genetic modification results in a change of lipid profile on the bacterial membrane.

In one other embodiment, the genetic modification results in a change of amino acid in a protein sequence that in turn results in a change of lipid profile on the bacterial membrane.

In one embodiment, the genetic modification renders a catalytic site inactive. In one embodiment, the genetic modification renders a binding site with a human cell receptor non-functional.

In one embodiment, the genetic modification is a point mutation(s) that results in a change of amino acid in a mimic peptide and renders the mimic peptide not immunogenic i.e. not recognized by the immune system.

In one embodiment, the genetic modification(s) that result(s) in a change of amino acid on the protein sequence are/is chosen so that a single genetic mutation cannot revert the modified amino acid back to original.

The invention encompasses methods for screening for genetic modifications in bacteria. In one embodiment, the method comprises:

- administering, to a subject, a vector designed to genetically modify at least one base of a DNA sequence of interest in a gene or DNA sequence of a naturally occurring bacteria without introducing a double strand break in said DNA sequence,
- subsequently collecting a bacterial sample from the subject, and
- quantitating the level of bacteria containing a genetic modification in said at least one base of a DNA sequence of interest in said bacterial sample.

In one embodiment, the method comprises quantitating the level of bacteria not containing a genetic modification in at least one base of a DNA sequence of interest.

The invention encompasses methods for determining the efficiency of a vector at inducing genetic mutations in situ comprising:

- administering, to a subject, a vector designed to genetically modify at least one base of a DNA sequence of interest in a gene or DNA sequence of a naturally occurring bacteria without introducing a double strand break in said DNA sequence, subsequently collecting a bacterial sample from the subject, quantitating the level of bacteria containing a genetic modification in said at least one base of a DNA sequence of interest and quantitating the level of bacteria not containing a genetic modification in said at least one base of a DNA sequence of interest in said bacterial sample.

The invention also encompasses a method for modifying a naturally occurring bacteria in situ in a subject, said method comprising:

collecting a bacterial sample from the microbiome of the subject, contacting said bacterial sample with a vector designed to genetically modify at least one base of a DNA sequence of interest in a gene or DNA sequence of a naturally occurring bacteria without introducing a double strand break in said DNA sequence, quantitating the level of bacteria containing a genetic modification in said at least one base of a DNA sequence of interest and quantitating the level of bacteria not containing a genetic modification in said at least one base of a DNA sequence of interest in said bacterial sample, and determining thereby the efficiency of said vector at inducing genetic mutations in said subject, and administering, to said subject, said vector designed to genetically modify at least one base of a DNA sequence of interest in a gene or DNA sequence of a naturally occurring bacteria without introducing a double strand break in said DNA sequence, in particular when said determined efficiency is higher than or equal to a given value.

The invention encompasses methods for determining the effect of a genetic mutation on bacterial growth comprising:

administering, to a subject, a vector designed to genetically modify at least one base of a DNA sequence of interest in a gene or DNA sequence of a naturally occurring bacteria, without introducing a double strand break in said DNA sequence, subsequently collecting at least two sequential bacterial samples from the subject, quantitating the level of bacteria containing a genetic modification in said at least one base of a DNA sequence of interest and quantitating the level of bacteria not containing a genetic modification in said at least one base of a DNA sequence of interest in said bacterial samples.

In one embodiment, said genetic modification is a genetic modification of the ClbP gene in pks+ *E. coli* that results in a single-amino acid mutation and the inactivation of the genotoxic activity of Colibactin toxin but maintains the antagonistic activity.

The invention encompasses a bacteriophage, bacterial virus particle or packaged phagemid for modifying in situ a naturally occurring bacteria, said bacteriophage, bacterial virus particle or packaged phagemid comprising a nucleic acid encoding a gene editing enzyme/system for transformation of a target bacteria in a mixed bacterial population wherein said gene editing enzyme/system modifies the genome of said target bacteria without introducing a double strand break in the DNA sequence, but does not lead to the death of the target bacteria. The invention encompasses the use of said bacteriophage, bacterial virus particle or packaged phagemid, wherein the gene editing enzyme/system targets a DNA sequence or gene within the target bacteria encoding a protein which is directly or indirectly responsible for a disease or disorder. The invention encompasses a bacteriophage, bacterial virus particle or packaged phagemid comprising a nucleic acid encoding a gene editing enzyme/system for transformation of a target bacteria in a mixed bacterial population wherein said gene editing enzyme/system modifies the DNA sequence or gene within said target bacteria encoding a protein which is directly or indirectly responsible for a disease or disorder without introducing a double strand break in the DNA sequence, for use for preventing and/or treating said disease or disorder.

Furthermore, a subject's microbiome can affect the metabolism of drug, food supplement, prebiotic or even cosmetic agent, or any compound administered or produced by the host or produced by other bacteria from the host, or affect the interaction of such compounds with the host or action of such compounds on the host. The invention thus also concerns a method to modify in situ interaction of a bacteria from a microbiome of a subject with a compound administered to or produced by said subject or produced by other bacteria from said subject, by modifying at least one bacterial DNA sequence involved in the interaction of said bacteria with said compound, said bacterial DNA sequence being expressed by a bacterial population of the host microbiome, said method comprising:

contacting the bacterial population with a vector that generates a genetic modification in said at least one DNA sequence of the bacteria, involved in the interaction of said bacteria with said compound, in at least some of the bacteria of said population without introducing a double strand break in the DNA sequence;

wherein the genetic modification of said at least one DNA sequence results in a modification of the interaction of the bacteria with said compound; and wherein the genetic modification does not lead to the direct death of the bacteria.

Said interaction of a bacteria with a compound administered to or produced by the subject or produced by other bacteria from said subject, encompasses (i) modification of said compound by said bacteria and/or (ii) competition between said compound and a molecule produced and/or secreted by said bacteria for a ligand from said subject and/or (iii) binding/adsorption of said compound by said bacteria.

In a particular embodiment, the invention concerns a method to modify the metabolism of a given drug in a host treated with said drug, by modifying at least one drug-targeting enzyme expressed by a bacterial population of the host microbiome, comprising:

contacting the bacterial population with a vector that generates a genetic modification in a DNA sequence coding for a drug-targeting enzyme expressed or secreted by the bacteria in at least some of the bacteria of said population without introducing a double strand break in the DNA sequence, wherein the genetic modification of the DNA sequence coding for the drug-targeting enzyme results in a modification of the drug metabolism in the host;

wherein genetic modification does not lead to the direct death of the bacteria.

Said modification of the metabolism of a given drug may be selected from the group consisting of a modification preventing-transformation of a given drug into a toxic compound for the host, a modification preventing hydrolysis of a given drug thus leading to a prolonged activity of said drug, an enzymatic modification of a given drug leading to an increased and/or prolonged activity of said drug, a transformation of said given drug into an active or more active compound, a modification preventing reactivation of detoxified compounds from a given drug.

The invention encompasses compositions and methods to ensure a robust alteration of all targeted bacteria within a microbiome population, thanks to the delivery of a nuclease programmed to discriminate between target bacteria that have been genetically modified in situ and target bacteria in which the modification has not occurred, leading to the specific killing of those in which the modification has not occurred. The present invention thus further concerns a method for ensuring a robust alteration of all targeted bacterial within a microbiome population, said method comprising contacting said microbiome population with a vector comprising a nucleic acid encoding a nuclease programmed to discriminate between targeted bacteria that have been genetically modified in situ and target bacteria in which the modification has not occurred, wherein said programmed nuclease enables the specific killing of targeted bacteria in which the modification has not occurred. In a particular embodiment, the delivery of such nuclease is either on the same DNA payload as the one containing the base-editing nuclease, or on a different payload. In other words, in a particular embodiment, the nucleic acid encoding said programmed nuclease is located on the same vector as the one comprising the nucleic acid encoding the base-editing nuclease or on a different vector. In a particular embodiment, the delivery of such nuclease is either simultaneous with or after the delivery of the payload containing the base-editing. In other words, in a particular embodiment, said vector comprising a nucleic acid encoding said programmed nuclease is administered either simultaneously or after the vector comprising the nucleic acid encoding the base-editing nuclease. If delivered simultaneously, the payload can be engineered to have a delayed targeting process for the programmed nuclease leading to DNA double strand break.

BRIEF DESCRIPTION OF DRAWINGS

In order to better understand the subject matter that is disclosed herein and to exemplify how it may be carried out in practice, embodiments will be described, by way of non-limiting example, with reference to the accompanying drawings. With specific reference to the drawings, it is stressed that the particulars shown are by way of example and for purposes of illustrative discussion of embodiments of the invention.

FIG. 4A) Adenine base editing (ABE=ABE8e) of mCherry. The experiment was performed in the presence (48 colonies analysed) or absence (2 colonies analysed) of a guideRNA targeting the active site of mCherry (tripeptide: M71, Y72, G73). FIG. 4B) Cytosine base editing (CBE=evoAPOBEC1-nCas9-UGI) of mCherry. The experiment was performed in the presence (48 colonies analysed) or absence (2 colonies analysed) of a guideRNA inserting a stop codon into mCherry. Fluorescence was measured by flow cytometry (arbitrary units a.u.) of individual colonies (1 dot represents a single colony after overnight incubation on agar plates).

FIG. 5A) Titers of lambda packaged phagemids comprising a base editor payload (ABE=ABE8e, CBE=evoAPOBEC1-nCas9-UGI). FIG. 5B) Multiplicity of infection (MOI)-dependent adenine base editing (ABE) targeting the active site of β-lactamase gene (K71E) on the genome. FIG. 5C) Multiplicity of infection (MOI)-dependent cytosine base editing (CBE) of β-lactamase. Editing of the active site of β-lactamase diminishes cell growth on carbenicillin plates.

TABLES

Figure 1:
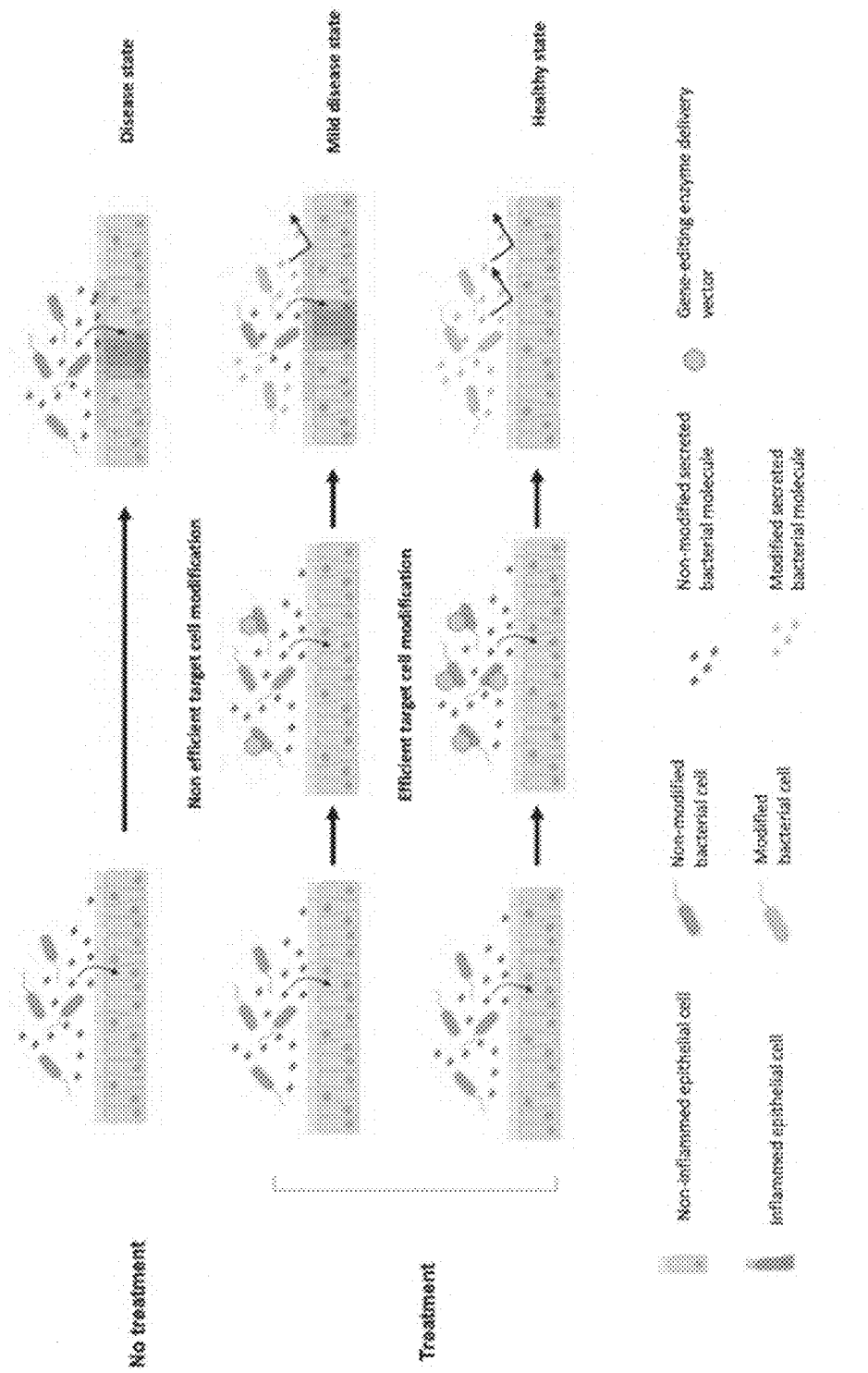
FIG. 1 depicts a method for modifying a naturally occurring bacteria in situ. Bacteria in absence of treatment produce molecules leading to pathogenicity such as inflammation. Upon treatment in the case of non-efficient target cell modification, only a fraction of the bacterial population is genetically modified to express a modified molecule that is non-pathogenic whereas non genetically modified bacteria are still producing the pathogenic variant. This heterogenous bacterial population and their associated molecules lead to mild disease state compared to the no treatment case. Finally, in case of an efficient target cell modification of all the population or a vast majority, the pathogenic variant of the molecule is not present anymore or in quantity low enough to have no pathogenicity and reach a healthy state.
Figure 2:
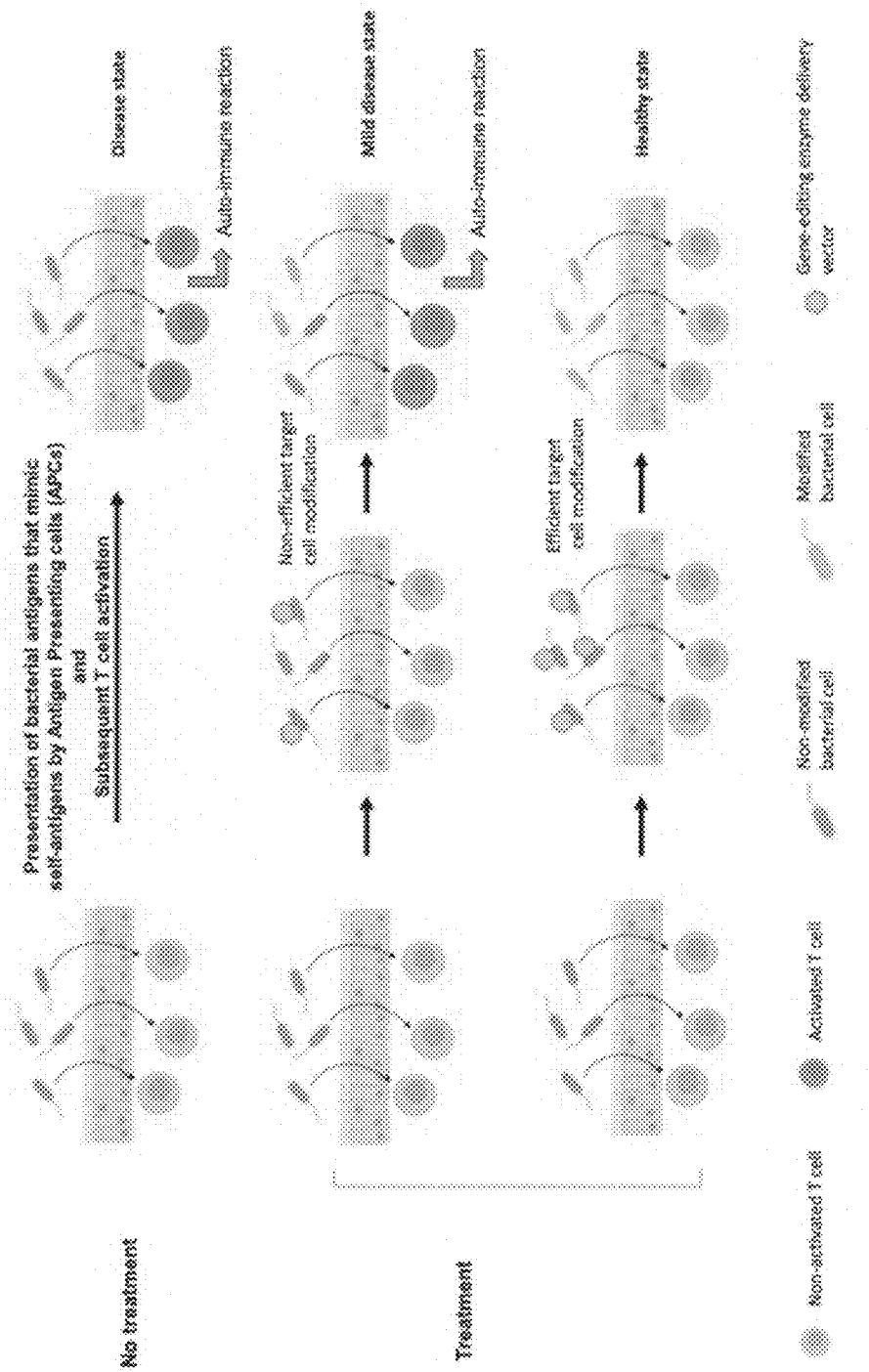
FIG. 2 depicts a method for modification of bacterial antigens in a naturally occurring bacteria in situ where the bacterial antigen mimics a human protein. The bacterial antigen is presented by an antigen presenting cell (APC) to a T cell leading to its activation and an immune response targeted towards on one side the bacterial antigen and on the other side the human protein or self-antigen thus leading to auto-immune reaction.
Figure 3:
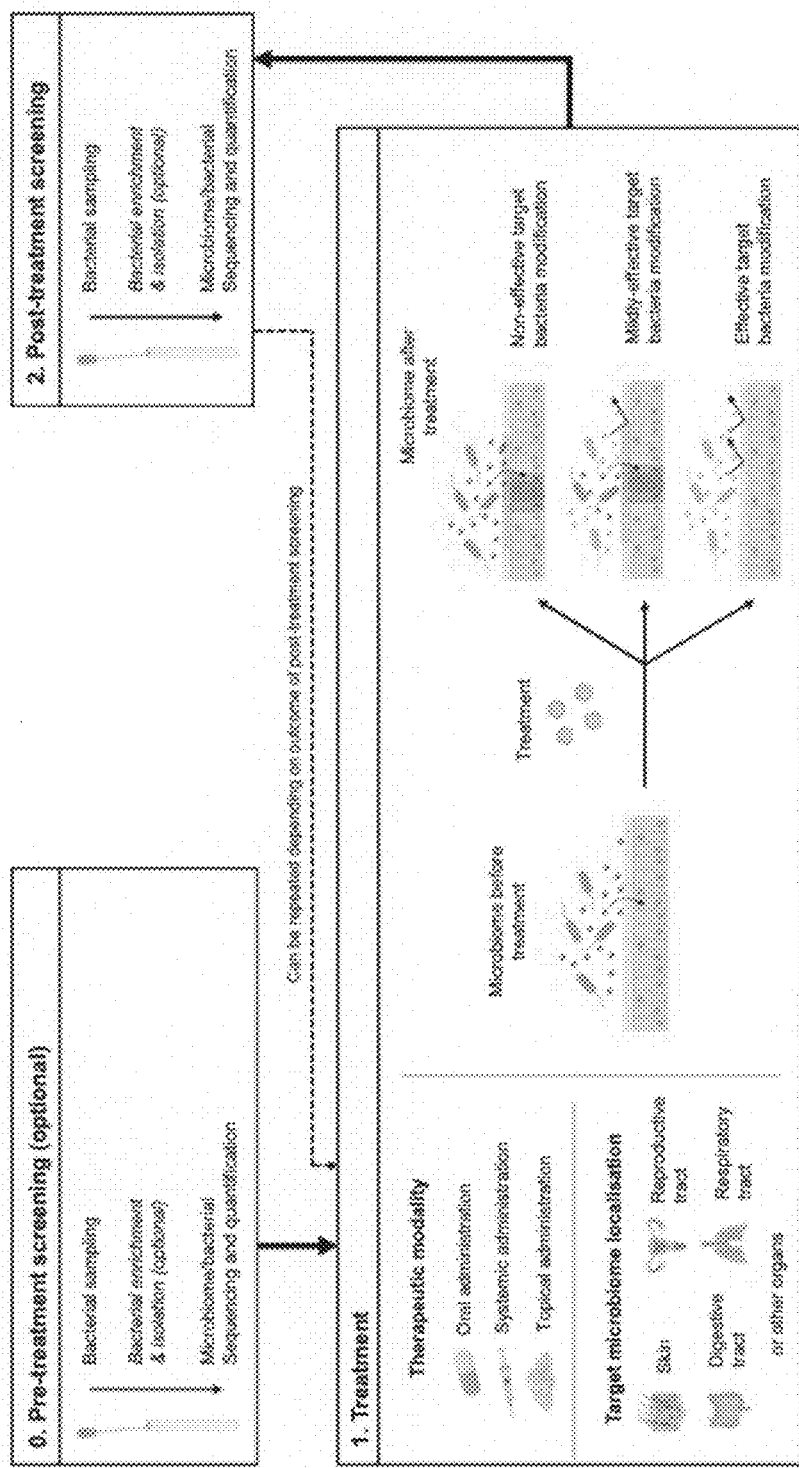
FIG. 3 depicts a screening method for the modification of a naturally occurring bacteria in situ. Before treatment the patient is optionally getting sampled to detect and quantify potential bacterial targets. Then the treatment is administered on different forms (oral, systemic, topical) depending on the target microbiome localization. After treatment the patient is getting sampled to detect and/or quantify bacterial targets and the genetic modifications induced by the treatment.

Table 1 presents gut bacterial species carrying candidate mimic peptide, amino acids sequence of related mimic peptide and Uniprot ID of bacterial and human protein containing each mimic peptide.

Table 2 presents nucleic acid sequences encoding drug-metabolizing gene products (identified by start nucleotide and end nucleotide in the listed contigs).

DETAILED DESCRIPTION OF INVENTION

The invention encompasses compositions, kits and methods, in particular non-therapeutic methods, for modifying a naturally occurring bacteria in situ. The invention further encompasses compositions, kits and methods, in particular non-therapeutic methods, for modifying a non-naturally occurring bacteria, such as one with an ex vivo genetic modification, in situ. The compositions, kits and methods of the invention genetically modify deleterious bacterial strains within the host microbiome to turn them into non-deleterious strains for the host without directly killing these strains.

The invention further encompasses modifications that improve or functionalize non deleterious bacteria. The invention further includes methods for screening for genetic modifications in the bacteria, for determining the efficiency of vectors at inducing these genetic mutations, and for determining the effects of these mutations on bacterial growth or on any bacterial function, for increasing the ratio of modified bacteria vs non-modified bacteria in situ, for increasing the chance that this approach leads to a positive outcome in a patient.

Preferably, the genetic modifications are modifications of a DNA sequence in the naturally occurring bacteria in situ without introducing a double strand break in the DNA sequence. Thus, the method includes generating no cleavages in the DNA sequence, generating a nick in one strand of the DNA sequence, or generating a staggered nicks in both strands of the DNA sequence, that do not lead to a double strand break in the DNA sequence.

Provided herein are compositions, kits and methods of treating, preventing or curing microbiome-associated diseases or disorders by modulating either the molecules expressed and/or secreted by bacterial populations of the microbiome or their expression/secretion levels, in a specific manner that will result in the modification of the interactions between part or all of these populations and the host in a way that decreases their deleterious potential on host health, and which will not result in the direct death of these populations, a direct significant inhibition of their growth or impairment of major bacterial function. The invention also concerns a vector encoding enzymes or systems for inducing genetic modifications in naturally occurring bacteria in situ for use for treating, preventing or curing a microbiome-associated disease or disorder by modulating either the molecules expressed and/or secreted by bacterial populations of the microbiome or their expression/secretion levels, in particular in a specific manner that will result in the modification of the interactions between part or all of these populations and the host in a way that decreases their deleterious potential on host health, and which will not result in the direct death of these populations, a direct significant inhibition of their growth or impairment of major bacterial function. The invention also concerns the use of a vector encoding enzymes or systems for inducing genetic modifications in naturally occurring bacteria in situ in the manufacture of a medicament intended to treat, prevent or cure a microbiome-associated disease or disorder by modulating either the molecules expressed and/or secreted by bacterial populations of the microbiome or their expression/secretion levels, in particular in a specific manner that will result in the modification of the interactions between part or all of these populations and the host in a way that decreases their deleterious potential on host health, and which will not result in the direct death of these populations, a direct significant inhibition of their growth or impairment of major bacterial function.

The invention encompasses the use of a vector that can transduce with high efficiency a nucleic acid, preferably a plasmid or a phagemid, into a bacterial population within the microbiome that allows the expression of an exogenous enzyme that will modify a DNA or gene sequence. The bacterial population can be a mixed bacterial population, comprising different strains of the same species; alternatively, the bacterial population can be a mixed bacterial population, comprising different strains of different species. In some embodiments, the DNA sequence or gene has a direct or indirect effect on the interactions of the bacteria with the host. Thus, the invention encompasses vectors for use in transducing with high efficiency a nucleic acid, preferably a plasmid or a phagemid, into a bacterial population.

In some embodiments, the DNA sequence or gene having a direct effect includes a DNA sequence or gene expressing a toxin that interacts with host cells, or a bacterial protein or peptide that includes a sequence of amino acids that mimic a sequence of amino acids present in the host proteins or peptides.

In some embodiments, the DNA sequence or gene having an indirect effect includes DNA sequences or genes that encode for an enzyme expressed, displayed on the membrane or secreted by the bacteria that is involved in the internal production or modification of a sugar, lipid, metabolite or protein that is present inside the bacteria, expressed or displayed on the membrane of the bacteria, secreted by the bacteria or imported by the bacteria.

Preferably, the precise modification of the DNA sequence or gene sequence is performed so that it minimizes any effect on the ability of the bacteria to grow and interact with other microorganisms in its biological environment, but modifies its interaction with the host or its growth or resistance potential during a treatment.

Methods of Genetic Modification

The invention encompasses methods of modifying a naturally occurring bacteria in situ. Preferably, the genetic modification does not lead to the death of bacteria. More preferably, the genetic modification results in less than a 5%, 10%, 20%, or 50% growth disadvantage of the modified bacteria in vivo due to the genetic modification. Even more preferably, the genetic modification does not result in any growth disadvantage of the modified bacteria in vivo due to the modification. Preferably, the genetic modification is a modification of a DNA sequence in the naturally occurring bacteria in situ without introducing a double strand break in the DNA sequence, In a preferred embodiment, the bacteria are contacted in situ with a vector that can transfer with high efficiency a nucleic acid into the bacteria to express an exogenous enzyme in the bacteria that results in a genetic modification. In a preferred embodiment, the exogenous enzyme can result in this genetic modification through base editing strategies where dCas9 (dead-Cas9) or nCas9 (nickase Cas9) is fused to cytosine or adenosine deaminase domain and directed to the target sequence to make the desired modification.

In a preferred embodiment, the exogenous enzyme can result in this genetic modification through prime editing strategies where dCas9 (dead-Cas9) or nCas9 (nickase Cas9) is fused to reverse transcriptase domain and directed to the target sequence to make the desired modification with the help of a pegRNA (prime editing guide RNA).

Nevertheless, the invention also contemplates introducing a double strand break or a single strand break i.e. a nick in the bacterial DNA at a specific sequence, for example with a CRISPR/Cas system, together with non-homologous end joining (NHEJ) or homologous recombination (HR) to generate the desired genetic modification. Preferably, the double strand break or the single strand break is generated in the presence of an editing template comprising homologous regions with DNA regions located around the specific sequence located in the bacterial DNA.

The genetic modification can be a point mutation(s), a deletion(s), insertion(s) or any combination thereof.

In some embodiments, the genetic modification can inactivate, reduce, increase or induce the expression of a DNA sequence or gene. The genetic modification can be in the translated or untranslated regions of a gene. The genetic modification can be in the promoter region of a gene or within any other region involved in gene regulation.

In some embodiments, the DNA sequence or gene inactivation can be a point mutation(s) inside the coding sequence (starts with start codon, ends with stop codon). More precisely, the DNA sequence or gene inactivation can be performed by a point mutation(s) converting one or several codons to stop codon (TAA, TAG, TGA). Alternatively, the DNA sequence or gene inactivation can be performed by a point mutation(s) converting the start codon (ATG, GTG, TTG) or any in-frame start codon in 5, 10, 20, 50, 100 bp of the predicted start codon into a non-start codon or a stop codon. Alternatively, the DNA sequence or gene inactivation can be performed by point mutation(s) introducing rare codons inside the codon sequence. Alternatively, the DNA sequence or gene inactivation can be performed by point mutation(s) introducing non-synonymous amino acid change(s) in a catalytic site making the protein inactive for the function associated to this catalytic site. Alternatively, the DNA sequence or gene inactivation can be performed by point mutation(s) introducing non-synonymous amino acid change(s) in a site involving binding other molecules where the interaction is necessary for the protein activity.

In some embodiments, the DNA sequence or gene inactivation can be a point mutation(s) outside the coding sequence. Point mutation(s) can be in the promoter region of a gene (e.g. −35 bp region, −10 bp region, transcription start site (TSS)), in the Ribosome Binding Site (RBS) of the gene or within any other region involved in regulation (e.g. transcription factor binding site, operator binding site, riboswitch . . . ).

In some embodiments, the genetic modification can lead to DNA sequence or gene activation.

In some embodiments, the genetic modification can be a point mutation(s) that revert a previously characterized mutation that inactivate, decrease or increase the activity of a gene or pathway.

In some embodiments, the genetic modification can be a point mutation(s) leading to modulation of DNA sequence or gene expression and regulation. Point mutation(s) can be in promoter region of a gene (e.g. −35 bp region, −10 bp region, transcription start site (TSS)), in the Ribosome Binding Site (RBS) of the gene, within any other region involved in regulation (e.g., transcription factor binding site, operator binding site, RNAse recognition site, riboswitch, methylation sit, etc.) or in any other DNA sequence or gene regulating the DNA sequence or gene of interest such as a repressor, an antisense RNA, an activator.

In some embodiments, the genetic modification can be point mutation(s) leading to modulation of post translational modification(s) (e.g., phosphorylation, glycosylation, acetylation, pupylation, etc.). More particularly the modification can be a point mutation in the post translational modification site. Alternatively, the genetic modification can disrupt the DNA sequence or gene responsible for post-translational modification(s).

In another embodiment, the genetic modification is a point mutation(s) that revert a mutation that leads to an increase of pathogenicity.

In a particular embodiment, the genetic modification does not integrate a phage genome or exogenous DNA into the host bacterial chromosome or endogenous plasmid(s). In a particular embodiment, the genetic modification does not result in expression of an exogenous protein from an integrated exogenous DNA in the host bacterial chromosome or endogenous plasmid(s). In a more particular embodiment, the genetic modification does not involve either NHEJ or HR endogenous repair mechanism of the host bacteria.

In some embodiments, the genetic modification results in the change in at least 1, 2, 3, 4, 5, 6, 7, 8, 9, 10, 11, 12, 13, 14, 15, 20, 25, 30, 35, 40, 45, 50, 100, 200, 500, etc. amino acids to a different amino acid.

The invention encompasses methods, in particular non-therapeutic methods, of modulating host—microbiome interaction by genetically modifying naturally occurring bacteria in situ. Preferably, the naturally occurring bacteria is involved in microbiome associated disorder or disease. In preferred embodiments, the method comprises genetically modifying a DNA sequence responsible for the microbiome associated disorder or disease in the naturally occurring bacteria in situ, wherein the genetic modification reduces the effects of the microbiome associated disorder or disease, and wherein the genetic modification does not lead to the death of bacteria. The invention further encompasses a vector encoding enzymes or systems for inducing genetic modifications in naturally occurring bacteria in situ for use in a method for reducing the effects of a microbiome associated disorder or disease, wherein said vector genetically modifies a DNA sequence, in the naturally occurring bacterial in situ, responsible for said microbiome associated disorder or disease, and wherein the genetic modification does not lead to the death of bacteria. Preferably, the bacteria with the genetic modification does not have a reduced in vivo growth rate as compared to the same bacteria without the genetic modification.

In some embodiments, the genetic modification occurs within a pathogenic bacterial DNA sequence or gene encoding a virulence factor to block pathogenesis, which de-facto might reduce the fitness of the bacteria, since virulence factor often confer a fitness advantage of the pathogenic bacteria over its bacterial competitors. This might for example lead to a lower growth-rate.

In other embodiments, the genetic modification occurs within commensal bacteria or opportunistic pathogens, and the modification has a small or no impact on the growth rate of this bacteria as a commensal bacteria.

The invention encompasses methods to prevent or intervene in the course of an auto-immune disease or reaction in a predisposed host by modifying the immunogenic profile of a bacterial population of the human or animal microbiome. In preferred embodiments, the method comprises contacting the bacterial population with a vector that generates a genetic modification in a DNA sequence coding for an immunogenic component expressed or secreted by the bacteria in at least some of the bacteria of said population, wherein the genetic modification of the DNA sequence coding for the immunogenic component results in loss of the immunogenic effect of said immunogenic component, and wherein the genetic modification does not lead to the direct death of the bacteria. The invention further encompasses a vector encoding enzymes or systems for inducing genetic modifications for use in a method to prevent or intervene in the course of an auto-immune disease or reaction in a predisposed host by modifying the immunogenic profile of a bacterial population of the human or animal microbiome. In preferred embodiments, said vector generates a genetic modification in a DNA sequence coding for an immunogenic component expressed or secreted by the bacteria in at least some of the bacteria of said population, wherein the genetic modification of the DNA sequence coding for the immunogenic component results in loss of the immunogenic effect of said immunogenic component, and wherein the genetic modification does not lead to the direct death of the bacteria.

Preferably, the bacteria with the genetic modification does not have a reduced in vivo growth rate as compared to the same bacteria without the genetic modification.

In some embodiments, the genetic modification results in a change of amino acid in a mimic peptide and renders the mimic peptide not immunogenic or not recognized by the immune system. In some embodiments, the genetic modification results in a change of sugar profile on the bacterial membrane. In some embodiments, the genetic modification results in a change of amino acid in a protein sequence that results in a change of sugar profile on the bacterial membrane. In some embodiments, the genetic modification results in a change of lipid profile on the bacterial membrane. In some embodiments, the genetic modification results in a change of amino acid in a protein sequence that results in a change of lipid profile on the bacterial membrane. In some embodiments, the genetic modification results in a change at the protein sequence level leading to an inactive catalytic site. In some embodiments, the genetic modification renders a binding site with a human cell receptor non-functional. In some embodiments, the genetic modification renders the bacteria more sensitive to detection by human immune cells.

Modification of a Bacterial Toxin Gene Sequence

In some embodiment, the genetic modification is made in a toxin gene sequence so that the toxin is still produced, expressed and or secreted but renders its toxigenic effect null, resulting in the modification of one or multiple amino acids of the catalytic site of the enzyme so that it cannot exert its toxigenic effect on the host cells.

Alternatively, the genetic modification is made in a toxin gene sequence so that the toxin gene sequence is not expressed or disrupted, resulting in the inactivation of the toxin.

The targeted bacterial toxin can be an exotoxin or endotoxin. Exotoxins are generated and actively secreted; endotoxins remain part of the bacteria. The response to a bacterial toxin can involve severe inflammation and can lead to sepsis.

Preferred toxins include Colibactin of *E. coli*, Toxin A and other enzymes (e.g., hemolysin, leukotoxin, exfoliative toxin, enterotoxin, and toxic-shock syndrome toxin-1 (TSST-1)) from *Staphylococcus aureus* as described in Tam and Torres, Microbiol Spectr. 2019 March; 7(2), which is hereby incorporated by reference, and fragilysin (Bft) from Enterotoxigenic (ETBF) strains of *Bacteroides fragilis*, Botulinum neurotoxin, Tetanus toxin, Diphteria toxin, Anthrax toxin, Alpha toxin, Pertussis toxin, Shiga toxin, Heat-stable enterotoxin (*E. coli* ST), or any toxin described in Henkel et al., (Toxins from Bacteria in EXS. 2010; 100: 1-29, which is hereby incorporated by reference).

By "colibactin" is meant herein a secondary metabolite synthetized by the clbA-S genes present in the 54-kb pathogenicity pks island, a genetic island encoding a non-ribosomal peptide synthetase-polyketide synthase (NRPS-PKS) assembly line in Enterobacteriaceae. Colibactin is typically produced as a prodrug moiety that is exported in the periplasm by the efflux pump ClbM and then hydrolyzed by the periplasmic membrane-bound ClbP protein with a peptidase activity, which releases the active colibactin.

In preferred embodiments, the genetic modification is a point mutation(s) leading to toxin gene disruption such as described previously.

Preferably, the bacteria with the genetic modification do not have a reduced in vivo growth rate as compared to the same bacteria without the genetic modification.

Preferably, the genetic modification(s) are done so that a single genetic mutation cannot revert the activity of the toxin. This can be achieved by changing the original amino acid for another amino acid that cannot be reverted to original by a single substitution.

In one embodiment, the method comprises making a genetic modification in the ClbP gene in pks+ *E. coli* that result in a single-amino acid mutation and the inactivation of the genotoxic activity of Colibactin toxin, but maintains the antagonistic activity. In a particular embodiment, the genetic modification is in the ClbP gene in pks+ *E. coli* and results in a single-amino acid mutation and the inactivation of the genotoxic activity of Colibactin toxin, while maintaining its antagonistic activity.

As used herein, the ClbP gene is typically of sequence SEQ ID NO: 2316 and typically encodes a protein of sequence SEQ ID NO: 2317.

Preferably, the genetic modification is at codons of the ClbP gene encoding amino acids S95 or K98 of the protein encoded by the ClbP gene, in particular at codons of the ClbP gene encoding amino acids S95 or K98 of SEQ ID NO: 2317. Most preferably, the genetic modification is a mutation S95A, S95R or K98T in the ClbP gene.

In some embodiments, the genetic modification is made in a Shigella toxin gene such as, without limitation, stx1 and stx2. In some embodiments, the genetic modification is made in a E. coli toxin gene such as, without limitation, Sbx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), stx2k.

Modification of Other Bacterial Virulence Gene Sequence

In one embodiment, the modification can be made in and inactivate a virulence factor. A virulence factor can be any substance produced by a pathogen that alters host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, scavenging factors and factors that promote biofilm formation.

In some embodiments, the genetic modification is made in a E. coli virulence factor gene such as, without limitation, EHEC-HlyA, fimA, fimF, fimH, neuC, kpsE, sfa, foc, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, or genes within T1SS, T2SS, T3SS, T4SS, T5SS, T6SS (secretion systems).

In one embodiment, the method comprises making a genetic modification in the FimH gene in E. coli that results in reverting the following mutations: N70S and S78N associated with AEIC strains[3]. In a particular embodiment, the genetic modification is made in the FimH gene in E. coli.

In the context of the invention, the FimH gene typically encodes a Type 1 fimbrin D-mannose specific adhesin. The FimH gene is typically of sequence SEQ ID NO: 2319 and typically encodes a protein of sequence SEQ ID NO: 2318.

In one embodiment, the genetic modification is made in the FimH gene in E. coli and preferably results in reverting the mutations N70S and S78N associated with AEIC strains.

In one embodiment, the method comprises making a genetic modification in the blc gene in E. coli that result in reverting the mutation G84E (G251A at the nucleotide level) potentially associated with gut inflammation[4].

In the context of the invention, the blc gene typically encodes an Outer membrane lipoprotein Blc. The bcl gene is typically of sequence SEQ ID NO: 2321 and typically encodes a protein of sequence SEQ ID NO: 2320.

In one embodiment, the genetic modification is made in the blc gene in E. coli and preferably results in reverting the mutation G84E (G251A at the nucleotide level) potentially associated with gut inflammation.

In some embodiments, the genetic modification is made in a Yersinia pestis virulence factor gene such as, without limitation, yscF (plasmid-borne (pCDI) T3SS external needle subunit).

In some embodiments, the genetic modification is made in a Yersinia pestis virulence factor gene such as, without limitation, yscF (plasmid-borne (pCDI) T3SS external needle subunit).

In some embodiments, the genetic modification is made in a Francisella tularensis virulence factor gene such as, without limitation, fslA.

In some embodiments, the genetic modification is made in a Bacillus anthracis virulence factor gene such as, without limitation, pag (Anthrax toxin, cell-binding protective antigen).

In some embodiments, the genetic modification is made in a Vibrio cholera virulence factor gene such as, without limitation, ctxA and ctxB (cholera toxin), tcpA (toxin co-regulated pilus), and toxT (master virulence regulator).

In some embodiments, the genetic modification is made in a Pseudomonas aeruginosa virulence factor genes such as, without limitation, pyoverdine (e.g., sigma factor pvdS, biosynthetic genes pvdL, pvdI, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT).

In some embodiments, the genetic modification is made in a Klebsiella pneumoniae virulence factor gene such as, without limitation, fimA (adherence, type I fimbriae major subunit), and cps (capsular polysaccharide).

In some embodiments, the genetic modification is made in an Acinetobacter baumannii virulence factor gene such as, without limitation, ptk (capsule polymerization) and epsA (assembly).

In some embodiments, the genetic modification is made in a Salmonella enterica Typhi virulence factor gene such as, without limitation, MIA (invasion, SPI-1 regulator), ssrB (SPI-2 regulator), and those associated with bile tolerance, including efflux pump genes acrA, acrB and tolC.

In some embodiments, the genetic modification is made in a Fusobacterium nucleatum virulence factor gene such as, without limitation, FadA and TIGIT.

In some embodiments, the genetic modification is made in a Bacteroides fragilis virulence factor gene such as, without limitation, bft.

In some embodiments, the genetic modification is made in a Cutibacterium acnes porphyrins gene, a CAMP-factor (CAMP1, CAMP2, CAMP3, CAMP4), Hyaluronate lyase (HYL-IB/II, HYL-IA), Lipases (GehA, GehB), Haemolysins, Sialidases, Endoglycoceramidases, Endo-ß-N-acetyl-glucosaminidase, Dermatan sulphate adhesin (DsA1, DsA2), Proline-Threonine Repeats (PTRs) or in any virulence factors included on the acne associated genomic loci 1, 2, 3(plasmid), 4 such as a tight adhesion locus (tad), Streptolysin S-associated genes (sag), nonribosomal peptide synthetases (NRPS) as described in Tomida et al[5], which is hereby incorporated by reference.

Modification of a Mimic Peptide Gene Sequence

In some embodiments, the genetic modification is made in a mimic peptide gene sequence so that the homology with the human peptide sequence is reduced, and therefore results in the mimic peptide being not recognized anymore by the host immune system. Mimic peptides of particular interest are bacterial mimic peptides that are associated with auto-immune diseases, for example those mentioned in Negi et al.[6], which are hereby incorporated by reference. Of particular interest are the gene sequences encoding any of the mimic peptides in S1 Table of Negi et al.

In a particular embodiment, the mimic peptide is one of the candidate mimic peptides disclosed in Table 1 below. In a particular embodiment, said mimic peptide is selected from the group consisting of the peptides of sequence SEQ ID NO: 19 to 2313.

In preferred embodiments, the mimic peptide is from Proteobacteria or Firmicutes. Of particular interest are the gene sequences encoding 24 gut bacterial peptides identified by Negi et al. with homology to four human peptides from Low molecular weight phosphotyrosine protein phosphatase, Aldehyde dehydrogenase family 3 member B1, Maleylacetoacetate isomerase and Uracil-DNA glycosylase. These gene sequences can be modified to reduce the homology with the human sequences and prevent cross-reactivity of those recognized by the host immune system with the human counterpart.

In a preferred embodiment, the genetic modification is in the *Bacteroides faecis* or *Bacteroides thetaiotaomicron* beta-galactosidase gene. Preferably, the *Bacteroides faecis* or *Bacteroides thetaiotaomicron* beta-galactosidase protein with the genetic modification shows lower homology with human MYH6 cardiac peptide as compared to the *Bacteroides faecis* or *Bacteroides thetaiotaomicron* beta-galactosidase protein without the genetic modification[2]. Preferably the genetic modification is performed in the peptides fragment recognized as epitope by the human immune system leading to a weaker or absence of epitope recognition by the human immune system[2].

In a preferred embodiment, the genetic modification is in human commensal bacteria encoding a Ro60 ortholog gene. Preferably, the Ro60 protein resulting from the genetic modification shows lower homology with human Ro60 peptide as compared to the original protein. Preferably the genetic modification is performed in the DNA sequence corresponding to peptides fragment recognized as epitope by the human immune system leading to a weaker or absence of epitope recognition by the human immune system. Preferably the human bacterial commensal targeted for genetic modification are: *Propionibacterium propionicum, Corynebacterium amycolatum, Actinomyces massiliensis, Bacteroides thetaiotaomicron*. Even more preferably the human bacterial commensal targeted for genetic modification is *Propionibacterium propionicum*[7].

In a preferred embodiment, the genetic modification is in human commensal bacterial DNA sequence encoding a peptide that mimic insulin B 9-25, a self-epitope involved in type 1 diabetes[8]. The genetic mutation reduces homology to the insulin B9-25 epitope SHLVEALYLVCGERGFF (SEQ ID NO: 9). In a preferred embodiment, the target bacteria belong to the Firmicutes phylum. In a preferred embodiment, the target gene in the target bacteria is part of the transketolase N superfamily[8].

In a preferred embodiment, the genetic modification is in *Roseburia intestinalis* encoding a peptide that mimic the epitope of the autoantigen $\beta_2$-glycoprotein I ($\beta_2$GPI), a self-epitope involved in antiphospholipid syndrome (APS). The genetic mutation is reducing homology to the T cell ($\beta_2$GPI) epitope KVSFFCKNKEKKCSY (SEQ ID NO: 10) and/or B cell epitope VSRGGMRKFIC (SEQ ID NO: 11)[28].

Modification of an Antibiotic-Resistance Gene Sequence

In some embodiments, the modification is made in an antibiotic-resistance gene sequence, carried on the chromosome or on a plasmid, to render the bacteria sensitive to an antibiotic without exerting a direct selective pressure on the bacteria in the absence of the related antibiotic.

In some embodiment, the genetic modification is made to revert mutations in endogenous genes, some of which are essential to the bacteria, that confer resistance to antibiotics such as: RpoB rifampicin resistant mutant, 23S rRNA erythromycin resistant mutant, GyrA (fluoro) quinolone resistant mutant, GyrB (fluoro) quinolone resistant mutant, RpsL streptomycin resistant mutant, DHFR trimethoprim resistant mutant, fusA fusidic acid resistant mutant, fmt actinonin resistant mutant, gidB streptomycin resistant mutant, ompR multidrug resistant mutant, marR multidrug resistant mutant, Ion multidrug resistant mutant, mgrB colistin resistant mutant, pmrA colistin resistant mutant, acrR multidrug resistant mutant, cysB amdinocillin resistant mutant, 16S rRNA methyltransferase.

In some embodiments, the antibiotic resistance gene can be, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecI, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FolP, Tetracycline inactivation enzyme TetX, TetA, TetB, TetC, Tet30, Tet31, TetM, TetO, TetQ, Tet32, Tet36, MacAB-ToIC, MsbA, MsrA,VgaB, EmrD, EmrAB-ToIC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database at card. mcmaster.ca/.

In preferred embodiments, the antibiotic is selected from the group consisting of penicillins such as penicillin G, penicillin K, penicillin N, penicillin O, penicillin V, methicillin, benzylpenicillin, nafcillin, oxacillin, cloxacillin, dicloxacillin, ampicillin, amoxicillin, pivampicillin, hetacillin, bacampicillin, metampicillin, talampicillin, epicillin, carbenicillin, ticarcillin, temocillin, mezlocillin, and piperacillin; cephalosporins such as cefacetrile, cefadroxil, cephalexin, cefaloglycin, cefalonium, cephaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; polymyxins such as polysporin, neosporin, polymyxin B, and polymyxin E, rifampicins such as rifampicin, rifapentine, and rifaximin; Fidaxomicin; quinolones such as cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, temafloxacin, tosufloxacin, clinafloxacin, gatifloxacin, gemifloxacin, moxifloxacin, sitafloxacin, trovafloxacin, prulifloxacin, delafloxacin, nemonoxacin, and zabofloxacin; sulfonamides such as sulfafurazole, sulfacetamide, sulfadiazine, sulfadimidine, sulfafurazole, sulfisomidine, sulfadoxine, sulfamethoxazole, sulfamoxole, sulfanitran, sulfadimethoxine, sulfametho-xypyridazine, sulfametoxydiazine, sulfadoxine, sulfametopyrazine, and terephtyl; macrolides such as azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin; ketolides such as telithromycin, and cethromycin; fluoroketolides such as solithromycin; lincosamides such as lincomycin, clindamycin, and pirlimycin; tetracyclines such as demeclocycline, doxycycline, minocycline, oxytetracycline, and tetracycline; aminoglycosides such as amikacin, dibekacin, gentamicin, kanamycin, neomycin, netilmicin, sisomicin, tobramycin, paromomycin, and streptomycin; ansamycins such as geldanamycin, herbimycin, and rifaximin; carbacephems such as loracarbef; carbapenems such as ertapenem, doripenem, imipenem (or cilastatin), and meropenem; glycopeptides such as teicoplanin, vancomycin, telavancin, dalbavancin, and oritavancin; lincosamides such as clindamycin and lincomycin; lipopeptides such as daptomycin; monobactams such as aztreonam; nitrofurans such as furazolidone, and nitrofurantoin; oxazolidinones such as linezolid, posizolid, radezolid, and torezolid; teixobactin, clofazimine, dapsone, capreomycin, cycloserine, ethambutol, ethionamide, isoniazid, pyrazinamide, rifabutin, arsphenamine, chloramphenicol, fosfomycin, fusidic acid, metronidazole, mupirocin, platensimycin, quinupristin (or dalfopristin), thiamphenicol, tigecycline, tinidazole, trimethoprim, alatrofloxacin, fidaxomicin, nalidixic acid, rifampin, derivatives and combination thereof.

Modification to a Conserved Sequence

In some embodiments, the modification of the amino-acid sequence is made so that the edited sequence corresponds to an amino-acid sequence encoding for the same or a related protein/function/activity coming from one or multiple different strains from the same species, or from a related species, or from the same genus, or from any other bacteria from the microbiome. The edited sequence can correspond to a paralog, ortholog or analog of the original sequence.

This modification can reduce the potential selective pressure applied to the edited bacteria by ensuring a relatively similar function while not having the same exact amino-acid sequence.

Modification of DNA Sequences Involved in Interactions Between Bacteria and Compounds Administered to or Produced by the Subject or Produced by Other Bacteria The invention also concerns a method to modify in situ interaction of a bacteria from a microbiome of a subject with a compound administered to or produced by said subject or produced by other bacteria from said subject, by modifying at least one bacterial DNA sequence involved in the interaction of said bacteria with said compound, said bacterial DNA sequence being expressed by a bacterial population of the host microbiome, said method comprising:

contacting the bacterial population with a vector that generates a genetic modification in said at least one DNA sequence of the bacteria, involved in the interaction of said bacteria with said compound, in at least some of the bacteria of said population without introducing a double strand break in the DNA sequence;

wherein the genetic modification of said at least one DNA sequence results in a modification of the interaction of the bacteria with said compound; and wherein the genetic modification does not lead to the direct death of the bacteria.

By "interaction of a bacteria with a compound administered to or produced by a subject or produced by other bacteria from said subject" is meant any type of interaction, inducing or not a modification in the structure and/or activity of said compound, and involving any component of the bacteria (including enzymes, receptors, channels, sugars, lipids, etc. . . . ) in any location of said bacteria (e.g. at the membrane, capsule, in the cytoplasm, etc). Said interaction of a bacteria with a compound administered to or produced by the subject or produced by other bacteria encompasses (i) modification of said compound by said bacteria and/or (ii) competition between said compound and a molecule produced and/or secreted by said bacteria for a ligand from said subject and/or (iii) binding/adsorption of said compound by said bacteria.

By "ligand" is meant herein a substance binding, in particular specifically binding, to a compound of interest. In the context of the invention, ligands from the subject encompasses receptors, enzymes, immune molecules, etc. . . . , able to bind said compound of interest.

Said compound administered to said subject can be any type of compound such as a drug, a prebiotic, a cosmetic agent, a food supplement, etc. . . .

Said compound produced by the subject may be, without limitation, bile acids (such as taurocholic acid, glycocholic acid, taurochenodeoxycholic acid, glycochenodeoxycholic acid, deoxycholic acid, lithocholic acid, and derivatives of cholic, chenodeoxycholic and deoxycholic acids), hormones (such as Adrenaline (or epinephrine), Melatonin, Noradrenaline (or norepinephrine), Triiodothyronine, Thyroxine, Dopamine, Prostaglandins, Leukotrienes, Prostacyclin, Thromboxane, Amylin, Anti-Müllerian hormone (or Müllerian-inhibiting factor/hormone), Adiponectin, Adrenocorticotropic hormone (or corticotropin), Angiotensinogen, Angiotensin, Antidiuretic hormone (or vasopressin, arginine vasopressin), Atrial natriuretic peptide (or atriopeptin), Brain natriuretic peptide, Calcitonin, Cholecystokinin, Corticotropin-releasing hormone, Cortistatin, Enkephalin, Endothelin, Erythropoietin, Follicle-stimulating hormone, Galanin, Gastric inhibitory polypeptide, Gastrin, Ghrelin, Glucagon, Glucagon-like peptide-1, Gonadotropin-releasing hormone, Growth hormone-releasing hormone, Hepcidin, Human chorionic gonadotropin, Human placental lactogen, Growth hormone, Inhibin Peptide, Insulin, Insulin-like growth factor (or somatomedin), Leptin, Lipotropin, Luteinizing hormone, Melanocyte stimulating hormone, Motilin, Orexin, Osteocalcin, Oxytocin (or pitocin), Pancreatic polypeptide, Parathyroid hormone, Pituitary adenylate cyclase-activating peptide, Prolactin (or leuteotropic hormone), Prolactin-releasing hormone, Relaxin, Renin, Secretin, Somatostatin (or growth hormone-inhibiting hormone or growth hormone release-inhibiting hormone or somatotropin release-inhibiting factor or somatotropin release-inhibiting hormone), Thrombopoietin, Thyroid-stimulating hormone (or thyrotropin), Thyrotropin-releasing hormone, Vasoactive intestinal peptide, Guanylin, Uroguanylin, Testosterone, Dehydroepiandrosterone, Androstenedione, Dihydrotestosterone, Aldosterone, Estradiol, Estrone, Estriol, Cortisol, Progesterone, Calcitriol or Calcidiol) or perspiration compounds.

In a particular embodiment, the invention concerns a method to modify the metabolism of a given drug in a host treated with said drug, by modifying at least one drug-targeting enzyme expressed by a bacterial population of the host microbiome, comprising:

contacting the bacterial population with a vector that generates a genetic modification in a DNA sequence coding for a drug-metabolizing gene product, in particular a drug-targeting enzyme, expressed or secreted by the bacteria in at least some of the bacteria of said population without introducing a double strand break in the DNA sequence, wherein the genetic modification of the gene coding for the drug-metabolizing gene protein, in particular the drug-targeting enzyme, results in a modification of the drug metabolism in the host;

wherein genetic modification does not lead to the direct death of the bacteria.

By "drug metabolism" is meant herein the biotransformation of pharmaceutical substances in the body. In the context of the invention, drug metabolism encompasses both the pathway leading to the elimination of the drug and the more general evolution of the drug activity in the subject one administered to said subject.

Said modification of the metabolism of a given drug may be selected from the group consisting of preventing transformation of the given drug into a toxic compound for the host, preventing hydrolysis of the given drug thus leading to a prolonged activity of said drug, an enzymatic modification of the given drug leading to an increased and/or prolonged activity of said drug, a transformation of said given drug into an active or more active compound, a modification preventing reactivation of detoxified compounds from a given drug.

Said given drug may be selected from the group consisting of Nicardipine.HCl, Risperidone, Tolcapone, Azathioprine, Entacapone, Exemestane, Nimodipine, Capsaicin, Dexamethasone, Ethacrynic Acid, Rifampin (Rifampicin), Sulindac, Vorinostat, Dolasetron, Mycophenolate Mofetil, Zidovudine (3'-Azido-3'-Deoxythymidine), Allopurinol, Betamethasone, Bisacodyl, Estradiol, Famciclovir, Flutamide, Hydrocortisone, Hydrocortisone Acetate, Methylprednisolone, Metronidazole, Nabumetone, Pantoprazole, Prednisolone, Progesterone, Prednisone, Spironolactone, Sulfasalazine, Tinidazole, Fluoxetine.HCl, Misoprostol, Megestrol Acetate, Capecitabine, Chenodiol (Chenodeoxycholic Acid), Clofazimine, Clonazepam, Cortisone Acetate, Dantrolene.Na, Duloxetine, Fludrocortisone Acetate, Iloperidone, Lorazepam, Nilutamide, Nitisinone, Nitrofurantoin, Oxazepam, Paliperidone, Prasugrel, Probenecid, Rifabutin, Sulfamethoxazole, Ursodiol, Omeprazole, Tenatoprazole, Artemisinin, Danazol, Olmesartan medoxomil, Phenazopyridine, Nitrendipine, Racecadrotil, Fenofibrate, Fluphenazine, Telmisartan, Benzbromarone, Oxethazaine, Mefloquine, Quinacrine, Pimozide, Loxapine succinate, Cyclobenzaprine, Ethopropazine, Promethazine, Clemizole and Pyrimethamine.

Said given drug may further be selected from the group consisting of abacavir sulfate, acebutolol, acecainide, alfuzosin, almotriptan, alprenolol, amantadine, aminoglutethimide, amisulpride, anagrelide, anastrozole, antazoline phosphate, apomorphine, artemisinin, atenolol, atorvastatin calcium, azatadine maleate, bambuterol, Benazepril, benzbromarone, benzthiazide, betamethasone acetate, betamethasone valerate, betaxalol, bezafibrate, bicalutamide, biperiden, bisacodyl, bisoprolol fumarate, bromocriptine mesylate, budesonide, bupropion, buramate, buspirone, camylofine dihydrochloride, capecitabine, carbetapentane citrate, carbinoxamine maleate, carisoprodol, Carvedilol, celecoxib, cetirizine, chlormezanone, cimetidine, citalopram hydrobromide, clemastine fumarate, clemizole, clenbuterol, clidinium bromide, clonidine, clopidogrel sulfate, Clozapine, colchicine, cyclobenzaprine, cyclophosphamide, cyproterone acetate, dabigatran etexilate mesylate, danazol, darifenacin hydrobromide, dasatinib, deflazacort, desvenlafaxine succinate, dexamethasone, dextromethorphan hydrobromide, diacetamate, Dicyclomine, diflorasone diacetate, digitoxin, digoxin, diltiazem, diperodon, diphenylpyraline, Dipyridamole, disopyramide phosphate, domperidone, doxazosin mesylate, doxepin, doxylamine succinate, drospirenone, duloxetine, eletriptan hydrobromide, enalapril maleate, Entacapone, ergonovine maleate, ergotamine tartrate, eszopiclone, ethopropazine, ethoxzolamide, ethynodiol diacetate, etodolac, ezetimibe, famciclovir, famprofazone, febuxostat, fenofibrate, fenspiride, fexofenadine, finasteride, fluconazole, fluoxetine, fluphenazine, fluvoxamine maleate, galantamine, gliclazide, glipizide, griseofulvin, guanfacine, haloperidol, hyoscyamine, idebenone, imatinib, indapamide, indomethacin, Irbesartan, irsogladine maleate, isradipine, itraconazole, ketorolac tromethamine, ketotifen fumarate, labetalol, lamotrigine, letrozole, levamisole, levonorgestrel, linagliptin, lofexidine, Loperamide, losartan, lovastatin, loxapine succinate, mebendazole, mebhydrolin naphthalenesulfonate, mefloquine, megestrol acetate, melphalan, memantine, metaxalone, Methocarbamol, methoxsalen, methsuximide, methylphenidate, methysergide maleate, meticrane, metitepine maleate, metoclopramide, metolazone, metoprolol tartrate, mevastatin, mianserin, mifepristone, milnacipran, mycophenolate mofetil, nadolol, nafronyl oxalate, naftopidil, naloxone, naproxen(+), nateglinide, nefazodone, nefopam, neostigmine bromide, nevirapine, nicergoline, nitrendipine, nizatidine, norethindrone acetate, Norgestimate, noscapine, olanzapine, olmesartan medoxomil, omeprazole, orphenadrine citrate, oxaprozin, oxcarbazepine, oxethazaine, oxybutynin chloride, Paclitaxel, paliperidone, pantoprazole, papaverine, paroxetine, penbutolol sulfate, pentoxifylline, pergolide mesylate, pericyazine, perindopril erbumine, phenacetin, Phenazopyridine, phenytoin sodium, pidotimod, pimozide, pitavastatin calcium, Pranoprofen, prazosin, prednisone, pridinol methanesulfonate, primaquine phosphate, Procarbazine, promethazine, pyrimethamine, quetiapine, quinacrine, quinapril, quinine sulfate, racecadotril, ramelteon, ramipril, ranitidine, ranolazine, rebamipide, repaglinide, Reserpine, riluzole, rimantadine, risperidone, ritonavir, rivastigmine tartrate, rizatriptan benzoate, ropinirole, rosiglitazone maleate, rosuvastatin calcium, roxatidine acetate, sertraline, sildenafil citrate, solifenacin succinate, sotalol, spiperone, sulfasalazine, sulfinpyrazone, sulindac, sulpiride, sumatriptan succinate, tacrine, tacrolimus, tadalafil, tamsulosin hydrchloride, tegaserod maleate, telmisartan, tenatoprazole, tenoxicam, terazosin, terbinafine, thiabendazole, thiothixene, tiapride, timolol maleate, tinidazole, Tolazamide, topotecan, trandolapril, tranilast, trazodone, trihexyphenidyl, trimebutine maleate, trimetazidine dihydrochloride, trimethobenzamide, trimipramine maleate, Triprolidine, tropisetron, trospium chloride, valsartan, venlafaxine, verapamil, vilazodone, Vinpocetine, voriconazole, warfarin, zaleplon, zidovudine [azt], ziprasidone mesylate and zolpidem.

In a particular embodiment, in particular when said given drug is selected from the list of drugs above, said drug-metabolizing gene product is selected from the group consisting of the gene products encoded by the nucleic acid sequences listed in Table 2 below, or is a gene product the amino acid sequence of which is at least 90% identical, in particular at least 91%, 92%, 93%, 94%, 95%, 96%, 97%, 98% or 99% identical to one of the gene products encoded by the nucleic acid sequences listed in Table 2 below.

In a particular embodiment, in particular when said given drug is selected from the list of drugs above, said drug-metabolizing gene product is expressed or secreted by a bacteria selected from the group consisting of the bacteria recited in Table 2 below.

In a particular embodiment, said drug-targeting enzyme is selected from enzymes having oxidation, deamination, isomerization, esterification, condensation, reduction, hydrolysis and/or rearrangement activities. In a particular embodiment, said drug-targeting enzyme is selected from β-glucuronidases, nitroreductases and sulfoxide reductases.

In a particular embodiment, said given drug is dantrolene, clonazepam, and/or nicardipine, and said drug-targeting enzyme is an enzyme having nitro-reduction activity.

In an alternative embodiment, said given drug is risperidone, and said drug-targeting enzyme is an enzyme having hydrolysis activity, in particular an enzyme hydrolysing the isoxazole moiety of risperidone.

In an alternative embodiment, said given drug is sulfasalazine, and said drug-targeting enzyme is an enzyme having azoreduction activity.

In an alternative embodiment, said given drug is digoxin, and said drug-targeting enzyme is cytochrome glycoside reductase, said bacteria expressing said drug-targeting enzyme being preferably *Eggerthella lenta*.

In an alternative embodiment, said given drug is levodopa (L-DOPA), and said drug-targeting enzyme is tyrosine decarboxylase, preferably expressed by *Enterococcus faecalis*, *Enterococcus faecium* and/or *Lactobacillus brevis* and/or dopamine dehydrolase, preferably expressed by *Eggerthella lenta*. In a more particular embodiment, said genetic modification in the DNA sequence encoding said tyrosine decarboxylase induces inactivation of said enzyme, enabling preventing decarboxylation, and thereby inactivation, of L-DOPA by said enzyme, in subjects suffering from Parkinson's disease and treated with levodopa.

In another embodiment, said given drug is levodopa (L-DOPA), and said drug-targeting enzyme is DHPAA synthase, preferably expressed by *Clostridium sporogenes*. In a more particular embodiment, said genetic modification in the DNA sequence encoding DHPAA synthase induces inactivation of said enzyme, enabling preventing deamination of L-DOPA, and thereby transformation of L-DOPA into 3,4-dihydroxyphenylacetaldehyde (DHPAA), and preventing and/or reducing constipation in subjects suffering from Parkinson's disease and treated with levodopa.

In an alternative embodiment, said given drug is gemcitabine, and said drug-targeting enzyme is cytidine deaminase, said bacteria expressing said drug-targeting enzyme being preferably *Escherichia coli* and/or Gamma proteobacteria.

In an alternative embodiment, said given drug is prontosil, and said drug-targeting enzyme is an enzyme converting prontosil into p-aminobenzenesulfonamide by azo-reduction.

In an alternative embodiment, said given drug is selected from sulfasalazine, ipsalazide and balsalazide, and said drug-targeting enzyme is an enzyme converting said drug into 5-aminosalicylic acid.

In an alternative embodiment, said given drug is a non-steroidal anti-inflammatory drug, and said drug-targeting enzyme is a β-glucuronidase.

In a particular embodiment, said compound is L-DOPA, and said modification of the interaction is a modification in the adsorption of L-DOPA by *Helicobacter pylori*, typically by modifying bacterial adhesins from *H. pylori* involved in said adsorption.

In a particular embodiment, said compound is acetaminophen and said modification of the interaction is a modification in the competition between acetaminophen and p-cresol produced by *C. difficile*, typically by modifying DNA sequences involved in the production and/or secretion of p-cresol by *C. difficile*.

The present invention thus also concerns a method of treatment of a subject in need thereof, comprising
  administering a drug to said subject, and
  before, simultaneously with, or after said administration of said drug, administering to said subject a vector encoding enzymes or systems for inducing genetic modifications in a DNA sequence coding for a drug-targeting enzyme expressed or secreted by the bacteria in at least some of the bacteria of said population without introducing a double strand break in the DNA sequence,
  wherein the genetic modification of the DNA sequence coding for the drug-targeting enzyme results in a modification of the drug metabolism in the subject;
  wherein genetic modification does not lead to the direct death of the bacteria.

The present invention thus also concerns a pharmaceutical combination comprising a drug and a vector encoding enzymes or systems for inducing genetic modifications in a DNA sequence coding for a drug-targeting enzyme expressed or secreted by the bacteria in at least some of the bacteria of said population without introducing a double strand break in the DNA sequence, for simultaneous, sequential or separate use in the treatment of a subject.

The invention also concerns a method for increasing the efficacy of a drug treatment in a subject in need thereof, comprising:
  administering a drug to said subject, and
  before, simultaneously with, or after said administration of said drug, administering to said subject a vector encoding enzymes or systems for inducing genetic modifications in a DNA sequence coding for a drug-targeting enzyme expressed or secreted by the bacteria in at least some of the bacteria of said population without introducing a double strand break in the DNA sequence,
  wherein the genetic modification of the DNa sequence coding for the drug-targeting enzyme results in a modification of the drug metabolism in the subject;
  wherein genetic modification does not lead to the direct death of the bacteria.

Lack of Inhibition of Bacterial Growth

Bacteria with the genetic modification can be assessed for any inhibition of bacterial growth by comparison with the same bacteria without the genetic modification either in vitro or in vivo. This is preferably performed by assessing the percentage of bacteria with and without the genetic modification at at least two timepoints and determining that the bacteria with the genetic modification do not have a reduced percentage at the later time point.

Comparison in vitro can be performed by growing the bacteria in solid or liquid culture and determining the percentages of each type of bacteria over time. The percentages can be determined by routine diagnostic procedures including ELISA, PCR, High Resolution Melting, and nucleic acid sequencing.

Comparison in vivo can be performed by collecting samples (e.g., stool or swab) over time and determining the percentages of each type of bacteria over time. The percentages can be determined by routine diagnostic procedures employing immunodetection (e.g. ELISA), nucleic acid amplification (e.g., PCR), High Resolution Melting, and nucleic acid sequencing.

Preferred percentages of bacteria with the genetic modification are at least 70%, 80%, 90%, 95%, 97%, 98%, 99%, 99.9%, 99.99%, and 100%.

Enzymes and Systems for Inducing Modifications

In some embodiments, the genetic modification is made with one or more of the following enzymes and systems.

Cytosine base editors (CBE) and Adenosine base editors (ABE), as described in Rees et al.[9] which is hereby incorporated by reference.

So far there are seven types of DNA base editors described:

Cytosine Base Editor (CBE) that convert C:G into T:A[32]
Adenine Base Editor (ABE) that convert A:T into G:C[33]
Cytosine Guanine Base Editor (CGBE) that convert C:G into G:C[29,30]
Cytosine Adenine Base Editor (CABE) that convert C:G into A:T[31]
Adenine Cytosine Base Editor (ACBE) that convert A:T into C:G[34]
Adenine Thymine Base Editor (ATBE) that convert A:T into T:A[35]
Thymine Adenine Base Editor (TABE) that convert T:A into A:T[36-38]

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY.

ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA. TadA* include TadA-8a-e and TadA-7.10.

Except from base modification enzyme there has been also modifications implemented to base editor to increase editing efficacy, precision and modularity:

the addition of one or two uracil DNA glycosylase inhibitor domain (UGI) to prevent base excision repair mechanism to revert base edition
the addition of Mu-GAM that decrease insertion-deletion rate by inhibiting Non-homologous end joining mechanism in the cell (NHEJ)
the use of nickase active Cas9 (nCas9 D10A) that, by creating nicks on the non-edited strand favors its repair and consequently the fixation of the edited base.
the use of diverse Cas proteins from for example different organisms, mutants with different PAM motifs or different fidelity or different family (e.g. Cas12a).

Non-limiting examples of DNA-based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:
a. A cytosine deaminase (rAPOBEC) and base excision repair proteins (e.g. rXRCC1).[29,41]
b. A rat APOBEC1 variant (R33A) protein and an *E. coli*-derived uracil DNA N-glycosylase (eUNG).[30]

Cytosine Adenine Base Editors (CABE) consist of a Cas9 nickase, a cytidine deaminase (e.g. AID), and a uracil-DNA glycosylase (Ung).[31]

ACBE include a nucleic acid programmable DNA-binding protein and an adenine oxidase.[34]

ATBE consist of a Cas9 nickase and one or more adenosine deaminase or an oxidase domain.[35]

TABE consist of a Cas9 nickase and an adenosine methyltransferase, a thymine al kyltransferase, or an adenosine deaminase domain.[36-38]

Base editor molecules can also consist of two or more of the above listed editor enzymes fused to a Cas protein (e.g. combination of an ABE and CBE). These biomolecules are named dual base editors and enable the editing of two different bases.[39,40]

In a particular embodiment, the genetic modification is made with a Cytosine base editor (CBE) and/or an Adenosine base editor (ABE) as defined above.

Prime editors (PE), as described in Anzalone et al.[10] which is hereby incorporated by reference, consist of a nCas9 fused to a reverse transcriptase used in combination with a prime editing RNA (pegRNA; a guide RNA that includes a template region for reverse transcription).

Prime Editing allows introduction of insertions, deletions (indels), and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:
a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)
a prime editing guide RNA (pegRNA)

To favor editing, the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3inv, PE2, PE3, PE3b.

Cas9 Retron preciSe Parallel Editing via homologY ('CRISPEY'), a retron RNA fused to the sgRNA and expressed together with Cas9 and the retron proteins including at least the reverse transcriptase[11].

The SCRIBE strategy: a retron system expressed in combination with a recombinase promoting the recombination of single stranded DNA, also known as single stranded annealing proteins (SSAPs)[12]. Such recombinases include but are not limited to phage recombinases such as lambda red, recET, Sak, Sak4, and newly described SSAPs described in Wannier et al[13] which is hereby incorporated by reference.

The targetron system based on group II introns described in Karberg et al.[14], which is hereby incorporated by reference, and which has been adapted to many bacterial species.

Other retron based gene targeting approaches are described in Simon et al.[15] which is hereby incorporated by reference.

CRISPR-Cas. The CRISPR system contains two distinct elements, i.e. i) an endonuclease, in this case the CRISPR associated nuclease (Cas or "CRISPR associated protein") and ii) a guide RNA. Depending on the type of CRISPR system, the guide RNA may be in the form of a chimeric RNA which consists of the combination of a CRISPR (crRNA) bacterial RNA and a tracrRNA (trans-activating RNA CRISPR)[16]. The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix.

The CRISPR system includes two main classes depending on the nuclease mechanism of action:
  Class 1 is made of multi-subunit effector complexes and includes type I, III and IV
  Class 2 is made of single-unit effector modules, like Cas9 nuclease, and includes type II (II-A,II-B,II-C,II-C variant), V (V-A,V-B,V-C,V-D,V-E,V-U1,V-U2,V-U3,V-U4,V-U5) and VI (VI-A,VI-B1,VI-B2,VI-C,VI-D)

The sequence of interest according to the present invention preferably comprises a nucleic acid sequence encoding Cas protein. A variety of CRISPR enzymes are available for use as a sequence of interest on the vector according to the present invention. In some embodiments, the CRISPR enzyme is a Type II CRISPR enzyme, a Type II-A or Type II-B CRISPR enzyme. In another embodiment, the CRISPR enzyme is a Type I CRISPR enzyme or a Type III CRISPR enzyme. In some embodiments, the CRISPR enzyme catalyzes DNA modification. In some other embodiments, the CRISPR enzyme catalyzes RNA modification. For instance, Cas13-deaminase fusions have been used for RNA base editing thus modifying RNA[17]. In one embodiment, the CRISPR enzymes may be coupled to a guide RNA or single guide RNA (sgRNA). In certain embodiments, the guide RNA or sgRNA targets a DNA sequence or gene selected from the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general and a gene causing a deleterious effect to the host. Preferably, the CRISPR enzyme does not make a double strand break. In some embodiments, the CRISPR enzyme makes a single strand break or nicks. In some embodiments, the CRISPR enzyme does not make any break in the DNA or RNA. In one embodiment, a Cas13-deaminase fusion is used to base edit an RNA.

The sequence of interest may comprise a nucleic acid sequence encoding a guide RNA or sgRNA to guide the Cas protein endogenous to the targeted bacteria, alone or in combination with a Cas protein and/or a guide RNA encoded by the vector.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, homologues thereof, orthologues thereof, variants thereof, or modified versions thereof. In some embodiments, the CRISPR enzyme cleaves both strands of the target nucleic acid at the Protospacer Adjacent Motif (PAM) site.

In various embodiments, the nucleic acid of interest encodes fusion proteins comprising a Cas9 (e.g., a Cas9 nickase) domain and a deaminase domain. In some embodiments, the fusion protein comprises Cas9 and a cytosine deaminase enzyme, such as APOBEC enzymes, or adenosine deaminase enzymes, such as ADAT enzymes, for example as disclosed in U.S. Patent Publ. 2015/0166980, which is hereby incorporated by reference. In one embodiment, the deaminase is an ACF1/ASE deaminase.

In various embodiments, the APOBEC deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In various embodiments, the fusion protein comprises a Cas9 domain, a cytosine deaminase domain, and a uracil glycosylase inhibitor (UGI) domain.

In one embodiment, the deaminase is an adenosine deaminase that deaminate adenosine in DNA, for example as disclosed in U.S. Pat. No. 10,113,163, which is hereby incorporated by reference. In some embodiments, the fusion proteins further comprise an inhibitor of base repair, such as, a nuclease dead inosine specific nuclease (dISN), for example as disclosed in U.S. Pat. No. 10,113,163. In various embodiments, the nucleic acid of interest encodes fusion proteins comprising a catalytically impaired Cas9 endonuclease fused to an engineered reverse transcriptase, programmed with a prime editing guide RNA (pegRNA) that both specifies the target site and encodes the desired edit, for example as described in Anzalone et al.[10], which is hereby incorporated by reference.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s). Preferably, the Cas9 is a dCas9 (dead-Cas9) or nCas9 (nickase Cas9) lacking double strand DNA cleavage activity.

The sequence encoding Cas9 (the entire protein or a fragment thereof) as used in the context of the invention can be obtained from any known Cas9 protein[18-20]. Examples of Cas9 proteins useful in the present invention include, but are not limited to, Cas9 proteins of *Streptococcus pyogenes* (SpCas9), *Streptococcus* thermophiles (St1Cas9, St3Cas9),

*Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the invention can be obtained from any known Cpf1 (Cas12a) protein[18,19]. Examples of Cpf1(Cas12a) proteins useful in the present invention include, but are not limited to, Cpf1(Cas12a) proteins of *Acidaminococcus* sp, Lachnospiraceae bacteriu and *Francisella novicida*.

The sequence encoding Cas13a (the entire protein or a fragment thereof) as used in the context of the invention can be obtained from any known Cas13a (C2c2) protein[21]. Examples of Cas13a (C2c2) proteins useful in the present invention include, but are not limited to, Cas13a (C2c2) proteins of *Leptotrichia wadei* (LwaCas13a).

The sequence encoding Cas13d (the entire protein or a fragment thereof) as used in the context of the invention can be obtained from any known Cas13d protein (Yan et al. (2018) *Mol Cell* 70(2):327-339). Examples of Cas13d proteins useful in the present invention include, but are not limited to, Cas13d proteins of *Eubacterium siraeum* and *Ruminococcus* sp.

In some embodiments, other programmable nucleases can be used. These include an engineered TALEN (Transcription Activator-Like Effector Nuclease) and variants, engineered zinc finger nuclease (ZFN) variants, natural, evolved or engineered meganuclease or recombinase variants, and any combination or hybrids of programmable nucleases. Thus, the programmable nucleases provided herein may be used to selectively modify DNA encoding a DNA sequence or gene of interest such as, for example, a toxin gene, a virulence factor gene, an antibiotic resistance gene, a remodeling gene or a modulatory gene (cf. WO2014124226 and US2015/0064138).

In some embodiments, the genetic modification is made at the RNA level. RNA base editing is based on the same principle as DNA base editing: an enzyme catalyzing the conversion of a RNA base into another must be brought close to the target base to perform its conversion locally. In one embodiment, the enzyme used for RNA editing is an adenosine deaminase from ADAR family that converts Adenosine into Inosine in dsRNA structure. Several seminal studies used this specificity for dsRNA and fused the ADAR deaminase domain ($ADAR_{DD}$) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to a hyperactive mutant of ADAR2 deaminase domain ($ADAR2_{DD}$-E488Q for REPAIRv1 and $ADAR2_{DD}$-E488Q-T375G for REPAIRv2) Cox et al improved specificity and efficiency compare to previous RNA editing strategies.

Non-limiting examples of RNA based editor proteins include REPAIRv1, REPAIRv2.

Vectors for Inducing Modifications

In various embodiments, one or more of the following vectors can be used to introduce the exogenous enzyme that results in a genetic modification:

Engineered phages
Engineered bacteria
Plasmid (e.g., a conjugative plasmid capable of transfer into a host cell), phage, phagemid or prophage.
Each vector may be as described above, e.g., a phage capable of infecting a host cell or conjugative plasmid capable of introduction into a host cell, which can be introduced either by a phage particle (engineered or wild-type phage) via injection or by a donor bacteria via conjugation. In an example, the vectors are in combination with an antibiotic agent (e.g., a beta-lactam antibiotic) and/or with any other agent.

A bacteriophage for modifying a naturally occurring bacteria in situ comprising a nucleic acid encoding a gene editing enzyme/system for transformation of a target bacteria in a mixed bacterial population wherein said gene editing enzyme/system modifies the genome of said target bacteria, but does not lead to the death of the target bacteria.

The invention encompasses the use of these vectors wherein the gene editing enzyme/system targets a DNA sequence or gene within the target bacteria encoding a protein which is directly or indirectly responsible for a disease or disorder.

In a particular embodiment, said vector does not replicate in the targeted bacteria.

Origin of Replication

In preferred embodiments the DNA in the vector will comprise an origin of replication for the targeted bacteria. Origins of replication known in the art have been identified from species-specific plasmid DNAs (e.g. ColE1, RI, pT181, pSC101, pMB1, R6K, RK2, p15a and the like), from bacterial virus (e.g. φX174, M13, F1 and P4) and from bacterial chromosomal origins of replication (e.g. oriC).

In one embodiment, the vector according to the invention comprises a bacterial origin of replication that is functional in the targeted bacteria.

Alternatively, the vector according to the invention does not comprise any functional bacterial origin of replication or contain an origin of replication that is inactive in the targeted bacteria. Thus, the vector of the invention cannot replicate by itself once it has been introduced into a bacterium by the bacterial virus particle.

In one embodiment, the origin of replication on the vector to be packaged is inactive in the targeted bacteria, meaning that this origin of replication is not functional in the bacteria targeted by the bacterial virus particles, thus preventing unwanted vector replication.

In one embodiment, the vector comprises a bacterial origin of replication that is functional in the bacteria used for the production of the bacterial virus particles.

Bacteria-Specific Origins of Replication

Plasmid replication depends on host enzymes and on plasmid-controlled cis and trans determinants. For example, some plasmids have determinants that are recognized in almost all gram-negative bacteria and act correctly in each host during replication initiation and regulation. Other plasmids possess this ability only in some bacteria (Kues, U and Stahl, U 1989 Microbiol Rev 53:491-516).

Plasmids are replicated by three general mechanisms, namely theta type, strand displacement, and rolling circle (reviewed by Del Solar et al. 1998 Microhio and Molec Biol. Rev 62:434-464) that start at the origin of replication. This replication origins contain sites that are required for interactions of plasmid and/or host encoded proteins.

Origins of replication used on the vector of this invention may be moderate copy number, such as ColE1 ori from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication is selected in the group consisting of ColE1, pMB1 and variants (pBR322, pET, pUC, etc), p15a, ColA, ColE2, pOSAK, pSC101, R6K, IncW(pSa etc), IncF1I, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

More preferably, the bacterial origin of replication is an *E. coli* origin of replication selected in the group consisting of ColE1, pMB1 and variants (pBR322, pET, pUC, etc), p15a, ColA, ColE2, pOSAK, pSC101, R6K, IncW (pSa etc), IncF1I, pT181, P1, F IncP, IncC, IncJ, IncN, IncP1, IncP4, IncQ, IncH11, RSF1010, CloDF13, NTP16, R1, f5, pPS10.

More preferably, the bacterial origin of replication is selected in the group consisting of pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

Even more preferably, the bacterial origins of replication are ColE1 and p15a.

In one embodiment, the bacterial origin of replication is functional in *Propionibacterium* and *Cutibacterium* more specifically in *Propionibacterium freudenreichii* and *Cutibacterium acnes* and is selected from the group consisting of pLME108, pLME106, p545, pRGO1, pZGX01, pPG01, pYS1, FRJS12-3, FRJS25-1, pIMPLE-HL096PA1, A_15_1_R1.

Phage Origin of Replication

The vector according to the invention may comprise a phage replication origin which can initiate, with complementation in cis or in trans of a complete or modified phage genome, the replication of the payload for later encapsulation into the different capsids.

The phage origin can also be engineered to act as a bacterial origin of replication without the need to package any phage particles.

A phage origin of replication comprised in the payload of the invention can be any origin of replication found in a phage.

Preferably, the phage origin of replication can be the wild-type or non-wildtype sequence of the M13, f1, φX174, P4, Lambda, P2, 186, Lambda-like, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 PI-like, P2-like, P22, P22-like, N15 and N15-like bacteriophages.

More preferably, the phage origin of replication is selected in the group consisting of phage origins of replication of M13, f1, φX174, P4, and Lambda.

In a particular embodiment, the phage origin of replication is the P4 origin of replication.

In a particular embodiment, the phage origin of replication is from *Propionibacterium* phages: BW-like phages such as Doucette, B22, E6, G4, BV-like phages such as Anatole, E1, B3, BX-like phages such as PFR1 and PFR2, filamentous B5 phage, BU-like phages (*Cutibacterium acnes* phages).

Conditional Origin of Replication

In a particular embodiment, the vector comprises a conditional origin of replication which is inactive in the targeted bacteria but is active in a donor bacterial cell.

In the context of the invention, a "conditional origin of replication" refers to an origin of replication whose functionality may be controlled by the presence of a specific molecule.

In a particular embodiment, the conditional origin of replication is an origin of replication, the replication of which depends upon the presence of one or more given protein, peptid, RNA, nucleic acid, molecule or any combination thereof.

In a particular embodiment, the replication of said origin of replication may further depend on a process, such as transcription, to activate said replication.

In the context of the invention, said conditional origin of replication is inactive in the targeted bacteria because of the absence of said given protein, peptid, RNA, nucleic acid, molecule or any combination thereof in said targeted bacteria.

In a particular embodiment, said conditional origin of replication is active in said donor bacterial cell because said donor bacterial cell expresses said given protein, peptid, RNA, nucleic acid, molecule or any combination thereof. In a particular embodiment, said protein, peptid, RNA nucleic acid, molecule or any combination thereof is expressed in trans in said donor bacterial cell.

By "in trans" is meant herein that said protein, peptid, RNA, nucleic acid, molecule or any combination thereof is not encoded on the same nucleic acid molecule as the one comprising the origin of replication. In a particular embodiment, said protein, peptid, RNA, nucleic acid, molecule or any combination thereof is encoded on a chromosome or on a vector, in particular a plasmid. In a particular embodiment, said vector comprises an antibiotic resistance marker. In an alternative embodiment, said vector is devoid of antibiotic resistance marker.

Since said conditional origin of replication is inactive in the targeted bacteria because of the absence of said given protein, peptid, RNA, nucleic acid, molecule or any combination thereof in said targeted bacteria, said conditional origin of replication may be selected depending on the specific bacteria to be targeted.

The conditional origin of replication disclosed herein may originate from plasmids, bacteriophages or PICIs which preferably share the following characteristics: they contain in their origin of replication repeat sequences, or iterons, and they code for at least one protein interacting with said origin of replication (i.e. Rep, protein O, protein P, pri) which is specific to them.

By way of example, mention may be made of the conditional replication systems of the following plasmids and bacteriophages: RK2, R1, pSC101, F, Rts1, RSF1010, P1, P4, lambda, phi82, phi80.

In a particular embodiment, said conditional origin of replication is selected from the group consisting of the R6Kλ DNA replication origin and derivatives thereof, the IncPα oriV origin of replication and derivatives thereof, ColE1 origins of replication modified to be under an inducible promoter, and origins of replication from phage-inducible chromosomal islands (PICIs) and derivatives thereof.

In a particular embodiment, said conditional origin of replication is an origin of replication present in less than 50%, or less than 40%, less than 30%, less than 20%, less than 10% or less than 5% of the bacteria of the host microbiome.

In another particular embodiment, said conditional origin of replication comprises or consists of a sequence less than 80% identical, in particular less than 70%, less than 60%, less than 50%, less than 40%, less than 30%, less than 20%, less than 10%, less than 5% or less than 1% identical to the sequences of the origins of replication of the bacteria of the host microbiome, in particular of the bacteria representing more than 50%, more particularly more than 60%, more than 70%, more than 80%, more than 90% or more than 95% of the host microbiome.

As used herein, the term "phage-inducible chromosomal islands" or "PICIs" refers to mobile genetic elements having a conserved gene organization, and encode a pair of divergent regulatory genes, including a PICI master repressor. Typically, in Gram-positive bacteria, left of rpr, and transcribed in the same direction, PICIs encode a small set of genes including an integrase (int) gene; right of rpr, and transcribed in the opposite direction, the PICIs encode an excision function (xis), and a replication module consisting of a primase homolog (pri) and optionally a replication initiator (rep), which are sometimes fused, followed by a replication origin (ori), next to these genes, and also transcribed in the same direction, PICIs encode genes involved in phage interference, and optionally, a terminase small subunit homolog (terS).

In a particular embodiment, said conditional origin of replication is an origin of replication derived from phage-inducible chromosomal islands (PICIs).

A particular conditional origin of replication has indeed been derived from PICIs.

It was shown that it is possible to derive novel conditionally replicative vectors, in particular based on the primase-helicase and origin of replication from PICIs. These origins may be relatively rare in target strains, and more advantageously the primase-ori pair may be unique for each PICI, significantly reducing the possibility of undesired recombination or payload spread events. They can further be modified to further limit recombination chances and remove restriction sites to bypass target bacteria defense systems.

In a particular embodiment, said conditional origin of replication is derived from the origin of replication from the PICI of the *Escherichia coli* strain CFT073, disclosed in Fillol-Salom et al. (2018) *The ISME Journal* 12:2114-2128.

In a particular embodiment, said conditional origin of replication is the primase ori from the PICI of the *Escherichia coli* strain CFT073, typically of sequence SEQ ID NO: 12.

In another particular embodiment, said conditional origin of replication is the primase ori from the PICI of the *Escherichia coli* strain CFT073, devoid of at least 1, at least 2, at least 3, at least 4, at least 5, at least 6, at least 7, at least 8, at least 9, at least 10, at least 11, at least 12, at least 13, at least 14, at least 15 or at least 16 restriction site(s) selected from the group consisting of GAAABCC, GCCGGC, RCCGGY, GCNGC, TWCANNNNNNTGG (SEQ ID NO: 13), TGGCCA, ACCYAC, YGGCCR, AGACC, GCWGC, GGGANGC, GKAGATD, GCCGGYYD, GGCYAC, RGCCGGYYD, and VGCCGGYBD.

In a particular embodiment, said conditional origin of replication is the primase ori from the PICI of the *Escherichia coli* strain CFT073, devoid of the restriction site GAAABCC. Preferably, said conditional origin of replication is of sequence SEQ ID NO: 7.

In another particular embodiment, said conditional origin of replication is the primase ori from the PICI of the *Escherichia coli* strain CFT073 devoid of the restriction sites GAAABCC, GCCGGC, RCCGGY, GCNGC, TWCANNNNNNTGG (SEQ ID NO: 13), TGGCCA, ACCYAC, YGGCCR, AGACC, GCWGC, GGGANGC, GKAGATD, GCCGGYYD, GGCYAC, RGCCGGYYD, and VGCCGGYBD. Preferably, said conditional origin of replication is of sequence SEQ ID NO: 8.

In a particular embodiment, wherein said origin of replication is derived from phage-inducible chromosomal islands (PICIs), said conditional origin of replication is active in said donor bacterial cell because said donor bacterial cell expresses a rep protein, in particular a primase-helicase, in particular a primase-helicase of sequence SEQ ID NO: 14, typically encoded by a nucleic acid comprising or consisting of the sequence SEQ ID NO: 15.

It was demonstrated that these specific conditional origins of replication were particularly compatible with lambda-based packaging, leading to sufficiently high titers ($>10^{10}$/mL) required for microbiota-related applications.

In a particular embodiment, when said vector is a phagemid, said origin of replication may be derived from a microorganism which is different from the one that is used to encode the structural elements of the capsid packaging said phagemid.

By "donor bacterial cell" is meant herein a bacterium that is capable of hosting a vector as defined above, of producing a vector as defined above and/or which is capable of transferring said vector as defined above to another bacterium. In a particular embodiment, said vector may be a phagemid, and said donor bacterial cell may then be a bacterial cell able to produce said phagemid, more particularly in the form of a packaged phagemid. In an alternative embodiment, said vector may be a plasmid, more particularly a conjugative plasmid, and said donor bacterial cell may then be a bacterium that is capable of transferring said conjugative plasmid to another bacterium, in particular by conjugation.

Preferably, said donor bacterial cell stably comprises said vector and is able to replicate said vector.

In a particular embodiment, when the conditional origin of replication of said vector is an origin of replication, the replication of which depends upon the presence of a given protein, peptid, nucleic acid, RNA, molecule or any combination thereof, said donor bacterial cell expresses said protein, peptid, nucleic acid, RNA, molecule or any combination thereof. Preferably, said protein, peptid, nucleic acid, RNA, molecule or any combination thereof is expressed in trans, as defined above.

In a particular embodiment, said donor bacterial cell stably comprises a nucleic acid encoding said protein, peptid, nucleic acid, RNA, molecule or any combination thereof.

In a particular embodiment, when said origin of replication is derived from phage-inducible chromosomal islands (PICIs), said conditional origin of replication is active in said donor bacterial cell because said donor bacterial cell expresses a rep protein, in particular a primase-helicase, in particular a primase-helicase of sequence SEQ ID NO: 14.

In a particular embodiment, said donor bacterial cell stably comprises a nucleic acid encoding said rep protein, in particular said primase-helicase, said nucleic acid typically comprising or consisting of the sequence SEQ ID NO: 15.

In a particular embodiment, said donor bacterial cell is a production cell line, in particular a cell line producing packaged phagemids including the vector of the invention.

Generation of packaged phagemids and bacteriophage particles by production cell lines are routine techniques well-known to one skilled in the art. In an embodiment, a satellite phage and/or helper phage may be used to promote the packaging of the vector in the delivery vehicles disclosed herein. Helper phages provide functions in trans and are well known to the man skilled in the art. The helper phage comprises all the genes coding for the structural and functional proteins that are indispensable for the phagemid to be packaged, (i.e. the helper phage provides all the necessary gene products for the assembly of the delivery vehicle). The helper phage may contain a defective origin of replication or packaging signal, or completely lack the latter, and hence it is incapable of self-packaging, thus only bacterial delivery particles carrying the vector or plasmid will be produced. Helper phages may be chosen so that they cannot induce lysis of the bacterial cells used for the delivery particle production. One skilled in the art would understand that some bacteriophages are defective and need a helper phage for payload packaging. Thus, depending on the bacteriophage chosen to prepare the bacterial delivery particles, the person skilled in the art would know if a helper phage is required. Sequences coding for one or more proteins or regulatory processes necessary for the assembly or production of packaged payloads may be supplied in trans. For example, STF, gpJ and gpH proteins may be provided in a vector or plasmid under the control of an inducible promoter or expressed constitutively. In this case, the phage wild-type sequence may or not contain a deletion of the gene or sequence supplied in trans. Additionally, chimeric or modified phage sequences encoding a new function, like an engineered STF, gpJ or gpH protein, may be directly inserted into the desired position in the genome of the helper phage, hence bypassing the necessity of providing the modified sequence in trans. Methods for both supplying a sequence or protein in trans in the form of a vector or plasmid, as well as methods to generate direct genomic insertions, modifications and mutations are well known to those skilled in the art.

Delivery Vehicle Incapable of Self-Reproduction

In a particular embodiment, the delivery vehicle, in particular the bacteriophage, bacterial virus particle or packaged phagemid, comprising the vector of the invention is incapable of self-reproduction.

In the context of the present invention, "self-reproduction" is different from "self-replication", "self-replication" referring to the capability of replicating a nucleic acid, whereas "self-reproduction" refers to the capability of having a progeny, in particular of producing new delivery vehicles, said delivery vehicles being either produced empty or with a nucleic acid of interest packaged.

By "delivery vehicle incapable of self-reproduction" is meant herein that at least one, several or all functional gene(s) necessary to produce said delivery vehicle is(are) absent from said delivery vehicle (and from said vector included in said delivery vehicle). In a preferred embodiment, said at least one, several or all functional gene(s) necessary to produce said delivery vehicle is(are) present in the donor cell as defined above, preferably in a plasmid, in the chromosome or in a helper phage present in the donor cell as defined above, enabling the production of said delivery vehicle in said donor cell.

In the context of the invention, said functional gene necessary to produce delivery vehicle may be absent through (i) the absence of the corresponding gene or (ii) the presence of the corresponding gene but in a non-functional form.

In an embodiment, the sequence of said gene necessary to produce said delivery vehicle is absent from said delivery vehicle. In a preferred embodiment, the sequence of said gene necessary to produce said delivery vehicle has been replaced by a nucleic acid sequence of interest, in particular by a nucleic acid sequence encoding enzymes or systems for inducing genetic modifications, as defined above.

Alternatively, said gene necessary to produce said delivery vehicle is present in said delivery vehicle in a non-functional form, for example in a mutant non-functional form, or in a non-expressible form, for example with deleted or mutated non-functional regulators. In a preferred embodiment, said gene necessary to produce said delivery vehicle is present in said delivery vehicle in a mutated form which renders it non-functional in the target cell, while remaining functional in the donor cell.

In the context of the invention, genes necessary to produce said delivery vehicle encompass any coding or non-coding nucleic acid required for the production of said delivery vehicle.

Examples of genes necessary to produce said delivery vehicle include genes encoding phage structural proteins; phage genes involved in the control of genetic expression; phage genes involved in transcription and/or translation regulation; phage genes involved in phage DNA replication; phage genes involved in production of phage proteins; phage genes involved in phage proteins folding; phage genes involved in phage DNA packaging; and phage genes encoding proteins involved in bacterial cell lysis.

Sequence of Interest Under the Control of the Promoter

The vector can comprise a sequence of interest under the control of at least one promoter.

In one embodiment, the sequence of interest is a programmable nuclease circuit to be delivered to the targeted bacteria. This programmable nuclease circuit may be able to mediate in vivo sequence-specific elimination of bacteria that contain a target gene of interest (e.g. a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases. Thus, the engineered autonomously distributed circuits provided herein may be used to selectively modify DNA encoding a gene of interest such as, for example, a toxin gene, a virulence factor gene, an antibiotic resistance gene, a remodeling gene or a modulatory gene (cf. WO2014124226 and US2015/0064138).

Other sequences of interest, preferably programmable, can be added to the vector so as to be delivered to targeted bacteria.

Preferably, the sequence of interest circuit added to the payload does not lead to bacteria death. For example, the sequence of interest may encode reporter genes leading to a luminescence or fluorescence signal. Alternatively, the sequence of interest may comprise proteins and enzymes achieving a useful function such as modifying the metabolism of the bacteria, the composition of its environment or affecting the host. More specifically the sequence of interest might be an antigen triggering a host immune response. The specific antigen can be released in the environment after induction of the lysis of the target cell or can be secreted by the target cell, for example, as described in Costa et al[22] and Anné et al[23].

In a particular embodiment, the nucleic acid sequence of interest is selected from the group consisting of a Cas nuclease, a Cas9 nuclease, a guide RNA, a single guide RNA (sgRNA), a CRISPR locus, a gene expressing an enzyme such as a nuclease or a kinase, a TALEN, a ZFN, a meganuclease, a recombinase, a bacterial receptor, a membrane protein, a structural protein, a secreted protein, a gene expressing resistance to an antibiotic or to a drug in general, a gene expressing a toxic protein or a toxic factor and a gene expressing a virulence protein or a virulence factor, a bacterial secretory protein or transporter, a bacterial pore or any of their combination. These proteins can also be modified or engineered to include extra features, like the addition or removal of a function (e.g. dCas9), the addition of a secretion signal to a protein not normally secreted, the addition of an exogenous peptide in a loop as non-limiting examples.

Targeted Bacteria

The bacteria targeted by the vectors, delivery particles, bacteriophages, donor cells, bacterial virus particles or packaged phagemids can be any bacteria present in a mammal organism, a plant or in the environment. It can be any commensal, symbiotic or pathogenic bacteria of the microbiota or microbiome.

A microbiome may comprise a variety of endogenous bacterial species, any of which may be targeted in accordance with the present disclosure. In some embodiments, the genus and/or species of targeted endogenous bacterial cells may depend on the type of bacteriophages being used for preparing the bacterial virus particles. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells include, without limitation, cells from bacteria of the genus *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., Erysipelothrix spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Brucelia* spp., *Campylobacter* spp., *Chlamydophilia* spp., *Cutibacterium* spp., *Propionibacterium* spp., *Gardnerella* spp., *Ehrlichia* spp., *Haemophilus* spp., *Leptospira* spp., *Listeria* spp., *Mycoplasma* spp., *Nocardia* spp., *Rickettsia* spp., *Ureaplasma* spp., *Lactobacillus* spp. and a mixture thereof.

Thus, vectors, delivery particles, bacteriophages, bacterial virus particles or packaged phagemids may target (e.g., specifically target) a bacterial cell from any one or more of the foregoing genus of bacteria to specifically deliver the payload according to the invention.

Preferably, the targeted bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., *Listeria* spp., *Cutibacterium* spp., *Propionibacterium* spp., *Fusobacterium* spp., *Porphyromonas* spp. and *Gardnerella* spp.

In some embodiments, bacterial cells of the present invention are anaerobic bacterial cells (e.g., cells that do not require oxygen for growth). Anaerobic bacterial cells include facultative anaerobic cells such as but not limited to *Escherichia coli, Shewanella oneidensi, Gardnerella vaginalis* and *Listeria*. Anaerobic bacterial cells also include obligate anaerobic cells such as, for example, *Bacteroides, Clostridium, Cutibacterium, Propionibacterium, Fusobacterium* and *Porphyromonas* species. In humans, anaerobic bacteria are most commonly found in the gastrointestinal tract. In some particular embodiment, the targeted bacteria are thus bacteria most commonly found in the gastrointestinal tract. Bacteriophages used for preparing the bacterial virus particles, and then the bacterial virus particles, may target (e.g., to specifically target) anaerobic bacterial cells according to their specific spectra known by the person skilled in the art to specifically deliver the payload.

In some embodiments, the targeted bacterial cells are, without limitation, *Bacteroides faecis, Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphiococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Streptomyces phaechromogenes, Streptomyces ghanaenis, Klebsiella pneumoniae, Enterobacter cloacae, Enterobacter aerogenes, Serratia marcescens, Morganella morganii, Citrobacter freundii, Propionibacterium freudenreichii, Pseudomonas aerigunosa, Parvimonas micra, Prevotella intermedia, Fusobacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes* (formerly *Propionibacterium acnes*), *Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexnerii, Shigella dysenteriae, Staphylococcus saprophyticus, Streptococcus pneumoniae, Streptococcus pyogenes, Gardnerella vaginalis, Streptococcus viridans,*

*Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas aerigunosa*, and a mixture thereof, preferably the bacteria of interest are selected from the group consisting of *Escherichia coli, Enterococcus faecium, Staphylococcus aureus, Klebsiella pneumoniae, Acinetobacter baumanii, Pseudomonas aeruginosa, Enterobacter cloacae*, and *Enterobacter aerogenes*, and a mixture thereof.

In some embodiments, the targeted bacterial cells are, without limitation, *Anaerotruncus, Acetanaerobacterium, Acetitomaculum, Acetivibrio, Anaerococcus, Anaerofilum, Anaerosinus, Anaerostipes, Anaerovorax, Butyrivibrio, Clostridium, Capracoccus, Dehalobacter, Dialister, Dorea, Enterococcus, Ethanoligenens, Faecalibacterium, Fusobacterium, Gracilibacter, Guggenheimella, Hespellia, Lachnobacterium, Lachnospira, Lactobacillus, Leuconostoc, Megamonas, Moryella, Mitsuokella, Oribacterium, Oxobacter, Papillibacter, Proprionispira, Pseudobutyrivibrio, Pseudoramibacter, Roseburia, Ruminococcus, Sarcina, Seinonella, Shuttleworthia, Sporobacter, Sporobacterium, Streptococcus, Subdoligranulum, Syntrophococcus, Thermobacillus, Turibacter, Weisella, Clostridium, Bacteroides, Ruminococcus, Faecalibacterium, Treponema, Phascolarctobacterium, Megasphaera, Faecalibacterium, Bifidobacterium, Lactobacillus, Sutterella*, and/or *Prevotella*.

In other embodiments, the targeted bacteria cells are, without limitation, *Achromobacter xylosoxidans, Acidaminococcus fermentans, Acidaminococcus* intestini, *Acidaminococcus* sp., *Acinetobacter baumannii, Acinetobacter junii, Acinetobacter Iwoffii, Actinobacillus capsulatus, Actinomyces naeslundii, Actinomyces neuii, Actinomyces odontolyticus, Actinomyces radingae, Adlercreutzia equolifaciens, Aeromicrobium massiliense, Aggregatibacter actinomycetemcomitans, Akkermansia muciniphila, Aliagarivorans marinus, Alistipes finegoldii, Alistipes indistinctus, Alistipes inops, Alistipes onderdonkii, Alistipes putredinis, Alistipes senegalensis, Alistipes shahii, Alistipes timonensis, Alloscardovia omnicolens, Anaerobacter polyendosporus, Anaerobaculum hydrogeniformans, Anaerococcus hydrogenalis, Anaerococcus prevotii, Anaerococcus senegalensis, Anaerofustis stercorihominis, Anaerostipes caccae, Anaerostipes hadrus, Anaerotruncus colihominis, Aneurinibacillus aneurinilyticus, Bacillus licheniformis, Bacillus massilioanorexius, Bacillus massiliosenegalensis, Bacillus simplex, Bacillus smithii, Bacillus subtilis, Bacillus thuringiensis, Bacillus timonensis, Bacteroides xylanisolvens, Bacteroides acidifaciens, Bacteroides caccae, Bacteroides capillosus, Bacteroides cellulosilyticus, Bacteroides clarus, Bacteroides coprocola, Bacteroides coprophilus, Bacteroides dorei, Bacteroides eggerthii, Bacteroides faecis, Bacteroides finegoldii, Bacteroides fluxus, Bacteroides fragilis, Bacteroides gallinarum, Bacteroides intestinalis, Bacteroides nordii, Bacteroides oleiciplenus, Bacteroides ovatus, Bacteroides pectinophilus, Bacteroides plebeius, Bacteroides salanitronis, Bacteroides salyersiae, Bacteroides* sp., *Bacteroides stercoris, Bacteroides thetaiotaomicron, Bacteroides uniformis, Bacteroides vulgatus, Bacteroides xylanisolvens, Bacteroidespectinophilus* ATCC, *Barnesiella intestinihominis, Bavariicoccus seileri, Bifidobacterium adolescentis, Bifidobacterium angulatum, Bifidobacterium animalis, Bifidobacterium bifidum, Bifidobacterium breve, Bifidobacterium catenulatum, Bifidobacterium dentium, Bifidobacterium gallicum, Bifidobacterium longum, Bifidobacterium pseudocatenulatum, Bifidobacterium stercoris, Bilophila wadsworthia, Blautia faecis, Blautia hansenii, Blautia hydrogenotrophica, Blautia luti, Blautia obeum, Blautia producta, Blautia wexlerae, Brachymonas chironomi, Brevibacterium senegalense, Bryantella formatexigens*, butyrate-producing bacterium, *Butyricicoccus pullicaecorum, Butyricimonas virosa, Butyrivibrio crossotus, Butyrivibrio fibrisolvens, Caldicoprobacter faecalis, Campylobacter concisus, Campylobacter jejuni, Campylobacter upsaliensis, Catenibacterium mitsuokai, Cedecea davisae, Cellulomonas massiliensis, Cetobacterium somerae, Citrobacter braakii, Citrobacter freundii, Citrobacter pasteurii, Citrobacter* sp., *Citrobacter youngae, Cloacibacillus evryensis, Clostridiales bacterium, Clostridioides difficile, Clostridium asparagiforme, Clostridium bartlettii, Clostridium boliviensis, Clostridium bolteae, Clostridium hathewayi, Clostridium hiranonis, Clostridium hylemonae, Clostridium leptum, Clostridium methylpentosum, Clostridium nexile, Clostridium orbiscindens, Clostridium ramosum, Clostridium scindens, Clostridium sp, Clostridium* sp., *Clostridium spiroforme, Clostridium sporogenes, Clostridium symbiosum, Collinsella aerofaciens, Collinsella intestinalis, Collinsella stercoris, Collinsella tanakaei, Coprobacillus cateniformis, Coprobacter fastidiosus, Coprococcus catus, Coprococcus comes, Coprococcus eutactus, Corynebacterium ammoniagenes, Corynebacterium amycolatum, Corynebacterium pseudodiphtheriticum, Cutibacterium acnes, Dermabacter hominis, Desulfitobacterium hafniense, Desulfovibrio fairfieldensis, Desulfovibrio piger, Dialister succinatiphilus, Dielma fastidiosa, Dorea formicigenerans, Dorea longicatena, Dysgonomonas capnocytophagoides, Dysgonomonas gadei, Dysgonomonas mossii, Edwardsiella tarda, Eggerthella lenta, Eisenbergiella tayi, Enorma massiliensis, Enterobacter aerogenes, Enterobacter asburiae, Enterobacter cancerogenus, Enterobacter cloacae, Enterobacter massiliensis, Enterococcus casseliflavus, Enterococcus durans, Enterococcus faecalis, Enterococcus faecium, Enterococcus flavescens, Enterococcus gallinarum, Enterococcus* sp., *Enterovibrio nigricans, Erysipelatoclostridium ramosum, Escherichia coli, Escherichia* sp., *Eubacterium biforme, Eubacterium dolichum, Eubacterium hallii, Eubacterium limosum, Eubacterium ramulus, Eubacterium rectale, Eubacterium siraeum, Eubacterium ventriosum, Exiguobacterium marinum, Exiguobacterium undae, Faecalibacterium* cf, *Faecalibacterium prausnitzii, Faecalitalea cylindroides, Ferrimonas balearica, Finegoldia magna, Flavobacterium daejeonense, Flavonifractor plautii, Fusicatenibacter saccharivorans, Fusobacterium gonidiaformans, Fusobacterium mortiferum, Fusobacterium necrophorum, Fusobacterium nucleatum, Fusobacterium periodonticum, Fusobacterium* sp., *Fusobacterium ulcerans, Fusobacterium varium, Gallibacterium anatis, Gemmiger formicilis, Gordonibacter pamelaeae, Hafnia alvei, Helicobacter bilis, Helicobacter bills, Helicobacter canadensis, Helicobacter canis, Helicobacter cinaedi, Helicobacter macacae, Helicobacter pametensis, Helicobacter pullorum, Helicobacter pylori, Helicobacter rodentium, Helicobacter winghamensis, Herbaspirillum massiliense, Holdemanella biformis, Holdemania fdiformis, Holdemania filiformis, Holdemania massiliensis, Holdemaniafiliformis, Hungatella hathewayi, Intestinibacter bartlettii, Intestinimonas butyriciproducens, Klebsiella oxytoca, Klebsiella pneumoniae, Kurthia massiliensis, Lachnospira pectinoschiza, Lactobacillus acidophilus, Lactobacillus amylolyticus, Lactobacillus animalis, Lactobacillus antri, Lactobacillus brevis, Lactobacillus buchneri, Lactobacillus casei, Lactobacillus curvatus, Lactobacillus delbrueckii, Lactobacillus fermentum, Lactobacillus gasseri, Lactobacillus helveticus, Lactobacillus hilgardii, Lactobacillus iners, Lactobacillus intestinalis,*

*Lactobacillus johnsonii, Lactobacillus murinus, Lactobacillus paracasei, Lactobacillus plantarum, Lactobacillus reuteri, Lactobacillus rhamnosus, Lactobacillus ruminis, Lactobacillus sakei, Lactobacillus salivarius, Lactobacillus ultunensis, Lactobacillus vaginalis, Lactobacillusplantarum* subsp., *Leuconostoc mesenteroides, Leuconostoc pseudomesenteroides, Listeria grayi, Listeria innocua, Mannheimia granulomatis, Marvinbryantia formatexigens, Megamonas funiformis, Megamonas hypermegale, Methanobrevibacter smithii, Methanobrevibacter smithiiFI, Micrococcus luteus, Microvirgula aerodenitrificans, Mitsuokella jalaludinii, Mitsuokella multacida, Mollicutes bacterium, Murimonas intestini, Neisseria macacae, Nitriliruptor alkaliphilus, Oceanobacillus massiliensis, Odoribacter laneus, Odoribacter splanchnicus, Ornithobacterium rhinotracheale, Oxalobacter formigenes, Paenibacillus barengoltzii, Paenibacillus chitinolyticus, Paenibacillus lautus, Paenibacillus motobuensis, Paenibacillus senegalensis, Paenisporosarcina quisquiliarum, Parabacteroides distasonis, Parabacteroides goldsteinii, Parabacteroides gordonii, Parabacteroides johnsonii, Parabacteroides merdae, Paraprevotella xylaniphila, Parasutterella excrementihominis, Parvimonas micra, Pediococcus acidilactici, Peptoclostridium difficile, Peptoniphilus harei, Peptoniphilus obesi, Peptoniphilus senegalensis, Peptoniphilus timonensis, Phascolarctobacterium succinatutens, Porphyromonas asaccharolytica, Porphyromonas uenonis, Prevotella baroniae, Prevotella bivia, Prevotella copri, Prevotella dentalis, Prevotella micans, Prevotella multisaccharivorax, Prevotella oralis, Prevotella salivae, Prevotella stercorea, Prevotella veroralis, Propionibacterium acnes, Propionibacterium avidum, Propionibacterium freudenreichii, Propionimicrobium lymphophilum, Proteus mirabilis, Proteuspenneri* ATCC, *Providencia alcalifaciens, Providencia rettgeri, Providencia rustigianii, Providencia stuartii, Pseudoflavonifractor capillosus, Pseudomonas aeruginosa, Pseudomonas luteola, Ralstonia pickettii, Rheinheimera perlucida, Rheinheimera texasensis, Riemerella columbina, Romboutsia lituseburensis, Roseburia faecis, Roseburia intestinalis, Roseburia inulinivorans, Ruminococcus bicirculans, Ruminococcus bromii, Ruminococcus callidus, Ruminococcus champanellensis, Ruminococcus faecis, Ruminococcus gnavus, Ruminococcus lactaris, Ruminococcus obeum, Ruminococcus* sp., *Ruminococcus* sp., *Ruminococcus torques, Sarcina ventriculi, Sellimonas intestinalis, Senegalimassilia anaerobia, Shigella sonnei, Slackia piriformis, Staphylococcus epidermidis, Staphylococcus lentus, Staphylococcus nepalensis, Staphylococcus pseudintermedius, Staphylococcus xylosus, Stenotrophomonas maltophilia, Streptococcus agalactiae, Streptococcus anginosus, Streptococcus australis, Streptococcus caballi, Streptococcus castoreus, Streptococcus didelphis, Streptococcus equinus, Streptococcus gordonii, Streptococcus henryi, Streptococcus hyovaginalis, Streptococcus infantarius, Streptococcus infantis, Streptococcus lutetiensis, Streptococcus merionis, Streptococcus mitis, Streptococcus mutans, Streptococcus oralis, Streptococcus ovis, Streptococcus parasanguinis, Streptococcus plurextorum, Streptococcus porci, Streptococcus pyogenes, Streptococcus salivarius, Streptococcus sobrinus, Streptococcus thermophilus, Streptococcus thoraltensis, Streptomyces albus, Subdoligranulum variabile, Succinatimonas hippei, Sutterella parvirubra, Sutterella wadsworthensis, Terrisporobacter glycolicus, Terrisporobacter mayombei, Thalassobacillus devorans, Timonella senegalensis, Turicibacter sanguinis,* unknown sp, unknown sp., *Varibaculum cambriense, Veillonella atypica, Veillonella dispar, Veillonella parvula, Vibrio cincinnatiensis, Virgibacillus salexigens,* and *Weissella paramesenteroides.*

In other embodiments, the targeted bacteria cells are those commonly found on the skin microbiota and are without limitation *Acetobacter farinalis, Acetobacter malorum, Acetobacter orleanensis, Acetobacter sicerae, Achromobacter anxifer, Achromobacter denitrificans, Achromobacter marplatensis, Achromobacter spanius, Achromobacter xylosoxidans* subsp. *xylosoxidans, Acidovorax konjaci, Acidovorax radicis, Acinetobacter johnsonii, Actinomadura citrea, Actinomadura coerulea, Actinomadura fibrosa, Actinomadura fulvescens, Actinomadura jiaoheensis, Actinomadura luteofluorescens, Actinomadura mexicana, Actinomadura nitritigenes, Actinomadura verrucosospora, Actinomadura yumaensis, Actinomyces odontolyticus, Actinomycetospora atypica, Actinomycetospora corticicola, Actinomycetospora rhizophila, Actinomycetospora rishiriensis, Aeromonas australiensis, Aeromonas bestiarum, Aeromonas bivalvium, Aeromonas encheleia, Aeromonas eucrenophila, Aeromonas hydrophila* subsp. *hydrophila, Aeromonas piscicola, Aeromonas popoffii, Aeromonas rivuli, Aeromonas salmonicida* subsp. *pectinolytica, Aeromonas salmonicida* subsp. *smithia, Amaricoccus kaplicensis, Amaricoccus veronensis, Aminobacter aganoensis, Aminobacter ciceronei, Aminobacter lissarensis, Aminobacter niigataensis, Ancylobacter polymorphus, Anoxybacillus flavithermus* subsp. *yunnanensis, Aquamicrobium aerolatum, Archangium gephyra, Archangium gephyra, Archangium minus, Archangium violaceum, Arthrobacter viscosus, Bacillus anthracis, Bacillus australimaris, Bacillus drentensis, Bacillus mycoides, Bacillus pseudomycoides, Bacillus pumilus, Bacillus safensis, Bacillus vallismortis, Bosea thiooxidans, Bradyrhizobium huanghuaihaiense, Bradyrhizobium japonicum, Brevundimonas aurantiaca, Brevundimonas intermedia, Burkholderia aspalathi, Burkholderia choica, Burkholderia cordobensis, Burkholderia diffusa, Burkholderia insulsa, Burkholderia rhynchosiae, Burkholderia terrestris, Burkholderia udeis, Buttiauxella gaviniae, Caenimonas terrae, Capnocytophaga gingivalis, Chitinophaga dinghuensis, Chryseobacterium gleum, Chryseobacterium greenlandense, Chryseobacterium jejuense, Chryseobacterium piscium, Chryseobacterium sediminis, Chryseobacterium tructae, Chryseobacterium ureilyticum, Chryseobacterium vietnamense, Corynebacterium accolens, Corynebacterium afermentans* subsp. *lipophilum, Corynebacterium minutissimum, Corynebacterium sundsvallense, Cupriavidus metallidurans, Cupriavidus nantongensis, Cupriavidus necator, Cupriavidus pampae, Cupriavidus yeoncheonensis, Curtobacterium flaccumfaciens, Devosia epidermidihirudinis, Devosia riboflavina, Devosia riboflavina, Diaphorobacter oryzae, Dietzia psychralcaliphila, Ensifer adhaerens, Ensifer americanus, Enterococcus malodoratus, Enterococcus pseudoavium, Enterococcus viikkiensis, Enterococcus xiangfangensis, Erwinia rhapontici, Falsirhodobacter halotolerans, Flavobacterium araucananum, Flavobacterium frigidimaris, Gluconobacter frateurii, Gluconobacter thailandicus, Gordonia alkanivorans, Halomonas aquamarina, Halomonas axialensis, Halomonas meridiana, Halomonas olivaria, Halomonas songnenensis, Halomonas variabilis, Herbaspirillum chlorophenolicum, Herbaspirillum frisingense, Herbaspirillum hiltneri, Herbaspirillum huttiense* subsp. *putei, Herbaspirillum lusitanum, Herminiimonas fonticola, Hydrogenophaga intermedia, Hydrogenophaga pseudoflava, Klebsiella oxytoca, Kosakonia sacchari, Lactobacillus delbrueckii* subsp. *bulgaricus, Lactobacillus modestisalitolerans, Lactobacillus*

*plantarum* subsp. *argentoratensis*, *Lactobacillus xiangfangensis*, *Lechevalieria roselyniae*, *Lentzea albida*, *Lentzea californiensis*, *Leuconostoc carnosum*, *Leuconostoc citreum*, *Leuconostoc gelidum* subsp. *gasicomitatum*, *Leuconostoc mesenteroides* subsp. *suionicum*, *Luteimonas aestuarii*, *Lysobacter antibioticus*, *Lysobacter koreensis*, *Lysobacter oryzae*, *Magnetospirillum moscoviense*, *Marinomonas alcarazii*, *Marinomonas primoryensis*, *Massilia aurea*, *Massilia jejuensis*, *Massilia kyonggiensis*, *Massilia timonae*, *Mesorhizobium acaciae*, *Mesorhizobium qingshengii*, *Mesorhizobium shonense*, *Methylobacterium haplocladii*, *Methylobacterium platani*, *Methylobacterium pseudosasicola*, *Methylobacterium zatmanii*, *Microbacterium oxydan*, *Micromonospora chaiyaphumensis*, *Micromonospora chalcea*, *Micromonospora citrea*, *Micromonospora coxensis*, *Micromonospora echinofusca*, *Micromonospora halophytica*, *Micromonospora kangleipakensis*, *Micromonospora maritima*, *Micromonospora nigra*, *Micromonospora purpureochromogene*, *Micromonospora rhizosphaerae*, *Micromonospora saelicesensis*, *Microvirga subterranea*, *Micro virga zambiensis*, *Mycobacterium alvei*, *Mycobacterium avium* subsp. *silvaticum*, *Mycobacterium colombiense*, *Mycobacterium conceptionense*, *Mycobacterium conceptionense*, *Mycobacterium farcinogenes*, *Mycobacterium fortuitum* subsp. *fortuitum*, *Mycobacterium goodii*, *Mycobacterium insubricum*, *Mycobacterium Ilatzerense*, *Mycobacterium neoaurum*, *Mycobacterium neworleansense*, *Mycobacterium obuense*, *Mycobacterium peregrinum*, *Mycobacterium saopaulense*, *Mycobacterium septicum*, *Mycobacterium setense*, *Mycobacterium smegmatis*, *Neisseria subflava*, *Nocardia lijiangensis*, *Nocardia thailandica*, *Novosphingobium barchaimii*, *Novosphingobium lindaniclasticum*, *Novosphingobium lindaniclasticum*, *Novosphingobium mathurense*, *Ochrobactrum pseudogrignonense*, *Oxalicibacterium solurbis*, *Paraburkholderia glathei*, *Paraburkholderia humi*, *Paraburkholderia phenazinium*, *Paraburkholderia phytofirmans*, *Paraburkholderia sordidicola*, *Paraburkholderia terricola*, *Paraburkholderia xenovorans*, *Paracoccus laeviglucosivorans*, *Patulibacter ginsengiterrae*, *Polymorphospora rubra*, *Porphyrobacter colymbi*, *Prevotella jejuni*, *Prevotella melaninogenica*, *Propionibacterium acnes* subsp. *elongatum*, *Proteus vulgaris*, *Providencia rustigianii*, *Pseudoalteromonas agarivorans*, *Pseudoalteromonas atlantica*, *Pseudoalteromonas paragorgicola*, *Pseudomonas asplenii*, *Pseudomonas asuensis*, *Pseudomonas benzenivorans*, *Pseudomonas cannabina*, *Pseudomonas cissicola*, *Pseudomonas congelans*, *Pseudomonas costantinii*, *Pseudomonas ficuserectae*, *Pseudomonas frederiksbergensis*, *Pseudomonas graminis*, *Pseudomonas jessenii*, *Pseudomonas koreensis*, *Pseudomonas koreensis*, *Pseudomonas kunmingensis*, *Pseudomonas marginalis*, *Pseudomonas mucidolens*, *Pseudomonas panacis*, *Pseudomonas plecoglossicida*, *Pseudomonas poae*, *Pseudomonas pseudoalcaligenes*, *Pseudomonas putida*, *Pseudomonas reinekei*, *Pseudomonas rhizosphaerae*, *Pseudomonas seleniipraecipitans*, *Pseudomonas umsongensis*, *Pseudomonas zhaodongensis*, *Pseudonocardia alaniniphila*, *Pseudonocardia ammonioxydans*, *Pseudonocardia autotrophica*, *Pseudonocardia kongjuensis*, *Pseudonocardia yunnanensis*, *Pseudorhodoferax soli*, *Pseudoxanthomonas daejeonensis*, *Pseudoxanthomonas indica*, *Pseudoxanthomonas kaohsiungensis*, *Psychrobacter aquaticus*, *Psychrobacter arcticus*, *Psychrobacter celer*, *Psychrobacter marincola*, *Psychrobacter nivimaris*, *Psychrobacter okhotskensis*, *Psychrobacter okhotskensis*, *Psychrobacter piscatorii*, *Psychrobacter pulmonis*, *Ramlibacter ginsenosidimutans*, *Rheinheimera japonica*, *Rheinheimera muenzenbergensis*, *Rheinheimera soli*, *Rheinheimera tangshanensis*, *Rheinheimera texasensis*, *Rheinheimera tilapiae*, *Rhizobium alamii*, *Rhizobium azibense*, *Rhizobium binae*, *Rhizobium daejeonense*, *Rhizobium endophyticum*, *Rhizobium etli*, *Rhizobium fabae*, *Rhizobium freirei*, *Rhizobium gallicum*, *Rhizobium loessense*, *Rhizobium sophoriradicis*, *Rhizobium taibaishanense*, *Rhizobium vallis*, *Rhizobium vignae*, *Rhizobium vignae*, *Rhizobium yanglingense*, *Rhodococcus baikonurensis*, *Rhodococcus enclensis*, *Rhodoferax saidenbachensis*, *Rickettsia canadensis*, *Rickettsia heilongjiangensis*, *Rickettsia honei*, *Rickettsia raoultii*, *Roseateles aquatilis*, *Roseateles aquatilis*, *Salmonella enterica* subsp. *salamae*, *Serratia ficaria*, *Serratia myotis*, *Serratia vespertilionis*, *Shewanella aestuarii*, *Shewanella decolorationis*, *Sphingobium amiense*, *Sphingobium baderi*, *Sphingobium barthaii*, *Sphingobium chlorophenolicum*, *Sphingobium cupriresistens*, *Sphingobium czechense*, *Sphingobium fuliginis*, *Sphingobium indicum*, *Sphingobium indicum*, *Sphingobium japonicum*, *Sphingobium lactosutens*, *Sphingomonas dokdonensis*, *Sphingomonas pseudosanguinis*, *Sphingopyxis chilensis*, *Sphingopyxis fribergensis*, *Sphingopyxis granuli*, *Sphingopyxis indica*, *Sphingopyxis witfiariensis*, *Staphylococcus agnetis*, *Staphylococcus aureus* subsp. *aureus*, *Staphylococcus epidermidis*, *Staphylococcus hominis* subsp. *novobiosepticus*, *Staphylococcus nepalensis*, *Staphylococcus saprophyticus* subsp. *bovis*, *Staphylococcus sciuri* subsp. *carnaticus*, *Streptomyces caeruleatus*, *Streptomyces canarius*, *Streptomyces capoamus*, *Streptomyces ciscaucasicus*, *Streptomyces griseorubiginosus*, *Streptomyces olivaceoviridis*, *Streptomyces panaciradicis*, *Streptomyces phaeopurpureus*, *Streptomyces pseudovenezuelae*, *Streptomyces resistomycificus*, *Tianweitania sediminis*, *Tsukamurella paurometabola*, *Variovorax guangxiensis*, *Vogesella alkaliphila*, *Xanthomonas arboricola*, *Xanthomonas axonopodis*, *Xanthomonas cassavae*, *Xanthomonas cucurbitae*, *Xanthomonas cynarae*, *Xanthomonas euvesicatoria*, *Xanthomonas fragariae*, *Xanthomonas gardneri*, *Xanthomonas perforans*, *Xanthomonas pisi*, *Xanthomonas populi*, *Xanthomonas vasicola*, *Xenophilus aerolatus*, *Yersinia nurmii*, *Abiotrophia defectiva*, *Acidocella aminolytica*, *Acinetobacter guangdongensis*, *Acinetobacter parvus*, *Acinetobacter radioresistens*, *Acinetobacter soli*, *Acinetobacter variabilis*, *Actinomyces cardiffensis*, *Actinomyces dentalis*, *Actinomyces europaeus*, *Actinomyces gerencseriae*, *Actinomyces graevenitzii*, *Actinomyces haliotis*, *Actinomyces johnsonii*, *Actinomyces massiliensis*, *Actinomyces meyeri*, *Actinomyces meyeri*, *Actinomyces naeslundii*, *Actinomyces neuii* subsp. *anitratus*, *Actinomyces odontolyticus*, *Actinomyces oris*, *Actinomyces turicensis*, *Actinomycetospora corticicola*, *Actinotignum schaalii*, *Aerococcus christensenii*, *Aerococcus urinae*, *Aeromicrobium flavum*, *Aeromicrobium massiliense*, *Aeromicrobium tamlense*, *Aeromonas sharmana*, *Aggregatibacter aphrophilus*, *Aggregatibactersegnis*, *Agrococcus baldri*, *Albibacter methylovorans*, *Alcaligenes faecalis* subsp. *faecalis*, *Algoriphagus ratkowskyi*, *Alkalibacterium olivapovliticus*, *Alkalibacterium pelagium*, *Alkalibacterium pelagium*, *Alloprevotella rava*, *Alsobacter metallidurans*, *Amaricoccus kaplicensis*, *Amaricoccus veronensis*, *Anaerococcus hydrogenalis*, *Anaerococcus lactolyticus*, *Anaerococcus murdochii*, *Anaerococcus octavius*, *Anaerococcus prevotii*, *Anaerococcus vaginalis*, *Aquabacterium citratiphilum*, *Aquabacterium olei*, *Aquabacterium olei*, *Aquabacterium parvum*, *Aquincola tertiaricarbonis*, *Arcobacter venerupis*, *Arsenicicoccus bolidensis*, *Arthrobacter russicus*, *Asticcacaulis excentricus*, *Atopobium deltae*, *Atopobium parvulum*, *Atopobium rimae*, *Atopobium vaginae*, *Aureimonas altamirensis, Aureimonas rubiginis, Azospira oryzae, Azospirillum oryzae, Bacillus circulans, Bacillus drentensis, Bacillus fastidiosus, Bacillus lehensis, Bacillus oceanisediminis, Bacillus rhizosphaerae, Bacteriovorax stolpii, Bacteroides coagulans, Bacteroides dorei, Bacteroides fragilis, Bacteroides ovatus, Bacteroides stercoris, Bacteroides uniformis, Bacteroides vulgatus, Bdellovibrio bacteriovorus, Bdellovibrio exovorus, Belnapia moabensis, Belnapia soli, Blautia hansenii, Blautia obeum, Blautia wexlerae, Bosea lathyri, Brachybacterium fresconis, Brachybacterium muris, Brevibacterium ammoniilyticum, Brevibacterium casei, Brevibacterium epidermidis, Brevibacterium iodinum, Brevibacterium luteolum, Brevibacterium paucivorans, Brevibacterium pityocampae, Brevibacterium sanguinis, Brevundimonas albigilva, Brevundimonas diminuta, Brevundimonas vancanneytii, Caenimonas terrae, Calidifontibacter indicus, Campylobacter concisus, Campylobacter gracilis, Campylobacter hominis, Campylobacter rectus, Campylobacter showae, Campylobacter ureolyticus, Capnocytophaga gingivalis, Capnocytophaga leadbetteri, Capnocytophaga ochracea, Capnocytophaga sputigena, Cardiobacterium hominis, Cardiobacterium valvarum, Carnobacterium divergens, Catonella morbi, Caulobacter henricii, Cavicella subterranea, Cellulomonas xylanilyfica, Cellvibrio vulgaris, Chitinimonas taiwanensis, Chryseobacterium arachidis, Chryseobacterium daecheongense, Chryseobacterium formosense, Chryseobacterium formosense, Chryseobacterium greenlandense, Chryseobacterium indologenes, Chryseobacterium piscium, Chryseobacterium rigui, Chryseobacterium solani, Chryseobacterium taklimakanense, Chryseobacterium ureilyticum, Chryseobacterium ureilyficum, Chryseobacterium zeae, Chryseomicrobium aureum, Cloacibacterium haliotis, Cloacibacterium normanense, Cloacibacterium normanense, Collinsella aerofaciens, Comamonas denitrificans, Comamonas terrigena, Corynebacterium accolens, Corynebacterium afermentans subsp. lipophilum, Corynebacterium ammoniagenes, Corynebacterium amycolatum, Corynebacterium aurimucosum, Corynebacterium aurimucosum, Corynebacterium coyleae, Corynebacterium durum, Corynebacterium freiburgense, Corynebacterium glaucum, Corynebacterium glyciniphilum, Corynebacterium imitans, Corynebacterium jeikeium, Corynebacterium jeikeium, Corynebacterium kroppenstedtii, Corynebacterium fipophilofiavum, Corynebacterium massiliense, Corynebacterium mastitidis, Corynebacterium matruchotii, Corynebacterium minutissimum, Corynebacterium mucifaciens, Corynebacterium mustelae, Corynebacterium mycetoides, Corynebacterium pyruviciproducens, Corynebacterium simulans, Corynebacterium singulare, Corynebacterium sputi, Corynebacterium suicordis, Corynebacterium tuberculostearicum, Corynebacterium tuberculostearicum, Corynebacterium ureicelerivorans, Corynebacterium variabile, Couchioplanes caeruleus subsp. caeruleus, Cupriavidus metalfidurans, Curtobacterium herbarum, Dechloromonas agitata, Deinococcus actinosclerus, Deinococcus antarcticus, Deinococcus caeni, Deinococcus ficus, Deinococcus geothermalis, Deinococcus radiodurans, Deinococcus wulumuqiensis, Deinococcus xinjiangensis, Dermabacter hominis, Dermabacter vaginalis, Dermacoccus nishinomiyaensis, Desemzia incerta, Desertibacter roseus, Dialister invisus, Dialister micraerophilus, Dialister propionicifaciens, Dietzia aurantiaca, Dietzia cercidiphylfi, Dietzia timorensis, Dietzia timorensis, Dokdonella koreensis, Dokdonella koreensis, Dolosigranulum pigrum, Eikenella corrodens, Elizabethkingia miricola, Elstera litoralis, Empedobacter brevis, Enhydrobacter aerosaccus, Enterobacter xiangfangensis, Enterococcus aquimarinus, Enterococcus faecalis, Enterococcus olivae, Erwinia rhapontici, Eubacterium eligens, Eubacterium infirmum, Eubacterium rectale, Eubacterium saphenum, Eubacterium sulci, Exiguobacterium mexicanum, Facklamia tabacinasalis, Falsirhodobacter halotolerans, Finegoldia magna, Flavobacterium cutihirudinis, Flavobacterium lindanitolerans, Flavobacterium resistens, Friedmanniella capsulata, Fusobacterium nucleatum subsp. polymorphum, Gemella haemolysans, Gemella morbillorum, Gemella palaticanis, Gemella sanguinis, Gemmobacter aquaticus, Gemmobacter caeni, Gordonia jinhuaensis, Gordonia kroppenstedtii, Gordonia polyisoprenivorans, Gordonia polyisoprenivorans, Granulicatella adiacens, Granulicatella elegans, Haemophilus parainfluenzae, Haemophilus sputorum, Halomonas suffidaeris, Herpetosiphon aurantiacus, Hydrocarboniphaga effusa, Idiomarina marls, Janibacter anophelis, Janibacter hoylei, Janibacter indicus, Janibacter limosus, Janibacter melonis, Jeotgalicoccus halophilus, Jonquetella anthropi, Kaistia geumhonensis, Kingella denitrificans, Kingella oralis, Klebsiella oxytoca, Knoeffia aerolata, Knoeffia locipacati, Kocuria atrinae, Kocuria carniphila, Kocuria kristinae, Kocuria palustris, Kocuria turfanensis, Lachnoanaerobaculum saburreum, Lachnoanaerobaculum saburreum, Lactobacillus crispatus, Lactobacillus iners, Lactococcus lactis subsp. lactis, Lactococcus lactis subsp. lactis, Lactococcus piscium, Lapillicoccus jejuensis, Lautropia mirabilis, Legionella beliardensis, Leptotrichia buccalis, Leptotrichia goodfellowii, Leptotrichia hofstadii, Leptotrichia hongkongensis, Leptotrichia shahii, Leptotrichia trevisanii, Leptotrichia wadei, Luteimonas terricola, Lysinibacillus fusiformis, Lysobacter spongiicola, Lysobacter xinjiangensis, Macrococcus caseolyticus, Marmoricola pocheonensis, Marmoricola scoriae, Massilia alkalitolerans, Massilia alkalitolerans, Massilia aurea, Massilia plicata, Massilia timonae, Megamonas rupellensis, Meiothermus silvanus, Methylobacterium dankookense, Methylobacterium goesingense, Methylobacterium goesingense, Methylobacterium isbiliense, Methylobacterium jeotgali, Methylobacterium oxalidis, Methylobacterium platani, Methylobacterium pseudosasicola, Methyloversatilis universalis, Microbacterium foliorum, Microbacterium hydrothermale, Microbacterium hydrothermale, Microbacterium lacticum, Microbacterium lacticum, Microbacterium laevaniformans, Microbacterium paludicola, Microbacterium petrolearium, Microbacterium phyllosphaerae, Microbacterium resistens, Micrococcus antarcticus, Micrococcus cohnii, Micrococcus flavus, Micrococcus lylae, Micrococcus terreus, Microlunatus aurantiacus, Micropruina glycogenica, Microvirga aerilata, Microvirga aerilata, Microvirga subterranea, Microvirga vignae, Microvirga zambiensis, Microvirgula aerodenitrificans, Mogibacterium timidum, Moraxella atlantae, Moraxella catarrhalis, Morganella morganii subsp. morganii, Morganella psychrotolerans, Murdochiella asaccharolytica, Mycobacterium asiaticum, Mycobacterium chubuense, Mycobacterium crocinum, Mycobacterium gadium, Mycobacterium holsaticum, Mycobacterium iranicum, Mycobacterium longobardum, Mycobacterium neoaurum, Mycobacterium neoaurum, Mycobacterium obuense, Negativicoccus succinicivorans, Neisseria bacilliformis, Neisseria oralis, Neisseria sicca, Neisseria subflava, Nesterenkonia lacusekhoensis, Nesterenkonia rhizosphaerae, Nevskia persephonica, Nevskia ramosa, Niabella yanshanensis, Niveibacterium umoris, Nocardia niwae, Nocardia thailandica, Nocardioides agariphilus, Nocardioides dilutus, Nocardioides ganghwensis, Nocardioides hwasunensis, Nocardioides nanhaiensis,

*Nocardioides sediminis, Nosocomiicoccus ampullae, Noviherbaspirillum malthae, Novosphingobium lindaniclasticum, Novosphingobium rosa, Ochrobactrum rhizosphaerae, Olsenella uli, Ornithinimicrobium murale, Ornithinimicrobium tianjinense, Oryzobacterterrae, Ottowia beijingensis, Paenalcaligenes suwonensis, Paenibacillus agaridevorans, Paenibacillus phoenicis, Paenibacillus xylanexedens, Paludibacterium yongneupense, Pantoea cypripedii, Parabacteroides distasonis, Paraburkholderia andropogonis, Paracoccus alcaliphilus, Paracoccus angustae, Paracoccus kocurii, Paracoccus laeviglucosivorans, Paracoccus sediminis, Paracoccus sphaerophysae, Paracoccus yeei, Parvimonas micra, Parviterribacter multiflagellatus, Patulibacter ginsengiterrae, Pedobacter aquatilis, Pedobacter ginsengisoli, Pedobacter xixiisoli, Peptococcus niger, Peptoniphilus coxii, Peptoniphilus gorbachii, Peptoniphilus harei, Peptoniphilus koenoeneniae, Peptoniphilus lacrimalis, Peptostreptococcus anaerobius, Peptostreptococcus stomatis, Phascolarctobacterium faecium, Phenylobacterium haematophilum, Phenylobacterium kunshanense, Pluralibacter gergoviae, Polymorphobacter multimanifer, Porphyromonas bennonis, Porphyromonas endodontalis, Porphyromonas gingivalis, Porphyromonas gingivicanis, Porphyromonas pasteri, Porphyromonas pogonae, Porphyromonas somerae, Povalibacter uvarum, Prevotella aurantiaca, Prevotella baroniae, Prevotella bivia, Prevotella buccae, Prevotella buccalis, Prevotella copri, Prevotella corporis, Prevotella denticola, Prevotella enoeca, Prevotella histicola, Prevotella intermedia, Prevotella jejuni, Prevotella jejuni, Prevotella maculosa, Prevotella melaninogenica, Prevotella melaninogenica, Prevotella micans, Prevotella multiformis, Prevotella nanceiensis, Prevotella nigrescens, Prevotella oris, Prevotella oulorum, Prevotella pallens, Prevotella pleuritidis, Prevotella saccharolytica, Prevotella salivae, Prevotella shahii, Prevotella timonensis, Prevotella veroralis, Propionibacterium acidifaciens, Propionibacterium acnes* subsp. *acnes, Propionibacterium acnes* subsp. *acnes, Propionibacterium acnes* subsp. *elongatum, Propionibacterium granulosum, Propionimicrobium lymphophilum, Propionispira arcuata, Pseudokineococcus lusitanus, Pseudomonas aeruginosa, Pseudomonas chengduensis, Pseudonocardia benzenivorans, Pseudorhodoplanes sinuspersici, Psychrobacter sanguinis, Ramlibacter ginsenosidimutans, Rheinheimera aquimaris, Rhizobium alvei, Rhizobium daejeonense, Rhizobium larrymoorei, Rhizobium rhizoryzae, Rhizobium soli, Rhizobium taibaishanense, Rhizobium vignae, Rhodanobacter glycinis, Rhodobacter veldkampii, Rhodococcus enclensis, Rhodococcus fascians, Rhodococcus fascians, Rhodovarius lipocyclicus, Rivicola pingtungensis, Roseburia inulinivorans, Rosenbergiella nectarea, Roseomonas aerilata, Roseomonas aquatica, Roseomonas mucosa, Roseomonas rosea, Roseomonas vinacea, Rothia aeria, Rothia amarae, Rothia dentocariosa, Rothia endophytica, Rothia mucilaginosa, Rothia nasimurium, Rubellimicrobium mesophilum, Rubellimicrobium roseum, Rubrobacter bracarensis, Rudaea cellulosilytica, Ruminococcus gnavus, Runella zeae, Saccharopolyspora rectivirgula, Salinicoccus qingdaonensis, Scardovia wiggsiae, Sediminibacterium ginsengisoli, Selenomonas artemidis, Selenomonas infelix, Selenomonas noxia, Selenomonas sputigena, Shewanella aestuarii, Shuttleworthia satelles, Simonsiella muelleri, Skermanella aerolata, Skermanella stibiiresistens, Slackia exigua, Smaragdicoccus niigatensis, Sneathia sanguinegens, Solirubrobacter soli, Sphingobacterium caeni, Sphingobacterium daejeonense, Sphingobacterium hotanense, Sphingobacterium kyonggiense, Sphingobacterium multivorum, Sphingobacterium nematocida, Sphingobacterium spiritivorum, Sphingobium amiense, Sphingobium indicum, Sphingobium lactosutens, Sphingobium subterraneum, Sphingomonas abaci, Sphingomonas aestuarii, Sphingomonas canadensis, Sphingomonas daechungensis, Sphingomonas dokdonensis, Sphingomonas echinoides, Sphingomonas fonticola, Sphingomonas fonticola, Sphingomonas formosensis, Sphingomonas gei, Sphingomonas hankookensis, Sphingomonas hankookensis, Sphingomonas koreensis, Sphingomonas kyeonggiensis, Sphingomonas laterariae, Sphingomonas mucosissima, Sphingomonas oligophenolica, Sphingomonas pseudosanguinis, Sphingomonas sediminicola, Sphingomonas yantingensis, Sphingomonas yunnanensis, Sphingopyxis indica, Spirosoma rigui, Sporacetigenium mesophilum, Sporocytophaga myxococcoides, Staphylococcus auricularis, Staphylococcus epidermidis, Staphylococcus epidermidis, Staphylococcus hominis* subsp. *novobiosepticus, Staphylococcus lugdunensis, Staphylococcus pettenkoferi, Stenotrophomonas koreensis, Stenotrophomonas rhizophila, Stenotrophomonas rhizophila, Streptococcus agalactiae, Streptococcus canis, Streptococcus cristatus, Streptococcus gordonii, Streptococcus infantis, Streptococcus intermedius, Streptococcus mutans, Streptococcus oligofermentans, Streptococcus oralis, Streptococcus sanguinis, Streptomyces iconiensis, Streptomyces yanglinensis, Tabrizicola aquatica, Tahibacter caeni, Tannerella forsythia, Tepidicella xavieri, Tepidimonas fonticaldi, Terracoccus luteus, Tessaracoccus flavescens, Thermus thermophilus, Tianweitania sediminis, Tianweitania sediminis, Treponema amylovorum, Treponema denticola, Treponema lecithinolyticum, Treponema medium, Turicella otitidis, Turicibacter sanguinis, Undibacterium oligocarboniphilum, Undibacterium squillarum, Vagococcus salmoninarum, Varibaculum cambriense, Vibrio metschnikovii, Xanthobacter tagetidis, Xenophilus aerolatus, Xenophilus arseniciresistens, Yimella lutea, Zimmermannella alba, Zimmermannella bifida* and/or *Zoogloea caeni*.

In other embodiments, the targeted bacteria cells are those commonly found in the vaginal microbiota and are, without limitation, *Acinetobacter antiviralis, Acinetobacter baumannii, Acinetobacter calcoaceticus, Acinetobacter johnsonii, Actinobaculum massiliense, Actinobaculum schaalii, Actinomyces europaeus, Actinomyces graevenitzii, Actinomyces israelii, Actinomyces meyeri, Actinomyces naeslundii, Actinomyces neuii, Actinomyces odontolyticus, Actinomyces turicensis, Actinomyces urogenitalis, Actinomyces viscosus, Aerococcus christensenii, Aerococcus urinae, Aerococcus viridans, Aeromonas encheleia, Aeromonas salmonicida, Afipia massiliensis, Agrobacterium tumefaciens, Algoriphagus aquatilis, Aliivibrio wodanis, Alistipes finegoldii, Alloiococcus otitis, Alloprevotella tannerae, Alloscardovia omnicolens, Altererythrobacter epoxidivorans, Ammoniphilus oxalaticus, Amnibacterium kyonggiense, Anaerococcus hydrogenalis, Anaerococcus lactolyticus, Anaerococcus murdochii, Anaerococcus obesiensis, Anaerococcus prevotii, Anaerococcus tetradius, Anaerococcus vaginalis, Anaeroglobus geminatus, Anoxybacillus pushchinoensis, Aquabacterium parvum, Arcanobacterium phocae, Arthrobacter aurescens, Asticcacaulis excentricus, Atopobium minutum, Atopobium parvulum, Atopobium rimae, Atopobium vaginae, Avibacterium gallinarum, Bacillus acidicola, Bacillus atrophaeus, Bacillus cereus, Bacillus cibi, Bacillus coahuilensis, Bacillus gaemokensis, Bacillus methanolicus, Bacillus oleronius, Bacillus pumilus, Bacillus shackletonii, Bacillus sporothermodurans, Bacillus subtilis, Bacillus wakoensis, Bacillus weihenstephanensis, Bacteroides barnesiae, Bacteroides coagulans, Bacteroides dorei, Bacte-* roides faecis, Bacteroides forsythus, Bacteroides fragilis, Bacteroides nordii, Bacteroides ovatus, Bacteroides salyersiae, Bacteroides stercoris, Bacteroides uniformis, Bacteroides vulgatus, Bacteroides xylanisolvens, Bacteroides zoogleoformans, Barnesiella viscericola, Bhargavaea cecembensis, Bifidobacterium adolescentis, Bifidobacterium bifidum, Bifidobacterium breve, Bifidobacterium dentium, Bifidobacterium logum subsp. infantis, Bifidobacterium longum, Bifidobacterium pseudocatenulatum, Bifidobacterium scardovii, Bilophila wadsworthia, Blautia hydrogenotrophica, Blautia obeum, Blautia producta, Brachybacterium faecium, Bradyrhizobium japonicum, Brevibacterium mcbrellneri, Brevibacterium otitidis, Brevibacterium paucivorans, Bulleidia extructa, Burkholderia fungorum, Burkholderia phenoliruptix, Caldicellulosiruptor saccharolyticus, Caldimonas taiwanensis, Campylobacter gracilis, Campylobacter hominis, Campylobacter sputorum, Campylobacter ureolyticus, Capnocytophaga ochracea, Cardiobacterium hominis, Catonella morbi, Chlamydia trachomatis, Chlamydophila abortus, Chondromyces robustus, Chryseobacterium aquaticum, Citrobacter youngae, Cloacibacterium normanense, Clostridium cavendishii, Clostridium colicanis, Clostridium jejuense, Clostridium perfringens, Clostridium ramosum, Clostridium sordellii, Clostridium viride, Comamonas terrigena, Corynebacterium accolens, Corynebacterium appendicis, Corynebacterium coyleae, Corynebacterium glucuronolyticum, Corynebacterium glutamicum, Corynebacterium jeikeium, Corynebacterium kroppenstedtii, Corynebacterium lipophiloflavum, Corynebacterium minutissimum, Corynebacterium mucifaciens, Corynebacterium nuruki, Corynebacterium pseudo genitalium, Corynebacterium pyruviciproducens, Corynebacterium singulare, Corynebacterium striatum, Corynebacterium tuberculostearicum, Corynebacterium xerosis, Cryobacterium psychrophilum, Curtobacterium flaccumfaciens, Cutibacterium acnes, Cutibacterium avidum, Cytophaga xylanolytica, Deinococcus radiophilus, Delftia tsuruhatensis, Desulfovibrio desulfuricans, Dialister invisus, Dialister microaerophilus, Dialister pneumosintes, Dialister propionicifaciens, Dickeya chrysanthemi, Dorea longicatena, Eggerthella lenta, Eggerthia catenaformis, Eikenella corrodens, Enhydrobacter aerosaccus, Enterobacter asburiae, Enterobacter cloacae, Enterococcus avium, Enterococcus durans, Enterococcus faecalis, Enterococcus faecium, Enterococcus hirae, Erwinia persicina, Erwinia rhapontici, Erwinia toletana, Escherichia coli, Escherichia fergusonii, Eubacterium brachy, Eubacterium eligens, Eubacterium nodatum, Eubacterium rectale, Eubacterium saphenum, Eubacterium siraeum, Eubacterium sulci, Eubacterium yurii, Exiguobacterium acetylicum, Facklamia ignava, Faecalibacterium prausnitzii, Filifactor alocis, Finegoldia magna, Fusobacterium gonidiaformans, Fusobacterium nucleatum, Fusobacterium periodonticum, Gardnerella vaginalis, Gemella asaccharolytica, Gemella bergeri, Gemella haemolysans, Gemella sanguinis, Geobacillus stearothermophilus, Geobacillus thermocatenulatus, Geobacillus thermoglucosidasius, Geobacter grbiciae, Granulicatella elegans, Haemophilus ducreyi, Haemophilus haemolyticus, Haemophilus parahaemolyticus, Haemophilus parainfluenzae, Hafnia alvei, Halomonas meridiana, Halomonas phoceae, Halomonas venusta, Herbaspirillum seropedicae, Janthinobacterium lividum, Jonquetella anthropi, Klebsiella granulomatis, Klebsiella oxytoca, Klebsiella pneumoniae, Lactobacillus acidophilus, Lactobacillus amylovorus, Lactobacillus brevis, Lactobacillus coleohominis, Lactobacillus crispatus, Lactobacillus curvatus, Lactobacillus delbrueckii, Lactobacillus fermentum, Lactobacillus gasseri, Lactobacillus helveticus, Lactobacillus iners, Lactobacillus jensenii, Lactobacillus johnsonii, Lactobacillus kalixensis, Lactobacillus kefiranofaciens, Lactobacillus kimchicus, Lactobacillus kitasatonis, Lactobacillus mucosae, Lactobacillus panis, Lactobacillus paracasei, Lactobacillus plantarum, Lactobacillus pontis, Lactobacillus reuteri, Lactobacillus rhamnosus, Lactobacillus salivarius, Lactobacillus ultunensis, Lactobacillus vaginalis, Lactococcus lactis, Leptotrichia buccalis, Leuconostoc carnosum, Leuconostoc citreum, Leuconostoc garlicum, Leuconostoc lactis, Leuconostoc mesenteroides, Lysinimonas kribbensis, Mageeibacillus indolicus, Maribacter orientalis, Marinomonas protea, Marinospirillum insulare, Massilia timonae, Megasphaera elsdenii, Megasphaera micronuciformis, Mesorhizobium amorphae, Methylobacterium radiotolerans, Methylotenera versatilis, Microbacterium halophilum, Micrococcus luteus, Microterricola viridarii, Mobiluncus curtisii, Mobiluncus mulieris, Mogibacterium timidum, Moorella glycerini, Moraxella osloensis, Morganella morganii, Moryella indoligenes, Murdochiella asaccharolytica, Mycoplasma alvi, Mycoplasma genitalium, Mycoplasma hominis, Mycoplasma muris, Mycoplasma salivarium, Negativicoccus succinicivorans, Neisseria flava, Neisseria gonorrhoeae, Neisseria mucosa, Neisseria subflava, Nevskia ramosa, Nevskia soli, Nitriliruptor alkaliphilus, Odoribacter splanchnicus, Oligella urethralis, Olsenella uli, Paenibacillus amylolyticus, Paenibacillus humicus, Paenibacillus pabuli, Paenibacillus pasadenensis, Paenibacillus pini, Paenibacillus validus, Pantoea agglomerans, Parabacteroides merdae, Paraburkholderia caryophylii, Paracoccus yeei, Parastreptomyces abscessus, Parvimonas micra, Pectobacterium betavasculorum, Pectobacterium carotovorum, Pediococcus acidilactici, Pediococcus ethanolidurans, Pedobacter alluvionis, Pedobacter wanjuense, Pelomonas aquatica, Peptococcus niger, Peptoniphilus asaccharolyticus, Peptoniphilus gorbachii, Peptoniphilus harei, Peptoniphilus indolicus, Peptoniphilus lacrimalis, Peptoniphilus massiliensis, Peptostreptococcus anaerobius, Peptostreptococcus massiliae, Peptostreptococcus stomatis, Photobacterium angustum, Photobacterium frigidiphilum, Photobacterium phosphoreum, Porphyromonas asaccharolytica, Porphyromonas bennonis, Porphyromonas catoniae, Porphyromonas endodontalis, Porphyromonas gingivalis, Porphyromonas somerae, Porphyromonas uenonis, Prevotella amnii, Prevotella baroniae, Prevotella bergensis, Prevotella bivia, Prevotella buccae, Prevotella buccalis, Prevotella colorans, Prevotella copri, Prevotella corporis, Prevotella dentalis, Prevotella denticola, Prevotella disiens, Prevotella intermedia, Prevotella loescheii, Prevotella marshii, Prevotella melaninogenica, Prevotella micans, Prevotella nigrescens, Prevotella oris, Prevotella pleuritidis, Prevotella ruminicola, Prevotella shahii, Prevotella stercorea, Prevotella timonensis, Prevotella veroralis, Propionimicrobium lymphophilum, Proteus mirabilis, Pseudomonas abietaniphila, Pseudomonas aeruginosa, Pseudomonas amygdali, Pseudomonas azotoformans, Pseudomonas chlororaphis, Pseudomonas cuatrocienegasensis, Pseudomonas fluorescens, Pseudomonas fulva, Pseudomonas lutea, Pseudomonas mucidolens, Pseudomonas oleovorans, Pseudomonas orientalis, Pseudomonas pseudoalcaligenes, Pseudomonas psychrophila, Pseudomonas putida, Pseudomonas synxantha, Pseudomonas syringae, Pseudomonas tolaasii, Pseudopropionibacterium propionicum, Rahnella aquatilis, Ralstonia pickettii, Ralstonia solanacearum, Raoultella planticola, Rhizobacter dauci, Rhizobium etli, Rhodococcus fascians, Rhodopseudomonas palustris, Roseburia intestinalis, Roseburia inulinivorans,

*Rothia mucilaginosa, Ruminococcus bromii, Ruminococcus gnavus, Ruminococcus torques, Sanguibacter keddieii, Sediminibacterium salmoneum, Selenomonas bovis, Serratia fonticola, Serratia liquefaciens, Serratia marcescens, Shewanella algae, Shewanella amazonensis, Shigella boydii, Shigella sonnei, Slackia exigua, Sneathia amnii, Sneathia sanguinegens, Solobacterium moorei, Sorangium cellulosum, Sphingobium amiense, Sphingobium japonicum, Sphingobium yanoikuyae, Sphingomonas wittichii, Sporosarcina aquimarina, Staphylococcus aureus, Staphylococcus auricularis, Staphylococcus capitis, Staphylococcus epidermidis, Staphylococcus haemolyticus, Staphylococcus hominis, Staphylococcus lugdunensis, Staphylococcus saprophyticus, Staphylococcus schleiferi, Staphylococcus simiae, Staphylococcus simulans, Staphylococcus warneri, Stenotrophomonas maltophilia, Stenoxybacter acetivorans, Streptococcus agalactiae, Streptococcus anginosus, Streptococcus australis, Streptococcus equinus, Streptococcus gallolyticus, Streptococcus infantis, Streptococcus intermedius, Streptococcus lutetiensis, Streptococcus marimammalium, Streptococcus mitis, Streptococcus mutans, Streptococcus oralis, Streptococcus parasanguinis, Streptococcus phocae, Streptococcus pseudopneumoniae, Streptococcus salivarius, Streptococcus sanguinis, Streptococcus thermophilus, Sutterella wadsworthensis, Tannerella forsythia, Terrahaemophilus aromaticivorans, Treponema denticola, Treponema maltophilum, Treponema parvum, Treponema vincentii, Trueperella bernardiae, Turicella otitidis, Ureaplasma parvum, Ureaplasma urealyticum, Varibaculum cambriense, Variovorax paradoxus, Veillonella atypica, Veillonella dispar, Veillonella montpellierensis, Veillonella parvula, Virgibacillus proomii, Viridibacillus arenosi, Viridibacillus arvi, Weissella cibaria, Weissella soli, Xanthomonas campestris, Xanthomonas vesicatoria, Zobellia laminariae* and/or *Zoogloea ramigera*.

In one embodiment, the targeted bacteria are *Escherichia coli*.

In one embodiment, the targeted bacteria are *Cutibacterium acnes* more specifically the acne related *Cutibacterium acnes* from the phylogroup IA1 or RT4, RT5, RT8, RT9, RT10 or Clonal Complex(CC) CC1, CC3, CC4, more specifically the ST1, ST3, ST4.

Bacteriophages used for preparing bacterial virus particles such as packaged phagemids, may target (e.g., specifically target) a bacterial cell from any one or more of the disclosed genus and/or species of bacteria to specifically deliver the payload.

In one embodiment, the targeted bacteria are pathogenic bacteria. The targeted bacteria can be virulent bacteria.

The targeted bacteria can be antibacterial resistance bacteria, preferably selected from the group consisting of extended-spectrum beta-lactamase-producing (ESBL) *Escherichia coli*, ESBL *Klebsiella pneumoniae*, vancomycin-resistant *Enterococcus* (VRE), methicillin-resistant *Staphylococcus aureus* (MRSA), multidrug-resistant (MDR) *Acinetobacter baumannii*, MDR *Enterobacter* spp., and a combination thereof. Preferably, the targeted bacteria can be selected from the group consisting of extended-spectrum beta-lactamase-producing (ESBL) *Escherichia coli* strains.

Alternatively, the targeted bacterium can be a bacterium of the microbiome of a given species, preferably a bacterium of the human microbiota.

Bacterial Viruses

The bacterial virus particles are prepared from bacterial virus. The bacterial viruses are chosen in order to be able to introduce the payload into the targeted bacteria.

Bacterial viruses are preferably bacteriophages. Bacteriophages are obligate intracellular parasites that multiply inside bacteria by co-opting some or all of the host biosynthetic machinery. Phage genomes come in a variety of sizes and shapes (e.g., linear or circular). Most phages range in size from 24-200 nm in diameter. Phages contain nucleic acid (i.e., genome) and proteins, and may be enveloped by a lipid membrane. Depending upon the phage, the nucleic acid genome can be either DNA or RNA, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage.

Optionally, the bacteriophage is selected from the Order Caudovirales consisting of, based on the taxonomy of Krupovic et al, Arch Virol, 2015:

family Myoviridae (such as, without limitation, genus Cp220virus, Cp8virus, Ea214virus, Felixo1virus, Mooglevirus, Suspvirus, Hp1virus, P2virus, Kayvirus, P100virus, Silviavirus, Spo1virus, Tsarbombavirus, Twortvirus, Cc31virus, Jd18virus, Js98virus, Kp15virus, Moonvirus, Rb49virus, Rb69virus, S16virus, Schizot4virus, Sp18virus, T4virus, Cr3virus, Selvirus, V5virus, Abouovirus, Agatevirus, Agrican357virus, Ap22virus, Arv1virus, B4virus, Bastillevirus, Bc431virus, Bcep78virus, Bcepmuvirus, Biquartavirus, Bxzlvirus, Cd119virus, Cp51virus, Cvm10virus, Eah2virus, Elvirus, Hapunavirus, Jimmervirus, Kpp10virus, M12virus, Machinavirus, Marthavirus, Msw3virus, Muvirus, Myohalovirus, Nit1virus, P1virus, Pakpunavirus, Pbunavirus, Phikzvirus, Rheph4virus, Rsl2virus, Rslunavirus, Secunda5virus, Sep1virus, Spn3virus, Svunavirus, Tg1virus, Vhmlvirus and Wphvirus)

family Podoviridae (such as, without limitation, genus Fri1virus, Kp32virus, Kp34virus, Phikmvvirus, Pradovirus, Sp6virus, T7virus, Cp1virus, P68virus, Phi29virus, Nona33virus, Pocjvirus, Tl2011virus, Bcep22virus, Bpp1virus, Cba41virus, Dfl12virus, Ea92virus, Epsilon15virus, F116virus, G7cvirus, Jwalphavirus, Kfl1virus, Kpp25virus, Lit1virus, Luz24virus, Luz7virus, N4virus, Nonanavirus, P22virus, Pagevirus, Phieco32virus, Prtbvirus, Sp58virus, Una961virus and Vp5virus)

family Siphoviridae (such as, without limitation, genus Camvirus, Likavirus, R4virus, Acadianvirus, Coopervirus, Pg1virus, Pipefishvirus, Rosebushvirus, Brujitavirus, Che9cvirus, Hawkeyevirus, Plotvirus, Jerseyvirus, K1gvirus, Sp31virus, Lmd1virus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Rogue1virus, Rtpvirus, T1virus, Tlsvirus, Ab18virus, Amigovirus, Anatolevirus, Andromedavirus, Attisvirus, Barnyardvirus, Bernal13virus, Biseptimavirus, Bronvirus, C2virus, C5virus, Cba181virus, Cbastvirus, Cecivirus, Che8virus, Chivirus, Cjw1virus, Corndogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, Lambdavirus, Laroyevirus, Liefievirus, Marvinvirus, Mudcatvirus, N15virus, Nonagvirus, Nplvirus, Omegavirus, P12002virus, P12024virus, P23virus, P70virus, Pa6virus, Pamx74virus, Patiencevirus, Pbilvirus, Pepy6virus, Pfr1virus, Phic31virus, Phicbkvirus, Phietavirus, Phifelvirus, Phij11virus, Pis4avirus, Psavirus, Psimunavirus, Rdjlvirus, Rer2virus, Sap6virus, Send513virus, Septima3virus, Seuratvirus, Sextaecvirus, Sfi11virus, Sfi21dt1virus, Sitaravirus, Sk1virus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus)
family Ackermannviridae (such as, without limitation, genus Ag3virus, Limestonevirus, Cba120virus and Vi1virus)

Optionally, the bacteriophage is not part of the Order Caudovirales but from families with Unassigned order such as, without limitation, family Tectiviridae (such as genus Alphatectivirus, Betatectivirus), family Corticoviridae (such as genus Corticovirus), family Inoviridae (such as genus Fibrovirus, Habenivirus, Inovirus, Lineavirus, Plectrovirus, Saetivirus, Vespertiliovirus), family Cystoviridae (such as genus Cystovirus), family Leviviridae (such as genus Allolevivirus, Levivirus), family Microviridae (such as genus Alpha3microvirus, G4microvirus, Phix174microvirus, Bdellomicrovirus, Chlamydiamicrovirus, Spiromicrovirus) and family Plasmaviridae (such as genus Plasmavirus).

Optionally, the bacteriophage is targeting Archea not part of the Order Caudovirales but from families with Unassigned order such as, without limitation, Ampullaviridae, FuselloViridae, Globuloviridae, Guttaviridae, Lipothrixviridae, Pleolipoviridae, Rudiviridae, Salterprovirus and Bicaudaviridae.

A non-exhaustive listing of bacterial genera and their known host-specific bacteria viruses is presented in the following paragraphs. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Actinomyces* can be infected by the following phages: Av-1, Av-2, Av-3, BF307, CTI, CT2, CT3, CT4, CT6, CT7, CT8 and 1281.

Bacteria of the genus *Aeromonas* can be infected by the following phages: AA-I, Aeh2, N, PMI, TP446, 3, 4, 11, 13, 29, 31, 32, 37, 43, 43-10T, 51, 54, 55R.1, 56, 56RR2, 57, 58, 59.1, 60, 63, Aehl, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aizl, AI-K-I, B, BCJAI, BCI, BC2, BLLI, BLI, BP142, BSLI, BSL2, BSI, BS3, BS8, BS15, BS18, BS22, BS26, BS28, BS31, BS104, BS105, BS106, BTB, B1715V1, C, CK-I, Coll, Corl, CP-53, CS-I, CSi, D, D, D, D5, entl, FPB, FP9, FSi, FS2, FS3, FS5, FS8, FS9, G, GH8, GT8, GV-I, GV-2, GT-4, g3, gl2, gl3, gl4, gl6, gl7, g21, g23, g24, g29, H2, kenl, KK-88, Kuml, Kyul, J7W-1, LP52, (syn=LP-52), L7, Mexl, MJ-I, mor2, MP-7, MPIO, MP12, MP14, MP15, Neol, No. 2, N5, N6P, PBCI, PBLA, PBPI, P2, S-a, SF2, SF6, Shal, Sill, SP02, (syn=φSPP1), SPβ, STI, STi, SU-11, t, Tbl, Tb2, Tb5, TblO, Tb26, Tb51, Tb53, Tb55, Tb77, Tb97, Tb99, Tb560, Tb595, Td8, Td6, Tdl5, Tgl, Tg4, Tg6, Tg7, Tg9, TglO, TglI, Tgl3, Tgl5, Tg21, Tinl, Tin7, Ting, Tinl3, Tm3, Tocl, Togl, toll, TP-1, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, Yunl, α, γ, pll, φmed-2, φT, φμ-4, φ3T, φ75, φIO5, (syn=φIO5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), alel, ARI, AR2, AR3, AR7, AR9, Bace-11, (syn=11), Bastille, BLI, BL2, BL3, BL4, BL5, BL6, BL8, BL9, BP124, BS28, BS80, Ch, CP-51, CP-54, D-5, dart, dent, DP-7, entl, FoSi, FoS2, FS4, FS6, FS7, G, gall, gamma, GEI, GF-2, GSi, GT-1, GT-2, GT-3, GT-4, GT-5, GT-6, GT-7, GV-6, g15, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No. 1, N17, N19, PBSI, PKI, PMBI, PMB12, PMJI, S, SPOI, SP3, SP5, SP6, SP7, SP8, SP9, SPIO, SP-15, SP50, (syn=SP-50), SP82, SST, subl, SW, Tg8, TgI2, TgI3, TgI4, thul, thuΛ, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (*B. megateriwn*), 4 (*B. sphaericus*), AR13, BPP-IO, BS32, BS107, BI, B2, GA-1, GP-10, GV-3, GV-5, g8, MP20, MP27, MP49, Nf, PP5, PP6, SF5, TgI8, TP-I, Versailles, φI5, φ29, 1-97, 837/IV, mï-*Bacillus* (1), BatIO, BSLIO, BSLI I, BS6, BSI I, BS16, BS23, BSIOI, BS102, gI8, morl, PBLI, SN45, thu2, thu3, Tml, Tm2, TP-20, TP21, TP52, type F, type G, type IV, HN-BacMus (3), BLE, (syn=θc), BS2, BS4, BS5, BS7, BIO, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, SPa, type 1 and μ.

Bacteria of the genus *Bacteroides* can be infected by the following phages: crAss-phage, ad 12, Baf-44, Baf-48B, Baf-64, Bf-I, Bf-52, B40-8, FI, βI, φAI, φBrOI, φBrO2, 11, 67.1, 67.3, 68.1, mt-*Bacteroides* (3), Bf42, Bf71, HN-Bdellovibrio (1) and BF-41.

Bacteria of the genus *Bordetella* can be infected by the following phages: 134 and NN-*Bordetella* (3).

Bacteria of the genus *Borrellia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=F01), (syn=FQI), D, FP2, (syn=FP2), (syn=FD2), Fz, (syn=Fz75/13), (syn=Firenze 75/13), (syn=Fi), Fi, (syn=FI), Fim, (syn=Flm), (syn=Fim), FiU, (syn=FIU), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn=F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=Fi0), (syn=FIO), 371/XXIX, (syn=371), (syn=Fn), (syn=FI I) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phage: Chpl.

Bacteria of the genus *Clostridium* can be infected by the following phages: CAKI, CAS, Ca7, CEβ, (syn=10), CEγ, CIdI, c-n71, c-203 Tox-, DER, (syn=ID), (syn=IDt0X+), HM3, KMI, KT, Ms, NAI, (syn=Naltox+), PA135Oe, Pfó, PL73, PL78, PL81, PI, P50, P5771, P19402, ICtOX+, 2CtOX\ 2D3 (syn=2Dt0X+), 3C, (syn=3Ctox+), 4C, (syn=4CtOX+), 56, III-I, NN-*Clostridium* (61), NBItOX+, αI, CAI, HMT, HM2, PFIS P-23, P-46, Q-05, Q-oe, Q-16, Q-21, Q-26, Q-40, Q-46, S111, SA02, WA01, WA03, Wm, W523, 80, C, CA2, CA3, CPTI, CPT4, cl, c4, c5, HM7, H11/A1, H18/Ax, FWS23, Hi58ZA1, K2ZA1, K21ZS23, ML, NA2tOX; Pf2, Pf3, Pf4, S9ZS3, S41ZA1, S44ZS23, α2, 41, 112ZS23, 214/S23, 233/Ai, 234/S23, 235/S23, II-1, 11-2, 11-3, NN-*Clostridium* (12), CAI, FI, K, S2, 1, 5 and NN-*Clostridium* (8).

Bacteria of the genus *Corynebacterium* can be infected by the following phages: CGKI (defective), A, A2, A3, AIOI, A128, A133, A137, A139, A155, A182, B, BF, B17, B18, B51, B271, B275, B276, B277, B279, B282, C, capi, CCI, CGI, CG2, CG33, CL31, Cog, (syn=CG5), D, E, F, H, H-I, hqi, hq2, 11ZH33, li/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ-), γI9, δ, (syn=δ'ox+), p, (syn=ptoχ-), φ9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phage: DF78, FI, F2, 1, 2, 4, 14, 41, 867, DI, SB24, 2BV, 182, 225, C2, C2F, E3, E62, DS96, H24, M35, P3, P9, SBIOI, S2, 2B11, 5, 182a, 705, 873, 881, 940, 1051, 1057, 21096C, NN-*Enterococcus* (1), PEI, FI, F3, F4, VD13, 1, 200, 235 and 341.

Bacteria of the genus *Erysipelothrix* can be infected by the following phage: NN-Eiysipelothrix (1).

Bacteria of the genus *Escherichia* can be infected by the following phages: BW73, B278, D6, D108, E, EI, E24, E41, FI-2, FI-4, FI-5, H18A, Ff18B, i, MM, Mu, (syn=mu), (syn=Mul), (syn=Mu-l), (syn=MU-l), (syn=Mul), (syn=μ), 025, Phl-5, Pk, PSP3, PI, PID, P2, P4 (defective), SI, Wφ, φK13, φR73 (defective), φI, φ2, φ7, φ92, ψ (defective), 7A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FII, FI3, H, HI, H3, H8, K3, M, N, ND-2, ND-3, ND4, ND-5, ND6, ND-7, Ox-1 (syn=OXI), (syn=HF), Ox-2 (syn=0×2), (syn=0X2), Ox-3, Ox-4, Ox-5, (syn=0X5), Ox-6, (syn=66F), (syn=φ66t), (syn=φ66t−)5 0111, Phl-I, RB42, RB43, RB49, RB69, S, Sal-I, Sal-2, Sal-3, Sal-4, Sal-5, Sal-6, TC23, TC45, TuII*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, αI, 1, IA, 3, (syn=Ac3), 3A, 3T+, (syn=3), (syn=MI), 5φ, (syn=φ5), 9266Q, CFO103, HK620, J, K, KIF, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, φ04-CF, φ05, φ06, φ07, φI, φI.2, φ20, φ95, φ263, φIO92, φI, φII, (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, CI, DDUP, ECI, EC2, E21, E29, FI, F26S, F27S, Hi, HK022, HK97, HK139, HK253, (syn=φHK97), HK256, K7, ND-1, no. D, PA-2, q, S2, TI, (syn=α), (syn=P28), (syn=T-I), (syn=Tx), T3C, T5, (syn=T-5), (syn=T5), UC-I, w, β4, γ2, λ (syn=lambda), (syn=φλ), φD326, φγ, φ06, φ7, φ10, φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J, 933H, O157 typing phages 1 to 16, JES-2013, 121Q, 172-1, 1720a-02, ADB-2, AKFV33, av-05, bV_EcoS_AHP42, bV_EcoS_AHP24, bC_EcoS_AHS24, bV_EcoS_AKS96, CBA120.

Bacteria of the genus *Fusobacterium* are infected by the following phage: NN-*Fusobacterium* (2), fv83-554/3, fv88-531/2, 227, fv2377, fv2527 and fv8501.

Bacteria of the genus *Haemophilus* are infected by the following phage: HPI, S2 and N3.

Bacteria of the genus *Helicobacter* are infected by the following phage: HPI and ^^-*Helicobacter* (1).

Bacteria of the genus *Klebsiella* are infected by the following phage: A10-2, KI4B, KI6B, K19, (syn=K19), K114, K115, K121, K128, K129, K132, K133, K135, KI106B, KI171B, KI181B, KI832B, AIO-I, AO-1, AO-2, AO-3, FC3-10, K, KI1, (syn=KII), KI2, (syn=K12), KI3, (syn=K13), (syn=KI 70/11), KI4, (syn=K14), KI5, (syn=K15), KI6, (syn=K16), KI7, (syn=K17), KI8, (syn=K18), KI9, (syn=K19), KI27, (syn=K127), KI31, (syn=K131), KI35, KI171B, II, VI, IX, CI-I, KI4B, KI8, KI11, K112, K113, K116, K117, K118, K120, K122, K123, K124, K126, K130, K134, KI106B, KIi65B, KI328B, KLXI, K328, P5046, 11, 380, III, IV, VII, VIII, FC3-11, KI2B, (syn=K12B), K125, (syn=K125), KI42B, (syn=K142), (syn=K142B), KI181B, (syn=KII 81), (syn=K1181B), K1765/I, (syn=K1765/1), KI842B, (syn=K1832B), KI937B, (syn=K1937B), LI, φ28, 7, 231, 483, 490, 632 and 864/100.

Bacteria of the genus *Lepitospira* are infected by the following phage: LEI, LE3, LE4 and ~NN-*Leptospira* (1).

Bacteria of the genus *Listeria* are infected by the following phage: A511, 01761, 4211, 4286, (syn=BO54), A005, A006, A020, A500, A502, A511, AI 18, A620, A640, B012, B021, B024, B025, B035, B051, B053, B054, B055, B056, BIOI, BI IO, B545, B604, B653, C707, D441, HSO47, HIOG, H8/73, H19, H21, H43, H46, H107, H108, HI 10, H163/84, H312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-Lisferia (15).

Bacteria of the genus *Morganella* are infected by the following phage: 47.

Bacteria of the genus *Mycobacterium* are infected by the following phage: 13, AGI, ALi, ATCC 11759, A2, B.C3, BG2, BKI, BKS, *butyricum*, B-I, B5, B7, B30, B35, Clark, CI, C2, DNAIII, DSP1, D4, D29, GS4E, (syn=GS4E), GS7, (syn=GS-7), (syn=GS7), IPa, lacticola, Legendre, Leo, L5, (syn=φL-5), MC-I, MC-3, MC-4, minetti, MTPHI I, Mx4, MyF3P/59a, phlei, (syn=phlei 1), phlei 4, Polonus II, rabinovitschi, smegmatis, TM4, TM9, TMIO, TM20, Y7, YIO, φ630, IB, IF, IH, 1/1, 67, 106, 1430, BI, (syn=Bol), B24, D, D29, F-K, F-S, HP, Polonus I, Roy, RI, (syn=RI-Myb), (syn=Ri), 11, 31, 40, 50, 103a, 103b, 128, 3111-D, 3215-D and NN-*Mycobacterium* (1).

Bacteria of the genus *Neisseria* are infected by the following phage: Group I, group II and NPI.

Bacteria of the genus *Nocardia* are infected by the following phage: MNP8, NJ-L, NS-8, N5 and TtiN-*Nocardia*.

Bacteria of the genus *Proteus* are infected by the following phage: Pm5, 13vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmlO, Pml I, Pv2, πI, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* are infected by the following phage: PL25, PL26, PL37, 9211/9295, 9213/921 Ib, 9248, 7/R49, 7476/322, 7478/325, 7479, 7480, 9000/9402 and 9213/921 Ia.

Bacteria of the genus *Pseudomonas* are infected by the following phage: Pfl, (syn=Pf-I), Pf2, Pf3, PP7, PRRI, 7s, im-*Pseudomonas* (1), AI-1, AI-2, B 17, B89, CB3, Col 2, Col 11, Col 18, Col 21, C154, C163, C167, C2121, E79, F8, ga, gb, H22, K1, M4, N2, Nu, PB-I, (syn=PBI), pfI6, PMN17, PPI, PP8, Psal, PsPI, PsP2, PsP3, PsP4, PsP5, PS3, PS17, PTB80, PX4, PX7, PYOI, PYO2, PYO5, PYO6, PYO9, PYOIO, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, PIK, SLPI, SL2, S2, UNL-I, wy, Yai, Ya4, Yan, φBE, φCTX, φC17, φKZ, (syn=φKZ), φ-LT, φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-1, C1-2, C5, D, gh-1, FI 16, HF, H90, K5, K6, KI 04, K109, K166, K267, N4, N5, O6N-25P, PE69, Pf, PPN25, PPN35, PPN89, PPN91, PP2, PP3, PP4, PP6, PP7, PP8, PP56, PP87, PPI 14, PP206, PP207, PP306, PP651, Psp231a, Pssy401, Pssy9220, psi, PTB2, PTB20, PTB42, PXI, PX3, PXIO, PX12, PX14, PYO70, PYO71, R, SH6, SH133, tf, Ya5, Ya7, φBS, φPKf77, φ-MC, φmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, FIO, g, gd, ge, gξ, Hwl2, Jb 19, KFI, L°, OXN-32P, O6N-52P, PCH-I, PC13-1, PC35-1, PH2, PH51, PH93, PH132, PMW, PM13, PM57, PM61, PM62, PM63, PM69, PM105, PMI 13, PM681, PM682, PO4, PPI, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-IO, Pz, SDI, SLI, SL3, SL5, SM, φC5, φCI I, φCI I-1, φC13, φC15, φMO, φX, φO4, φI I, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), G101, M6, M6a, LI, PB2, Pssyl5, Pssy4210, Pssy4220, PYO12, PYO34, PYO49, PYO50, PYO51, PYO52, PYO53, PYO57, PYO59, PYO200, PX2, PX5, SL4, φO3, φO6 and 1214.

Bacteria of the genus *Rickettsia* are infected by the following phage: NN-*Rickettsia*.

Bacteria of the genus *Salmonella* are infected by the following phage: b, Beccles, CT, d, Dundee, f, Fels 2, GI, GUI, GVI, GVIII, k, K, i, j, L, 01, (syn=0-1), (syn=O1), (syn=O-I), (syn=7), 02, 03, P3, P9a, PIO, Sab3, Sab5, SanIS, SanI7, SI, Taunton, Vil, (syn=Vil), 9, im*Salmonella* (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22al, P22-4, P22-7, P22-11, SNT-I, SNT-2, SP6, Villi, VilV, ViV, ViVI, ViVII, Worksop, Sj5, c34, 1,37, 1(40), (syn=φI[40]), 1, 422, 2, 2.5, 3b, 4, 5, 6,14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, GI 73, h, IRA, Jersey, MB78, P22-1, P22-3, P22-12, SabI, Sab2, Sab2, Sab4, SanI, San2, San3, San4, San6, San7, Sang, San9, SanI3, SanI4, SanI6, SanI8, SanI9, San20, San21, San22, San23, San24, San25, San26, SasLI, SasL2, SasL3, SasL4, SasL5, SIBL, SII, ViII, φI, 1, 2, 3a, 3al, 1010, Ym-*Salmonella* (1), N-4, SasL6 and 27.

Bacteria of the genus *Serratia* are infected by the following phage: A2P, PS20, SMB3, SMP, SMP5, SM2, V40, V56, ic, φCP-3, φCP-6, 3M, 10/Ia, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCWI, φCP6-1, φCP6-2, φCP6-5, 3T, 5, 8, 9F, 10/1, 20E, 32/6, 34B, 34CT, 34P, 37, 41, 56, 56D, 56P, 60P, 61/6, 74/6, 76/4, 101/8900, 226, 227, 228, 229F, 286, 289, 290F, 512, 764a, 2847/10, 2847/10a, L.359 and SMBI.

Bacteria of the genus *Shigella* are infected by the following phage: Fsa, (syn=a), FSD2d, (syn=D2d), (syn=W2d), FSD2E, (syn=W2e), fv, F6, f7.8, H-Sh, PES, P90, SfII, Sh, SHm, SHrv, (syn=HIV), SHvi, (syn=HVI), SHVvm, (syn=HVIII), SKγ66, (syn=gamma 66), (syn=yββ), (syn=γ66b), SKm, (syn=SIIIb)5 (syn=UI), SKw, (syn=Siva), (syn=IV), SIC™, (syn=SIVA.), (syn=IVA), SKvi, (syn=KVI), (syn=Svi), (syn=VI), SKvm, (syn=Svm), (syn=VIII), SKVπIA, (syn=SvmA), (syn=VIIIA), STvi, STK, STx1, STxn, S66, W2, (syn=D2c), (syn=D20), φI, φIVb 3-SO-R, 8368-SO-R, F7, (syn=FS7), (syn=K29), FIO, (syn=FSIO), (syn=K31), 11, (syn=alfa), (syn=FSa), (syn=KI 8), (syn=α), 12, (syn=a), (syn=K19), SG33, (syn=G35), (syn=SO-35/G), SG35, (syn=SO-55/G), SG3201, (syn=SO-3201/G), SHn, (syn=HIII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO—S-R), W1, (syn=D8), (syn=FSD8), W2a, (syn=D2A), (syn=FS2a), DD-2, Sf6, FSi, (syn=FI), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssγ66), φ2, BII, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI I, P2-SO-S, SG36, (syn=SO-36/G), (syn=G36), SG3204, (syn=SO-3204/G), SG3244, (syn=SO-3244/G), SHi, (syn=HI), SHvrr, (syn=HVII), SHK, (syn=HIX), SHx1, SHxrr, (syn=HXn), SKI, KI, (syn=S1), (syn=Ssl), SKVII, (syn=KVII), (syn=Svrr), (syn=SsVII), SKIX, (syn=KIX), (syn=S1x), (syn=SsIX), SKXII, (syn=KXII), (syn=Sxn), (syn=SsXII), STi, STfI, STrv, STVi, STvrr, S70, S206, U2-SO-S, 3210-SO-S, 3859-SO-S, 4020-SO-S, φ3, φ5, φ7, φ8, φ9, φIO, φI I, φI3, φI4, φI8, SHm, (syn=Hπi), SHχi, (syn=HXt) and SKxI, (syn=KXI), (syn=Sχi), (syn=SsXI), (syn=XI).

Bacteria of the genus *Staphylococcus* are infected by the following phage: A, EW, K, Ph5, Ph9, PhIO, PhI3, PI, P2, P3, P4, P8, P9, PIO, RG, SB-i, (syn=Sb-I), S3K, Twort, φSK311, φ812, 06, 40, 58, 119, 130, 131, 200, 1623, STCI, (syn=stcl), STC2, (syn=stc2), 44AHJD, 68, ACI, AC2, A6"C", A9"C", b581, CA-I, CA-2, CA-3, CA-4, CA-5, DI I, L39×35, L54a, M42, NI, N2, N3, N4, N5, N7, N8, NIO, Ni I, N12, N13, N14, N16, Ph6, Phl2, Phl4, UC-18, U4, U15, SI, S2, S3, S4, S5, X2, Z1, φB5-2, φD, ω, 11, (syn=φI I), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80a, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, AIO, A13, b594n, D, HK2, N9, N15, P52, P87, SI, S6, Z4, φRE, 3A, 3B, 3C, 6, 7, 16, 21, 42B, 42C, 42E, 44, 47, 47A5 47C, 51, 54, 54×1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phage: EJ-I, NN-Streptococais (1), a, Cl, FL0Ths, H39, Cp-I, Cp-5, Cp-7, Cp-9, Cp-IO, AT298, A5, alO/JI, alO/J2, alO/J5, alO/J9, A25, BTI I, b6, CAI, c20-1, c20-2, DP-1, Dp-4, DTI, ET42, eIO, FA101, FETHs, $F_K$, FKKIOI, FKLIO, FKP74, FKH, FLOTHs, FyIOI, fl, F10, F20140/76, g, GT-234, HB3, (syn=HB-3), HB-623, HB-746, M102, O1205, φO1205, PST, PO, P1, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, SfII 1, (syn=SFil I), (syn=φSFil I), (syn=φSfil I), (syn=φSfil I), sfil9, (syn=SFil9), (syn=φSFil9), (syn=φSfil9), Sfi21, (syn=SFi21), (syn=φSFi21), (syn=φSfi21), ST0, STX, st2, ST2, ST4, S3, (syn=φS3), s265, φ17, φ42, φ57, φ80, φ81, φ82, φ83, φ84, φ85, φ86, φ87, φ88, φ89, φ90, φ91, φ92, φ93, φ94, φ95, φ96, φ97, φ98, φ99, φIOO, φIOI, φIO2, φ227, φ7201, ωI, ω2, ω3, ω4, ω5, ω6, ω8, ωIO, 1, 6, 9, 10F, 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/ST16, 80/15, 80/47, 80/48, 101, 103/39, 103/40, 121/41, 121/42, 123/43, 123/44, 124/44, 337/ST17 and mStreptococcus (34).

Bacteria of the genus *Treponema* are infected by the following phage: NN-*Treponema* (1).

Bacteria of the genus *Vibrio* are infected by the following phage: CTXφ, fs, (syn=si), fs2, Ivpf5, Vfl2, Vf33, VPRP, VSK, v6, 493, CP-TI, ET25, kappa, K139, Labol, XN-69P, OXN-86, O6N-21P, PB-I, P147, rp-1, SE3, VA-1, (syn=VcA-I), VcA-2, VPI, VP2, VP4, VP7, VP8, VP9, VPIO, VP17, VP18, VP19, X29, (syn=29 d'Herelle), φHAWI-1, φHAWI-2, φHAWI-3, φHAWI-4, φHAWI-5, φHAWI-6, φHAWI-7, φHAWI-8, φHAWI-9, φHAWI-10, φHCI-1, φHC1-2, φHC1-3, φHC1-4, φHC2-1, >HC2-2, φHC2-3, φHC2-4, φHC3-1, φHC3-2, φHC3-3, φHD1S-1, φHD1S-2, φHD2S-1, φHD2S-2, φHD2S-3, φHD2S-4, φHD2S-5, φHDO-1, φHDO-2, φHDO-3, φHDO-4, φHDO-5, φHDO-6, φKL-33, φKL-34, φKL-35, φKL-36, φKWH-2, φKWH-3, φKWH-4, φMARQ-1, φMARQ-2, φMARQ-3, φMOAT-1, φO139, φPEL1A-1, φPEL1A-2, φPEL8A-1, φPEL8A-2, φPEL8A-3, φPEL8C-1, φPEL8C-2, φPEL13A-1, φPEL13B-1, φPEL13B-2, φPEL13B-3, φPEL13B-4, φPEL13B-5, φPEL13B-6, φPEL13B-7, φPEL13B-8, φPEL13B-9, φPEL13B-10, φVP143, φVP253, φ16, φI38, 1-II, 5, 13, 14, 16, 24, 32, 493, 6214, 7050, 7227, II, (syn=group II), (syn==φ2), V, VIII, ~m-*Vibrio* (13), KVP20, KVP40, nt-1, O6N-22P, P68, eI, e2, e3, e4, e5, FK, G, I, K, nt-6, NI, N2, N3, N4, N5, O6N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, I (syn=group I), III (syn=group III), VI, (syn=A-Saratov), VII, IX, X, HN-*Vibrio* (6), pAI, 7, 7-8, 70A-2, 71A-6, 72A-5, 72A-8, 108A-10, 109A-6, 109A-8, IIOA-1, 110A-5, 110A-7, hv-1, OXN-52P, P13, P38, P53, P65, P108, PiII, TPI3 VP3, VP6, VP12, VP13, 70A-3, 70A-4, 70A-10, 72A-1, 108A-3, 109-B1, 110A-2, 149, (syn=φI49), IV, (syn=group IV), NN-*Vibrio* (22), VP5, VPII, VP15, VP16, αI, α2, α3a, α3b, 353B and HN-*Vibrio* (7).

Bacteria of the genus *Yersinia* are infected by the following phage: H, H-1, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φYerO3-12, 3, 4/C1324-76, 7/F783-76, 903, 1/M6176 and Yer2AT.

More preferably, the bacteriophage is selected in the group consisting of *Salmonella* virus SKML39, *Shigella* virus AG3, *Dickeya* virus Limestone, *Dickeya* virus RC2014, *Escherichia* virus CBA120, *Escherichia* virus Phaxl, *Salmonella* virus 38, *Salmonella* virus Det7, *Salmonella* virus GG32, *Salmonella* virus PM10, *Salmonella* virus SFP10, *Salmonella* virus SH19, *Salmonella* virus SJ3, *Escherichia* virus ECML4, *Salmonella* virus Marshall, *Salmonella* virus Maynard, *Salmonella* virus SJ2, *Salmonella* virus STML131, *Salmonella* virus Vil, *Erwinia* virus Ea2809, *Klebsiella* virus 0507KN21, *Serratia* virus IME250, *Serratia* virus MAM1, *Campylobacter* virus CP21, *Campylobacter* virus CP220, *Campylobacter* virus CPt10, *Campylobacter* virus IBB35, *Campylobacter* virus CP81, *Campylobacter* virus CP30A, *Campylobacter* virus CPX, *Campylobacter* virus NCTC12673, *Erwinia* virus Ea214, *Erwinia* virus M7, *Escherichia* virus AYO145A, *Escherichia* virus EC6, *Escherichia* virus HY02, *Escherichia* virus JH2, *Escherichia* virus TP1, *Escherichia* virus VpaE1, *Escherichia* virus wV8, *Salmonella* virus FelixO1, *Salmonella* virus HB2014, *Salmonella* virus Mushroom, *Salmonella* virus UAB87, *Citrobacter* virus Moogle, *Citrobacter* virus Mordin, *Escherichia* virus SUSP1, *Escherichia* virus SUSP2, *Aeromonas* virus phiO18P, *Haemophilus* virus HP1, *Haemophilus* virus HP2, *Pasteurella* virus F108, *Vibrio* virus K139, *Vibrio* virus Kappa, *Burkholderia* virus phi52237, *Burkholderia* virus phiE122, *Burkholderia* virus phiE202, *Escherichia* virus 186, *Escherichia* virus P4, *Escherichia* virus P2, *Escherichia* virus Wphi, *Mannheimia* virus PHL101, *Pseudomonas* virus phiCTX, *Ralstonia* virus RSA1, *Salmonella* virus Fels2, *Salmonella* virus PsP3, *Salmonella* virus SopEphi, *Yersinia* virus L413C, *Staphylococcus* virus G1, *Staphylococcus* virus G15, *Staphylococcus* virus JD7, *Staphylococcus* virus K, *Staphylococcus* virus MCE2014, *Staphylococcus* virus P108, *Staphylococcus* virus Rodi, *Staphylococcus* virus S253, *Staphylococcus* virus S25-4, *Staphylococcus* virus SA12, *Listeria* virus A511, *Listeria* virus P100, *Staphylococcus* virus Remus, *Staphylococcus* virus SA11, *Staphylococcus* virus Stau2, *Bacillus* virus Camphawk, *Bacillus* virus SPO1, *Bacillus* virus BCP78, *Bacillus* virus TsarBomba, *Staphylococcus* virus Twort, *Enterococcus* virus phiEC24C, *Lactobacillus* virus Lb338-1, *Lactobacillus* virus LP65, *Enterobacter* virus PG7, *Escherichia* virus CC31, *Klebsiella* virus JD18, *Klebsiella* virus PKO111, *Escherichia* virus Bp7, *Escherichia* virus IME08, *Escherichia* virus JS10, *Escherichia* virus JS98, *Escherichia* virus QL01, *Escherichia* virus VR5, *Enterobacter* virus Eap3, *Klebsiella* virus KP15, *Klebsiella* virus KP27, *Klebsiella* virus Matisse, *Klebsiella* virus Miro, *Citrobacter* virus Merlin, *Citrobacter* virus Moon, *Escherichia* virus JSE, *Escherichia* virus phi1, *Escherichia* virus RB49, *Escherichia* virus HX01, *Escherichia* virus J509, *Escherichia* virus RB69, *Shigella* virus UTAM, *Salmonella* virus S16, *Salmonella* virus STML198, *Vibrio* virus KVP40, *Vibrio* virus nt1, *Vibrio* virus ValKK3, *Escherichia* virus VR7, *Escherichia* virus VR20, *Escherichia* virus VR25,

*Escherichia* virus VR26, *Shigella* virus SP18, *Escherichia* virus AR1, *Escherichia* virus C40, *Escherichia* virus E112, *Escherichia* virus ECML134, *Escherichia* virus HY01, *Escherichia* virus Ime09, *Escherichia* virus RB3, *Escherichia* virus RB14, *Escherichia* virus T4, *Shigella* virus Pss1, *Shigella* virus Shfl2, *Yersinia* virus D1, *Yersinia* virus PST, *Acinetobacter* virus 133, *Aeromonas* virus 65, *Aeromonas* virus Aeh1, *Escherichia* virus RB16, *Escherichia* virus RB32, *Escherichia* virus RB43, *Pseudomonas* virus 42, *Cronobacter* virus CR3, *Cronobacter* virus CR8, *Cronobacter* virus CR9, *Cronobacter* virus PBES02, *Pectobacterium* virus phiTE, *Cronobacter* virus GAP31, *Escherichia* virus 4MG, *Salmonella* virus SE1, *Salmonella* virus SSE121, *Escherichia* virus FFH2, *Escherichia* virus FV3, *Escherichia* virus JES2013, *Escherichia* virus V5, *Brevibacillus* virus Abouo, *Brevibacillus* virus Davies, *Bacillus* virus Agate, *Bacillus* virus Bobb, *Bacillus* virus Bp8pC, *Erwinia* virus Deimos, *Erwinia* virus Ea35-70, *Erwinia* virus RAY, *Erwinia* virus Simmy50, *Erwinia* virus SpecialG, *Acinetobacter* virus AB1, *Acinetobacter* virus AB2, *Acinetobacter* virus AbC62, *Acinetobacter* virus AP22, *Arthrobacter* virus ArV1, *Arthrobacter* virus Trina, *Bacillus* virus AvesoBmore, *Bacillus* virus B4, *Bacillus* virus Bigbertha, *Bacillus* virus Riley, *Bacillus* virus Spock, *Bacillus* virus Troll, *Bacillus* virus Bastille, *Bacillus* virus CAM003, *Bacillus* virus Bc431, *Bacillus* virus Bcp1, *Bacillus* virus BCP82, *Bacillus* virus BM15, *Bacillus* virus Deepblue, *Bacillus* virus JBP901, *Burkholderia* virus Bcep1, *Burkholderia* virus Bcep43, *Burkholderia* virus Bcep781, *Burkholderia* virus BcepNY3, *Xanthomonas* virus OP2, *Burkholderia* virus BcepMu, *Burkholderia* virus phiE255, *Aeromonas* virus 44RR2, *Mycobacterium* virus Alice, *Mycobacterium* virus Bxz1, *Mycobacterium* virus Dandelion, *Mycobacterium* virus HyRo, *Mycobacterium* virus 13, *Mycobacterium* virus Nappy, *Mycobacterium* virus Sebata, *Clostridium* virus phiC2, *Clostridium* virus phiCD27, *Clostridium* virus phiCD119, *Bacillus* virus CP51, *Bacillus* virus JL, *Bacillus* virus Shanette, *Escherichia* virus CVM10, *Escherichia* virus ep3, *Erwinia* virus Asesino, *Erwinia* virus EaH2, *Pseudomonas* virus EL, *Halomonas* virus HAP1, *Vibrio* virus VP882, *Brevibacillus* virus Jimmer, *Brevibacillus* virus Osiris, *Pseudomonas* virus Ab03, *Pseudomonas* virus KPP10, *Pseudomonas* virus PAKP3, *Sinorhizobium* virus M7, *Sinorhizobium* virus M12, *Sinorhizobium* virus N3, *Erwinia* virus Machina, *Arthrobacter* virus Brent, *Arthrobacter* virus Jawnski, *Arthrobacter* virus Martha, *Arthrobacter* virus Sonny, *Edwardsiella* virus MSW3, *Edwardsiella* virus PEi21, *Escherichia* virus Mu, *Shigella* virus SfMu, *Halobacterium* virus phiH, *Bacillus* virus Grass, *Bacillus* virus NIT1, *Bacillus* virus SPG24, *Aeromonas* virus 43, *Escherichia* virus P1, *Pseudomonas* virus CAb1, *Pseudomonas* virus CAb02, *Pseudomonas* virus JG004, *Pseudomonas* virus PAKP1, *Pseudomonas* virus PAKP4, *Pseudomonas* virus PaP1, *Burkholderia* virus BcepF1, *Pseudomonas* virus 141, *Pseudomonas* virus Ab28, *Pseudomonas* virus DL60, *Pseudomonas* virus DL68, *Pseudomonas* virus F8, *Pseudomonas* virus JG024, *Pseudomonas* virus KPP12, *Pseudomonas* virus LBL3, *Pseudomonas* virus LMA2, *Pseudomonas* virus PB1, *Pseudomonas* virus SN, *Pseudomonas* virus PA7, *Pseudomonas* virus phiKZ, *Rhizobium* virus RHEph4, *Ralstonia* virus RSF1, *Ralstonia* virus RSL2, *Ralstonia* virus RSL1, *Aeromonas* virus 25, *Aeromonas* virus 31, *Aeromonas* virus Aes12, *Aeromonas* virus Aes508, *Aeromonas* virus AS4, *Stenotrophomonas* virus IME13, *Staphylococcus* virus IPLAC1C, *Staphylococcus* virus SEP1, *Salmonella* virus SPN3US, *Bacillus* virus 1, *Geobacillus* virus GBSV1, *Yersinia* virus R1RT, *Yersinia* virus TG1, *Bacillus* virus G, *Bacillus* virus PBS1, *Microcystis* virus Ma-LMM01, *Vibrio* virus MAR, *Vibrio* virus VHML, *Vibrio* virus VP585, *Bacillus* virus BPS13, *Bacillus* virus Hakuna, *Bacillus* virus Megatron, *Bacillus* virus WPh, *Acinetobacter* virus AB3, *Acinetobacter* virus Abp1, *Acinetobacter* virus Fri1, *Acinetobacter* virus IME200, *Acinetobacter* virus PD6A3, *Acinetobacter* virus PDAB9, *Acinetobacter* virus phiAB1, *Escherichia* virus K30, *Klebsiella* virus K5, *Klebsiella* virus K11, *Klebsiella* virus Kp1, *Klebsiella* virus KP32, *Klebsiella* virus KpV289, *Klebsiella* virus F19, *Klebsiella* virus K244, *Klebsiella* virus Kp2, *Klebsiella* virus KP34, *Klebsiella* virus KpV41, *Klebsiella* virus KpV71, *Klebsiella* virus KpV475, *Klebsiella* virus SU503, *Klebsiella* virus SU552A, *Pantoea* virus Limelight, *Pantoea* virus Limezero, *Pseudomonas* virus LKA1, *Pseudomonas* virus phiKMV, *Xanthomonas* virus f20, *Xanthomonas* virus f30, *Xylella* virus Prado, *Erwinia* virus Era103, *Escherichia* virus K5, *Escherichia* virus K1-5, *Escherichia* virus K1E, *Salmonella* virus SP6, *Escherichia* virus T7, *Kluyvera* virus Kvp1, *Pseudomonas* virus gh1, *Prochlorococcus* virus PSSP7, *Synechococcus* virus P60, *Synechococcus* virus SynS, *Streptococcus* virus Cp1, *Streptococcus* virus Cp7, *Staphylococcus* virus 44AHJD, *Streptococcus* virus C1, *Bacillus* virus B103, *Bacillus* virus GA1, *Bacillus* virus phi29, *Kurthia* virus 6, *Actinomyces* virus Av1, *Mycoplasma* virus P1, *Escherichia* virus 24B, *Escherichia* virus 933W, *Escherichia* virus Min27, *Escherichia* virus PA28, *Escherichia* virus Stx2 II, *Shigella* virus 7502Stx, *Shigella* virus POCJ13, *Escherichia* virus 191, *Escherichia* virus PA2, *Escherichia* virus TL2011, *Shigella* virus VASD, *Burkholderia* virus Bcep22, *Burkholderia* virus Bcepil02, *Burkholderia* virus Bcepmigl, *Burkholderia* virus DC1, *Bordetella* virus BPP1, *Burkholderia* virus BcepC6B, *Cellulophaga* virus Cba41, *Cellulophaga* virus Cba172, *Dinoroseobacter* virus DFL12, *Erwinia* virus Ea9-2, *Erwinia* virus Frozen, *Escherichia* virus phiV10, *Salmonella* virus Epsilon15, *Salmonella* virus SPN1S, *Pseudomonas* virus F116, *Pseudomonas* virus H66, *Escherichia* virus APECS, *Escherichia* virus APEC7, *Escherichia* virus Bp4, *Escherichia* virus EC1UPM, *Escherichia* virus ECBP1, *Escherichia* virus G7C, *Escherichia* virus IME11, *Shigella* virus Sb1, *Achromobacter* virus Axp3, *Achromobacter* virus JWAlpha, *Edwardsiella* virus KF1, *Pseudomonas* virus KPP25, *Pseudomonas* virus R18, *Pseudomonas* virus Ab09, *Pseudomonas* virus LIT1, *Pseudomonas* virus PA26, *Pseudomonas* virus Ab22, *Pseudomonas* virus CHU, *Pseudomonas* virus LUZ24, *Pseudomonas* virus PAA2, *Pseudomonas* virus PaP3, *Pseudomonas* virus PaP4, *Pseudomonas* virus TL, *Pseudomonas* virus KPP21, *Pseudomonas* virus LUZ7, *Escherichia* virus N4, *Salmonella* virus 9NA, *Salmonella* virus SP069, *Salmonella* virus BTP1, *Salmonella* virus HK620, *Salmonella* virus P22, *Salmonella* virus ST64T, *Shigella* virus Sf6, *Bacillus* virus Page, *Bacillus* virus Palmer, *Bacillus* virus Pascal, *Bacillus* virus Pony, *Bacillus* virus Pookie, *Escherichia* virus 172-1, *Escherichia* virus ECB2, *Escherichia* virus NJ01, *Escherichia* virus phiEco32, *Escherichia* virus Septimall, *Escherichia* virus SU10, *Brucella* virus Pr, *Brucella* virus Tb, *Escherichia* virus Pollock, *Salmonella* virus FSL SP-058, *Salmonella* virus FSL SP-076, *Helicobacter* virus 1961P, *Helicobacter* virus KHP30, *Helicobacter* virus KHP40, *Hamiltonella* virus APSE1, *Lactococcus* virus KSY1, *Phormidium* virus WMP3, *Phormidium* virus WMP4, *Pseudomonas* virus 119X, *Roseobacter* virus SIO1, *Vibrio* virus VpV262, *Vibrio* virus VC8, *Vibrio* virus VP2, *Vibrio* virus VP5, *Streptomyces* virus Amela, *Streptomyces* virus phi- CAM, *Streptomyces* virus Aaronocolus, *Streptomyces* virus Caliburn, *Streptomyces* virus Danzina, *Streptomyces* virus Hydra, *Streptomyces* virus Izzy, *Streptomyces* virus Lannister, *Streptomyces* virus Lika, *Streptomyces* virus Sujidade, *Streptomyces* virus Zemlya, *Streptomyces* virus ELB20, *Streptomyces* virus R4, *Streptomyces* virus phiHau3, *Mycobacterium* virus Acadian, *Mycobacterium* virus Baee, *Mycobacterium* virus Reprobate, *Mycobacterium* virus Adawi, *Mycobacterium* virus Bane1, *Mycobacterium* virus BrownCNA, *Mycobacterium* virus Chrisnmich, *Mycobacterium* virus Cooper, *Mycobacterium* virus JAMaL, *Mycobacterium* virus Nigel, *Mycobacterium* virus Stinger, *Mycobacterium* virus Vincenzo, *Mycobacterium* virus Zemanar, *Mycobacterium* virus Apizium, *Mycobacterium* virus Manad, *Mycobacterium* virus Oline, *Mycobacterium* virus Osmaximus, *Mycobacterium* virus Pg1, *Mycobacterium* virus Soto, *Mycobacterium* virus Suffolk, *Mycobacterium* virus Athena, *Mycobacterium* virus Bernardo, *Mycobacterium* virus Gadjet, *Mycobacterium* virus Pipefish, *Mycobacterium* virus Godines, *Mycobacterium* virus Rosebush, *Mycobacterium* virus Babsiella, *Mycobacterium* virus Brujita, *Mycobacterium* virus Che9c, *Mycobacterium* virus Sbash, *Mycobacterium* virus Hawkeye, *Mycobacterium* virus Plot, *Salmonella* virus AG11, *Salmonella* virus Ent1, *Salmonella* virus f18SE, *Salmonella* virus Jersey, *Salmonella* virus L13, *Salmonella* virus LSPA1, *Salmonella* virus SE2, *Salmonella* virus SETP3, *Salmonella* virus SETP7, *Salmonella* virus SETP13, *Salmonella* virus SP101, *Salmonella* virus SS3e, *Salmonella* virus wksl3, *Escherichia* virus K1G, *Escherichia* virus K1H, *Escherichia* virus K1ind1, *Escherichia* virus K1ind2, *Salmonella* virus SP31, *Leuconostoc* virus Lmd1, *Leuconostoc* virus LN03, *Leuconostoc* virus LN04, *Leuconostoc* virus LN12, *Leuconostoc* virus LN6B, *Leuconostoc* virus P793, *Leuconostoc* virus 1A4, *Leuconostoc* virus Ln8, *Leuconostoc* virus Ln9, *Leuconostoc* virus LN25, *Leuconostoc* virus LN34, *Leuconostoc* virus LNTR3, *Mycobacterium* virus Bongo, *Mycobacterium* virus Rey, *Mycobacterium* virus Butters, *Mycobacterium* virus Michelle, *Mycobacterium* virus Charlie, *Mycobacterium* virus Pipsqueaks, *Mycobacterium* virus Xeno, *Mycobacterium* virus Panchino, *Mycobacterium* virus Phrann, *Mycobacterium* virus Redi, *Mycobacterium* virus Skinnyp, *Gordonia* virus BaxterFox, *Gordonia* virus Yeezy, *Gordonia* virus Kita, *Gordonia* virus Zirinka, *Gorrdonia* virus Nymphadora, *Mycobacterium* virus Bignuz, *Mycobacterium* virus Brusacoram, *Mycobacterium* virus Donovan, *Mycobacterium* virus Fishburne, *Mycobacterium* virus Jebeks, *Mycobacterium* virus Malithi, *Mycobacterium* virus Phayonce, *Enterobacter* virus F20, *Klebsiella* virus 1513, *Klebsiella* virus KLPN1, *Klebsiella* virus KP36, *Klebsiella* virus PKP126, *Klebsiella* virus Sushi, *Escherichia* virus AHP42, *Escherichia* virus AHS24, *Escherichia* virus AKS96, *Escherichia* virus C119, *Escherichia* virus E41c, *Escherichia* virus Eb49, *Escherichia* virus Jk06, *Escherichia* virus KP26, *Escherichia* virus Rogue1, *Escherichia* virus ACGM12, *Escherichia* virus Rtp, *Escherichia* virus ADB2, *Escherichia* virus JMPW1, *Escherichia* virus JMPW2, *Escherichia* virus T1, *Shigella* virus PSf2, *Shigella* virus Shfl1, *Citrobacter* virus Stevie, *Escherichia* virus TLS, *Salmonella* virus SP126, *Cronobacter* virus Esp2949-1, *Pseudomonas* virus Ab18, *Pseudomonas* virus Ab19, *Pseudomonas* virus PaMx11, *Arthrobacter* virus Amigo, *Propionibacterium* virus Anatole, *Propionibacterium* virus B3, *Bacillus* virus Andromeda, *Bacillus* virus Blastoid, *Bacillus* virus Curly, *Bacillus* virus Eoghan, *Bacillus* virus Finn, *Bacillus* virus Glittering, *Bacillus* virus Riggi, *Bacillus* virus Taylor, *Gordonia* virus Attis, *Mycobacterium* virus Barnyard, *Mycobacterium* virus Konstantine, *Mycobacterium* virus Predator, *Mycobacterium* virus Bernal13, *Staphylococcus* virus 13, *Staphylococcus* virus 77, *Staphylococcus* virus 108PVL, *Mycobacterium* virus Bron, *Mycobacterium* virus Faith1, *Mycobacterium* virus Joedirt, *Mycobacterium* virus Rumpelstiltskin, *Lactococcus* virus bIL67, *Lactococcus* virus c2, *Lactobacillus* virus c5, *Lactobacillus* virus Ld3, *Lactobacillus* virus Ld17, *Lactobacillus* virus Ld25A, *Lactobacillus* virus LLKu, *Lactobacillus* virus phiLdb, *Cellulophaga* virus Cba121, *Cellulophaga* virus Cba171, *Cellulophaga* virus Cba181, *Cellulophaga* virus ST, *Bacillus* virus 250, *Bacillus* virus IEBH, *Mycobacterium* virus Ardmore, *Mycobacterium* virus Avani, *Mycobacterium* virus Boomer, *Mycobacterium* virus Che8, *Mycobacterium* virus Che9d, *Mycobacterium* virus Deadp, *Mycobacterium* virus Dlane, *Mycobacterium* virus Dorothy, *Mycobacterium* virus Dotproduct, *Mycobacterium* virus Drago, *Mycobacterium* virus Fruitloop, *Mycobacterium* virus Gumbie, *Mycobacterium* virus Ibhubesi, *Mycobacterium* virus Llij, *Mycobacterium* virus Mozy, *Mycobacterium* virus Mutaforma13, *Mycobacterium* virus Pacc40, *Mycobacterium* virus PMC, *Mycobacterium* virus Ramsey, *Mycobacterium* virus Rockyhorror, *Mycobacterium* virus SG4, *Mycobacterium* virus Shaunal, *Mycobacterium* virus Shilan, *Mycobacterium* virus Spartacus, *Mycobacterium* virus Taj, *Mycobacterium* virus Tweety, *Mycobacterium* virus Wee, *Mycobacterium* virus Yoshi, *Salmonella* virus Chi, *Salmonella* virus FSLSP030, *Salmonella* virus FSLSP088, *Salmonella* virus iEPS5, *Salmonella* virus SPN19, *Mycobacterium* virus 244, *Mycobacterium* virus Bask21, *Mycobacterium* virus CJW1, *Mycobacterium* virus Eureka, *Mycobacterium* virus Kostya, *Mycobacterium* virus Porky, *Mycobacterium* virus Pumpkin, *Mycobacterium* virus Sirduracell, *Mycobacterium* virus Toto, *Mycobacterium* virus Corndog, *Mycobacterium* virus Firecracker, *Rhodobacter* virus RcCronus, *Pseudomonas* virus D3112, *Pseudomonas* virus DMS3, *Pseudomonas* virus FHA0480, *Pseudomonas* virus LPB1, *Pseudomonas* virus MP22, *Pseudomonas* virus MP29, *Pseudomonas* virus MP38, *Pseudomonas* virus PA1KOR, *Pseudomonas* virus D3, *Pseudomonas* virus PMG1, *Arthrobacter* virus Decurro, *Gordonia* virus Demosthenes, *Gordonia* virus Katyusha, *Gordonia* virus Kvothe, *Propionibacterium* virus B22, *Propionibacterium* virus Doucette, *Propionibacterium* virus E6, *Propionibacterium* virus G4, *Burkholderia* virus phi6442, *Burkholderia* virus phi1026b, *Burkholderia* virus phiE125, *Edwardsiella* virus eiAU, *Mycobacterium* virus Ff47, *Mycobacterium* virus Muddy, *Mycobacterium* virus Gaia, *Mycobacterium* virus Giles, *Arthrobacter* virus Captnmurica, *Arthrobacter* virus Gordon, *Gordonia* virus GordTnk2, *Paenibacillus* virus Harrison, *Escherichia* virus EK99P1, *Escherichia* virus HK578, *Escherichia* virus JL1, *Escherichia* virus SSL2009a, *Escherichia* virus YD2008s, *Shigella* virus EP23, *Sodalis* virus S01, *Escherichia* virus HK022, *Escherichia* virus HK75, *Escherichia* virus HK97, *Escherichia* virus HK106, *Escherichia* virus HK446, *Escherichia* virus HK542, *Escherichia* virus HK544, *Escherichia* virus HK633, *Escherichia* virus mEp234, *Escherichia* virus mEp235, *Escherichia* virus mEpX1, *Escherichia* virus mEpX2, *Escherichia* virus mEp043, *Escherichia* virus mEp213, *Escherichia* virus mEp237, *Escherichia* virus mEp390, *Escherichia* virus mEp460, *Escherichia* virus mEp505, *Escherichia* virus mEp506, *Brevibacillus* virus Jenst, *Achromobacter* virus 83-24, *Achromobacter* virus JWX, *Arthrobacter* virus Kellezzio, *Arthrobacter* virus Kitkat, *Arthrobacter* virus Bennie, *Arthrobacter* virus DrRobert, *Arthrobacter* virus Glenn, *Arthrobacter* virus HunterDalle, *Arthrobacter* virus Joann, *Arthrobacter* virus Korra, *Arthrobacter* virus Preamble, *Arthrobacter* virus Pumancara, *Arthrobacter* virus Wayne, *Mycobacterium* virus Alma, *Mycobacterium* virus Arturo, *Mycobacterium* virus Astro, *Mycobacterium* virus Backyardigan, *Mycobacterium* virus BBPiebs31, *Mycobacterium* virus Benedict, *Mycobacterium* virus Bethlehem, *Mycobacterium* virus Billknuckles, *Mycobacterium* virus Bruns, *Mycobacterium* virus Bxb1, *Mycobacterium* virus Bxz2, *Mycobacterium* virus Che12, *Mycobacterium* virus Cuco, *Mycobacterium* virus D29, *Mycobacterium* virus Doom, *Mycobacterium* virus Ericb, *Mycobacterium* virus Euphoria, *Mycobacterium* virus George, *Mycobacterium* virus Gladiator, *Mycobacterium* virus Goose, *Mycobacterium* virus Hammer, *Mycobacterium* virus Heldan, *Mycobacterium* virus Jasper, *Mycobacterium* virus JC27, *Mycobacterium* virus Jeffabunny, *Mycobacterium* virus JHC117, *Mycobacterium* virus KBG, *Mycobacterium* virus Kssjeb, *Mycobacterium* virus Kugel, *Mycobacterium* virus L5, *Mycobacterium* virus Lesedi, *Mycobacterium* virus LHTSCC, *Mycobacterium* virus lockley, *Mycobacterium* virus Marcell, *Mycobacterium* virus Microwolf, *Mycobacterium* virus Mrgordo, *Mycobacterium* virus Museum, *Mycobacterium* virus Nepal, *Mycobacterium* virus Packman, *Mycobacterium* virus Peaches, *Mycobacterium* virus Perseus, *Mycobacterium* virus Pukovnik, *Mycobacterium* virus Rebeuca, *Mycobacterium* virus Redrock, *Mycobacterium* virus Ridgecb, *Mycobacterium* virus Rockstar, *Mycobacterium* virus Saintus, *Mycobacterium* virus Skipole, *Mycobacterium* virus Solon, *Mycobacterium* virus Switzer, *Mycobacterium* virus SWU1, *Mycobacterium* virus Ta17a, *Mycobacterium* virus Tiger, *Mycobacterium* virus Timshel, *Mycobacterium* virus Trixie, *Mycobacterium* virus Turbido, *Mycobacterium* virus Twister, *Mycobacterium* virus U2, *Mycobacterium* virus Violet, *Mycobacterium* virus Wonder, *Escherichia* virus DE3, *Escherichia* virus HK629, *Escherichia* virus HK630, *Escherichia* virus Lambda, *Arthrobacter* virus Laroye, *Mycobacterium* virus Halo, *Mycobacterium* virus Liefie, *Mycobacterium* virus Marvin, *Mycobacterium* virus Mosmoris, *Arthrobacter* virus Circum, *Arthrobacter* virus Mudcat, *Escherichia* virus N15, *Escherichia* virus 9 g, *Escherichia* virus JenK1, *Escherichia* virus JenP1, *Escherichia* virus JenP2, *Pseudomonas* virus NP1, *Pseudomonas* virus PaMx25, *Mycobacterium* virus Baka, *Mycobacterium* virus Courthouse, *Mycobacterium* virus Littleo, *Mycobacterium* virus Omega, *Mycobacterium* virus Optimus, *Mycobacterium* virus Thibault, *Polaribacter* virus P12002L, *Polaribacter* virus P12002S, *Nonlabens* virus P12024L, *Nonlabens* virus P12024S, *Thermus* virus P23-45, *Thermus* virus P74-26, *Listeria* virus LP26, *Listeria* virus LP37, *Listeria* virus LP110, *Listeria* virus LP114, *Listeria* virus P70, *Propionibacterium* virus ATCC29399BC, *Propionibacterium* virus ATCC29399BT, *Propionibacterium* virus Attacne, *Propionibacterium* virus Keiki, *Propionibacterium* virus Kubed, *Propionibacterium* virus Lauchelly, *Propionibacterium* virus MrAK, *Propionibacterium* virus Ouroboros, *Propionibacterium* virus P91, *Propionibacterium* virus P105, *Propionibacterium* virus P144, *Propionibacterium* virus P1001, *Propionibacterium* virus P1.1, *Propionibacterium* virus P100A, *Propionibacterium* virus P100D, *Propionibacterium* virus P101A, *Propionibacterium* virus P104A, *Propionibacterium* virus PA6, *Propionibacterium* virus Pacnes201215, *Propionibacterium* virus PAD20, *Propionibacterium* virus PAS50, *Propionibacterium* virus PHLOO9M11, *Propionibacterium* virus PHL025M00, *Propionibacterium* virus PHL037M02, *Propionibacterium* virus PHL041M10, *Propionibacterium* virus PHL060L00, *Propionibacterium* virus PHL067M01, *Propionibacterium* virus PHL070N00, *Propionibacterium* virus PHL071N05, *Propionibacterium* virus PHL082M03, *Propionibacterium* virus PHL092M00, *Propionibacterium* virus PHL095N00, *Propionibacterium* virus PHL111M01, *Propionibacterium* virus PHL112N00, *Propionibacterium* virus PHL113M01, *Propionibacterium* virus PHL114L00, *Propionibacterium* virus PHL116M00, *Propionibacterium* virus PHL117M00, *Propionibacterium* virus PHL117M01, *Propionibacterium* virus PHL132N00, *Propionibacterium* virus PHL141N00, *Propionibacterium* virus PHL151M00, *Propionibacterium* virus PHL151N00, *Propionibacterium* virus PHL152M00, *Propionibacterium* virus PHL163M00, *Propionibacterium* virus PHL171M01, *Propionibacterium* virus PHL179M00, *Propionibacterium* virus PHL194M00, *Propionibacterium* virus PHL199M00, *Propionibacterium* virus PHL301M00, *Propionibacterium* virus PHL308M00, *Propionibacterium* virus Pirate, *Propionibacterium* virus Procrass1, *Propionibacterium* virus SKKY, *Propionibacterium* virus Solid, *Propionibacterium* virus Stormborn, *Propionibacterium* virus Wizzo, *Pseudomonas* virus PaMx28, *Pseudomonas* virus PaMx74, *Mycobacterium* virus Patience, *Mycobacterium* virus PBI1, *Rhodococcus* virus Pepy6, *Rhodococcus* virus Poco6, *Propionibacterium* virus PFR1, *Streptomyces* virus phiBT1, *Streptomyces* virus phiC31, *Streptomyces* virus TG1, *Caulobacter* virus Karma, *Caulobacter* virus Magneto, *Caulobacter* virus phiCbK, *Caulobacter* virus Rogue, *Caulobacter* virus Swift, *Staphylococcus* virus 11, *Staphylococcus* virus 29, *Staphylococcus* virus 37, *Staphylococcus* virus 53, *Staphylococcus* virus 55, *Staphylococcus* virus 69, *Staphylococcus* virus 71, *Staphylococcus* virus 80, *Staphylococcus* virus 85, *Staphylococcus* virus 88, *Staphylococcus* virus 92, *Staphylococcus* virus 96, *Staphylococcus* virus 187, *Staphylococcus* virus 52a, *Staphylococcus* virus 80alpha, *Staphylococcus* virus CNPH82, *Staphylococcus* virus EW, *Staphylococcus* virus IPLA5, *Staphylococcus* virus IPLA7, *Staphylococcus* virus IPLA88, *Staphylococcus* virus PH15, *Staphylococcus* virus phiETA, *Staphylococcus* virus phiETA2, *Staphylococcus* virus phiETA3, *Staphylococcus* virus phiMR11, *Staphylococcus* virus phiMR25, *Staphylococcus* virus phiNM1, *Staphylococcus* virus phiNM2, *Staphylococcus* virus phiNM4, *Staphylococcus* virus SAP26, *Staphylococcus* virus X2, *Enterococcus* virus FL1, *Enterococcus* virus FL2, *Enterococcus* virus FL3, *Lactobacillus* virus ATCC8014, *Lactobacillus* virus phiJL1, *Pediococcus* virus cIP1, *Aeromonas* virus pIS4A, *Listeria* virus LP302, *Listeria* virus PSA, *Methanobacterium* virus psiM1, *Roseobacter* virus RDJL1, *Roseobacter* virus RDJL2, *Rhodococcus* virus RER2, *Enterococcus* virus BC611, *Enterococcus* virus IMEEF1, *Enterococcus* virus SAP6, *Enterococcus* virus VD13, *Streptococcus* virus SPQS1, *Mycobacterium* virus Papyrus, *Mycobacterium* virus Send513, *Burkholderia* virus KL1, *Pseudomonas* virus 73, *Pseudomonas* virus Ab26, *Pseudomonas* virus Kakheti25, *Escherichia* virus Cajan, *Escherichia* virus Seurat, *Staphylococcus* virus SEP9, *Staphylococcus* virus Sextaec, *Streptococcus* virus 858, *Streptococcus* virus 2972, *Streptococcus* virus ALQ132, *Streptococcus* virus 01205, *Streptococcus* virus Sfi11, *Streptococcus* virus 7201, *Streptococcus* virus DT1, *Streptococcus* virus phiAbc2, *Streptococcus* virus Sfi19, *Streptococcus* virus Sfi21, *Paenibacillus* virus Diva, *Paenibacillus* virus Hb10c2, *Paenibacillus* virus Rani, *Paenibacillus* virus Shelly, *Paenibacillus* virus Sitara, *Paenibacillus* virus Willow, *Lactococcus* virus 712, *Lactococcus* virus ASCC191, *Lactococcus* virus ASCC273, *Lactococcus* virus ASCC281, *Lactococcus* virus ASCC465, *Lactococcus* virus ASCC532, *Lactococcus* virus Bibb29, *Lactococcus* virus bIL170, *Lactococcus* virus CB13, *Lactococcus* virus CB14, *Lactococcus* virus CB19, *Lactococcus* virus CB20, *Lactococcus* virus jj50, *Lactococcus* virus P2, *Lactococcus* virus P008, *Lactococcus* virus ski, *Lactococcus* virus SI4, *Bacillus* virus Slash, *Bacillus* virus Stahl, *Bacillus* virus Staley, *Bacillus* virus Stills, *Gordonia* virus Bachita, *Gordonia* virus ClubL, *Gordonia* virus OneUp, *Gordonia* virus Smoothie, *Gordonia* virus Soups, *Bacillus* virus SPbeta, *Vibrio* virus MAR10, *Vibrio* virus SSP002, *Escherichia* virus AKFV33, *Escherichia* virus BF23, *Escherichia* virus DT57C, *Escherichia* virus EPS7, *Escherichia* virus FFH1, *Escherichia* virus H8, *Escherichia* virus slur09, *Escherichia* virus T5, *Salmonella* virus 118970sal2, *Salmonella* virus Shivani, *Salmonella* virus SPC35, *Salmonella* virus Stitch, *Arthrobacter* virus Tank, *Tsukamurella* virus TIN2, *Tsukamurella* virus TIN3, *Tsukamurella* virus TIN4, *Rhodobacter* virus RcSpartan, *Rhodobacter* virus RcTitan, *Mycobacterium* virus Anaya, *Mycobacterium* virus Angelica, *Mycobacterium* virus Crimd, *Mycobacterium* virus Fionnbarth, *Mycobacterium* virus Jaws, *Mycobacterium* virus Larva, *Mycobacterium* virus Macncheese, *Mycobacterium* virus Pixie, *Mycobacterium* virus TM4, *Bacillus* virus BMBtp2, *Bacillus* virus TP21, *Geobacillus* virus Tp84, *Staphylococcus* virus 47, *Staphylococcus* virus 3a, *Staphylococcus* virus 42e, *Staphylococcus* virus IPLA35, *Staphylococcus* virus phi12, *Staphylococcus* virus phiSLT, *Mycobacterium* virus 32HC, *Rhodococcus* virus RGL3, *Paenibacillus* virus Vegas, *Gordonia* virus Vendetta, *Bacillus* virus Wbeta, *Mycobacterium* virus Wildcat, *Gordonia* virus Twister6, *Gordonia* virus Wizard, *Gordonia* virus Hotorobo, *Gordonia* virus Monty, *Gordonia* virus Woes, *Xanthomonas* virus CP1, *Xanthomonas* virus OP1, *Xanthomonas* virus phil7, *Xanthomonas* virus Xop411, *Xanthomonas* virus Xp10, *Streptomyces* virus TP1604, *Streptomyces* virus YDN12, *Alphaproteobacteria* virus phiJI001, *Pseudomonas* virus LKO4, *Pseudomonas* virus M6, *Pseudomonas* virus MP1412, *Pseudomonas* virus PAE1, *Pseudomonas* virus Yua, *Pseudoalteromonas* virus PM2, *Pseudomonas* virus phi6, *Pseudomonas* virus phi8, *Pseudomonas* virus phi12, *Pseudomonas* virus phi13, *Pseudomonas* virus phi2954, *Pseudomonas* virus phiNN, *Pseudomonas* virus phiYY, *Vibrio* virus fs1, *Vibrio* virus VGJ, *Ralstonia* virus RS603, *Ralstonia* virus RSM1, *Ralstonia* virus RSM3, *Escherichia* virus M13, *Escherichia* virus 122, *Salmonella* virus IKe, *Acholeplasma* virus L51, *Vibrio* virus fs2, *Vibrio* virus VFJ, *Escherichia* virus If1, *Propionibacterium* virus B5, *Pseudomonas* virus Pf1, *Pseudomonas* virus Pf3, *Ralstonia* virus PE226, *Ralstonia* virus RSS1, *Spiroplasma* virus SVTS2, *Stenotrophomonas* virus PSH1, *Stenotrophomonas* virus SMA6, *Stenotrophomonas* virus SMA7, *Stenotrophomonas* virus SMA9, *Vibrio* virus CTXphi, *Vibrio* virus KSF1, *Vibrio* virus VCY, *Vibrio* virus Vf33, *Vibrio* virus VfO3K6, *Xanthomonas* virus Cf1c, *Spiroplasma* virus C74, *Spiroplasma* virus R8A2B, *Spiroplasma* virus SkV1CR23x, *Escherichia* virus FI, *Escherichia* virus Qbeta, *Escherichia* virus BZ13, *Escherichia* virus MS2, *Escherichia* virus alpha3, *Escherichia* virus 1D21, *Escherichia* virus 1D32, *Escherichia* virus 1D62, *Escherichia* virus NC28, *Escherichia* virus NC29, *Escherichia* virus NC35, *Escherichia* virus phiK, *Escherichia* virus St1, *Escherichia* virus WA45, *Escherichia* virus G4, *Escherichia* virus 1D52, *Escherichia* virus Talmos, *Escherichia* virus phiX174, *Bdellovibrio* virus MAC1, *Bdellovibrio* virus MH2K, *Chlamydia* virus Chp1, *Chlamydia* virus Chp2, *Chlamydia* virus CPAR39, *Chlamydia* virus CPG1, *Spiroplasma* virus SpV4, *Acholeplasma* virus L2, *Pseudomonas* virus PR4, *Pseudomonas* virus PRD1, *Bacillus* virus AP50, *Bacillus* virus Bam35, *Bacillus* virus GIL16, *Bacillus* virus Wip1, *Escherichia* virus phi80, *Escherichia* virus RB42, *Escherichia* virus T2, *Escherichia* virus T3, *Escherichia* virus T6, *Escherichia* virus VT2-Sa, *Escherichia* virus VT1-Sakai, *Escherichia* virus VT2-Sakai, *Escherichia* virus CP-933V, *Escherichia* virus P27, *Escherichia* virus Stx2phi-1, *Escherichia* virus Stx1phi, *Escherichia* virus Stx2phi-11, *Escherichia* virus CP-1639, based on the *Escherichia* virus BP-4795, *Escherichia* virus 86, *Escherichia* virus Min27, *Escherichia* virus 2851, *Escherichia* virus 1717, *Escherichia* virus YYZ-2008, *Escherichia* virus ECO26_P06, *Escherichia* virus ECO103_P15, *Escherichia* virus ECO103_P12, *Escherichia* virus ECO111_P16, *Escherichia* virus ECO111_P11, *Escherichia* virus VT2phi_272, *Escherichia* virus TL-2011c, *Escherichia* virus P13374, *Escherichia* virus Spy.

In one embodiment, the bacterial virus particles target *E. coli* and includes the capsid of a bacteriophage selected in the group consisting of BW73, B278, D6, D108, E, EI, E24, E41, FI-2, FI-4, FI-5, H18A, Ff18B, i, MM, Mu, 025, PhI-5, Pk, PSP3, PI, PID, P2, P4, SI, Wφ, φK13, φI, φ2, φ7, φ92, 7 A, 8φ, 9φ, 18, 28-1, 186, 299, HH-*Escherichia* (2), AB48, CM, C4, C16, DD-VI, E4, E7, E28, FII, F13, H, HI, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, Sal-I, Sal-2, Sal-3, Sal-4, Sal-5, Sal-6, TC23, TC45, TuII*-6, TuIP-24, TuII*46, TuIP-60, T2, T4, T6, T35, al, 1, IA, 3, 3A, 3T+, 5φ, 9266Q, CFO103, HK620, J, K, KIF, m59, no. A, no. E, no. 3, no. 9, N4, sd, T3, T7, WPK, W31, ΔH, φC3888, φK3, φK7, φK12, φV-1, φ04-CF, φ05, φ06, φ07, φI, φI.2, φ20, φ95, φ263, φIO92, φI, φII, Ω8, 1, 3, 7, 8, 26, 27, 28-2, 29, 30, 31, 32, 38, 39, 42, 933W, NN-*Escherichia* (1), Esc-7-11, AC30, CVX-5, CI, DDUP, ECI, EC2, E21, E29, FI, F26S, F27S, Hi, HK022, HK97, HK139, HK253, HK256, K7, ND-1, PA-2, q, S2, TI, T3C, T5, UC-I, w, β4, γ2, λ, φD326, φγ, φ06, φ7, φ10, φ80, χ, 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J and 933H.

In some embodiment the vectors disclosed herein may be used in combination with prebiotics. Prebiotics include, but are not limited to, amino acids, biotin, fructo-oligosaccharide, galacto-oligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carrageenan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

In other embodiment, the vectors disclosed herein may be used in combination with probiotics. Probiotics include, but are not limited to lactobacilli, bifidobacteria, streptococci, enterococci, propionibacteria, saccaromycetes, lactobacilli, bifidobacteria, or proteobacteria.

Screening Methods

The invention encompasses methods for screening for genetic modifications in bacteria. In one embodiment, the method comprises administering a vector designed to genetically modify at least one base of a DNA of interest in a gene of a naturally occurring bacteria, to a subject, subsequently collecting a bacterial sample from the subject, quantitating the level of bacteria containing a genetic modification in said at least one base of a DNA of interest in said bacterial sample. The method can further comprise quantitating the level of bacteria not containing a genetic modification in said at least one base of a DNA of interest.

In one embodiment, the proportion of endogenous modified vs non-modified bacteria is quantified. Preferred percentages of bacteria with the genetic modification are at least 20%, 30%, 40%, 50%, 60%, 70%, 80%, 90%, 95%, 97%, 98%, 99%, 99.9%, 99.99%, and 100%.

In one embodiment, the number of non-modified endogenous bacteria is quantified prior to administering a vector. The patient can also be pre-screened to determine the genetic signature of the strains the patient carries. This will allow selection of an appropriate capsid to deliver the therapeutic payload based on the genetic signature of the strains the patient carry.

In preferred embodiments, the vector is in a pharmaceutical and veterinary composition. Preferably the vector is a bacteriophage.

The vector can be administered to the subject by any administration technique known in the art, depending on the vector and the target bacteria's expected location in or on the subject.

The bacterial sample can be collected by any means known in the art, such as biopsy, blood draw, urine sample, stool sample, or oral/nasal swab, etc.

The level of bacteria containing or not containing a genetic modification in a base of a DNA of interest can be determined by any technique known to the skilled artisan, such as routine diagnostic procedures including ELISA, PCR, High Resolution Melting, and nucleic acid sequencing.

The invention encompasses methods for determining the efficiency of a vector at inducing genetic mutations in situ. In one embodiment, the method comprises administering a vector designed to genetically modify at least one base of a DNA of interest in a gene of a naturally occurring bacteria, to a subject, subsequently collecting a bacterial sample from the subject, quantitating the level of bacteria containing a genetic modification in said at least one base of a DNA of interest and quantitating the level of bacteria not containing a genetic modification in said at least one base of a DNA of interest in said bacterial sample.

In preferred embodiments, the vector is in a pharmaceutical and veterinary composition. Preferably the vector is a bacteriophage.

The vector can be administered to the subject by any administration technique known in the art, depending on the vector and the target bacteria's expected location in or on the subject.

The bacterial sample can be collected by any means known in the art, such as biopsy, blood draw, urine sample, stool sample, or oral/nasal swab, etc.

The level of bacteria containing or not containing a genetic modification in a base of a DNA of interest can be determined by any technique known to the skilled artisan, such as routine diagnostic procedures including ELISA, PCR, High Resolution Melting, and nucleic acid sequencing.

The invention encompasses methods for determining the effect of a genetic mutation on bacterial growth. In one embodiment, the method comprises administering a vector designed to genetically modify at least one base of a DNA of interest in a gene of a naturally occurring bacteria, to a subject, subsequently collecting at least two sequential bacterial samples from the subject, quantitating the level of bacteria containing a genetic modification in said at least one base of a DNA of interest and quantitating the level of bacteria not containing a genetic modification in said at least one base of a DNA of interest in said bacterial samples.

In preferred embodiments, the vector is in a pharmaceutical and veterinary composition. Preferably the vector is a bacteriophage.

The vector can be administered to the subject by any administration technique known in the art, depending on the vector and the target bacteria's expected location in or on the subject.

The bacterial samples can be collected by any means known in the art, such as biopsy, blood draw, urine sample, stool sample, or oral/nasal swab, etc. The samples can be collected at any sequential time points. Preferably, the time between these collections is at least 3, 6, 12, 24, 48, 72, 96 hrs or 7, 14, 30, 60, 120, or 365 days.

The level of bacteria containing or not containing a genetic modification in a base of a DNA of interest can be determined by any technique known to the skilled artisan, such as routine diagnostic procedures including ELISA, PCR, High Resolution Melting, and nucleic acid sequencing.

All of the screening methods of the invention can use any of the vectors and enzymes/systems of the invention to screen for any of the genetic modification of the invention.

All of the screening methods of the invention can further include a step of comparing the level of bacteria containing a genetic modification in a base of a DNA of interest with the level of bacteria not containing a genetic modification the base of a DNA of interest in a bacterial sample.

All of the screening methods of the invention can further include a step of contacting the vector with bacteria in liquid or solid culture and quantifying the level of bacteria containing a genetic modification in said at least one base of a DNA of interest in said bacterial sample. The method can further comprise quantitating the level of bacteria not containing a genetic modification in said at least one base of a DNA of interest.

In one embodiment, the method comprises providing a vector designed to genetically modify at least one base of a DNA of interest in a gene of a naturally occurring bacteria. The method can further comprise contacting the vector with bacteria in liquid or solid culture and quantitating the level of bacteria containing a genetic modification in said at least one base of a DNA of interest in said bacterial sample. The method can further comprise quantitating the level of bacteria not containing a genetic modification in said at least one base of a DNA of interest. The levels of bacteria containing a genetic modification in a base of a DNA of interest can be compared with the level of bacteria not containing a genetic modification the base of a DNA of interest over time in the culture. Preferably, the time between these comparisons is at least 1, 2, 3, 4, 5, 6, 12, 24, 48, 72, or 96 hours.

Pharmaceutical and Veterinary Compositions and In Situ Administration Methods

The invention encompasses pharmaceutical and veterinary compositions comprising the vectors of the invention.

The invention encompasses in situ administration of the pharmaceutical or veterinary composition to the bacteria in a subject. Any method known to the skilled artisan can be used to contact the vector with the bacterial target in situ.

The pharmaceutical or veterinary composition according to the invention may further comprise a pharmaceutically acceptable vehicle. A solid pharmaceutically acceptable vehicle may include one or more substances which may also act as flavoring agents, lubricants, solubilisers, suspending agents, dyes, fillers, glidants, compression aids, inert binders, sweeteners, preservatives, dyes, coatings, or tablet-disintegrating agents. Suitable solid vehicles include, for example calcium phosphate, magnesium stearate, talc, sugars, lactose, dextrin, starch, gelatin, cellulose, polyvinylpyrrolidone, low melting waxes and ion exchange resins.

The pharmaceutical or veterinary composition may be prepared as a sterile solid composition that may be suspended at the time of administration using sterile water, saline, or other appropriate sterile injectable medium. The pharmaceutical or veterinary compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The particles according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for enteral administration include sterile solutions, emulsions, and suspensions.

The bacterial virus particles according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and enteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for enteral administration. The liquid vehicle for pressurized compositions can be a halogenated hydrocarbon or other pharmaceutically acceptable propellant.

In some embodiments, the invention encompasses pharmaceutical or veterinary composition formulated for delayed or gradual enteric release. In preferred embodiments, formulations or pharmaceutical preparations of the invention are formulated for delivery of the vector into the distal small bowel and/or the colon. The formulation can allow the vector to pass through stomach acid and pancreatic enzymes and bile, and reach undamaged to be viable in the distal small bowel and colon.

In some embodiments, the pharmaceutical or veterinary composition is micro-encapsulated, formed into tablets and/or placed into capsules, preferably enteric-coated capsules.

In some embodiments, the pharmaceutical or veterinary compositions are formulated for delayed or gradual enteric release, using cellulose acetate (CA) and polyethylene glycol (PEG). In some embodiments, the pharmaceutical or veterinary compositions are formulated for delayed or gradual enteric release using a hydroxypropylmethylcellulose (HPMC), a microcrystalline cellulose (MCC) and magnesium stearate. the pharmaceutical or veterinary compositions are formulated for delayed or gradual enteric release using e.g., a poly(meth)acrylate, e.g. a methacrylic acid copolymer B, a methyl methacrylate and/or a methacrylic acid ester, or a polyvinylpyrrolidone (PVP).

In some embodiments, the pharmaceutical or veterinary compositions are formulated for delayed or gradual enteric release using a release-retarding matrix material such as: an acrylic polymer, a cellulose, a wax, a fatty acid, shellac, zein, hydrogenated vegetable oil, hydrogenated castor oil, polyvinylpyrrolidone, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropylmethylcellulose, a hydroxymethyl cellulose, a hydroxyethyl cellulose, a hydroxypropyl cellulose, a cross-linked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a copolymer of lactic and glycolic acid, carboxymethyl starch, potassium methacrylate/divinylbenzene copolymer, crosslinked polyvinylpyrrolidone, polyvinylalcohols, polyvinylalcohol copolymers, polyethylene glycols, non-crosslinked polyvinylpyrrolidone, polyvinyl acetates, polyvinylacetate copolymers or any combination thereof.

In some embodiments, the pharmaceutical or veterinary compositions are formulated for delayed or gradual enteric release as described in U.S. Pat. App. Pub. 20110218216, which describes an extended release pharmaceutical composition for oral administration, and uses a hydrophilic polymer, a hydrophobic material and a hydrophobic polymer or a mixture thereof, with a microenvironment pH modifier. The hydrophobic polymer can be ethylcellulose, cellulose acetate, cellulose propionate, cellulose butyrate, methacrylic acid-acrylic acid copolymers or a mixture thereof. The hydrophilic polymer can be polyvinylpyrrolidone, hydroxypropylcellulose, methylcellulose, hydroxypropylmethyl cellulose, polyethylene oxide, acrylic acid copolymers or a mixture thereof. The hydrophobic material can be a hydrogenated vegetable oil, hydrogenated castor oil, carnauba wax, candellia wax, beeswax, paraffin wax, stearic acid, glyceryl behenate, cetyl alcohol, cetostearyl alcohol or and a mixture thereof. The microenvironment pH modifier can be an inorganic acid, an amino acid, an organic acid or a mixture thereof. Alternatively, the microenvironment pH modifier can be lauric acid, myristic acid, acetic acid, benzoic acid, palmitic acid, stearic acid, oxalic acid, malonic acid, succinic acid, adipic acid, sebacic acid, fumaric acid, maleic acid; glycolic acid, lactic acid, malic acid, tartaric acid, citric acid, sodium dihydrogen citrate, gluconic acid, a salicylic acid, tosylic acid, mesylic acid or malic acid or a mixture thereof.

In some embodiments, the pharmaceutical or veterinary compositions are a powder that can be included into a tablet or a suppository. In alternative embodiments, a formulation or pharmaceutical preparation of the invention can be a 'powder for reconstitution' as a liquid to be drunk or otherwise administered.

In some embodiments, the pharmaceutical or veterinary compositions can be administered in a cream, gel, lotion, liquid, feed, or aerosol spray. In some embodiments, a bacteriophage is immobilized to a solid surface using any substance known in the art and any technology known in the art, for example, but not limited to immobilization of bacteriophages onto polymeric beads using technology as outlined in U.S. Pat. No. 7,482,115, which is incorporated herein by reference. Phages may be immobilized onto appropriately sized polymeric beads so that the coated beads may be added to aerosols, creams, gels or liquids. The size of the polymeric beads may be from about 0.1 µm to 500 µm, for example 50 µm to 100 µm. The coated polymeric beads may be incorporated into animal feed, including pelleted feed and feed in any other format, incorporated into any other edible device used to present phage to the animals, added to water offered to animals in a bowl, presented to animals through water feeding systems. In some embodiments, the compositions are used for treatment of surface wounds and other surface infections using creams, gels, aerosol sprays and the like.

In some embodiments, the pharmaceutical or veterinary compositions can be administered by inhalation, in the form of a suppository or pessary, topically (e.g., in the form of a lotion, solution, cream, ointment or dusting powder), epi- or transdermally (e.g., by use of a skin patch), orally (e.g., as a tablet, which may contain excipients such as starch or lactose), as a capsule, ovule, elixirs, solutions, or suspensions (each optionally containing flavoring, coloring agents and/or excipients), or they can be injected parenterally (e.g., intravenously, intramuscularly or subcutaneously). For parenteral administration, the compositions may be used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner. In a preferred embodiment, a bacteriophage and/or polypeptide of the present invention is administered topically, either as a single agent, or in combination with other antibiotic treatments, as described herein or known in the art.

In some embodiments, the pharmaceutical or veterinary compositions can also be dermally or transdermally administered. For topical application to the skin, the pharmaceutical or veterinary composition can be combined with one or a combination of carriers, which can include but are not limited to, an aqueous liquid, an alcohol base liquid, a water soluble gel, a lotion, an ointment, a nonaqueous liquid base, a mineral oil base, a blend of mineral oil and petrolatum, lanolin, liposomes, proteins carriers such as serum albumin or gelatin, powdered cellulose carmel, and combinations thereof. A topical mode of delivery may include a smear, a spray, a bandage, a time-release patch, a liquid-absorbed wipe, and combinations thereof. The pharmaceutical or veterinary composition can be applied to a patch, wipe, bandage, etc., either directly or in a carrier(s). The patches, wipes, bandages, etc., may be damp or dry, wherein the phage and/or polypeptide (e.g., a lysin) is in a lyophilized form on the patch. The carriers of topical compositions may comprise semi-solid and gel-like vehicles that include a polymer thickener, water, preservatives, active surfactants, or emulsifiers, antioxidants, sun screens, and a solvent or mixed solvent system. U.S. Pat. No. 5,863,560 discloses a number of different carrier combinations that can aid in the exposure of skin to a medicament, and its contents are incorporated herein.

For intranasal or administration by inhalation, the pharmaceutical or veterinary composition is conveniently delivered in the form of a dry powder inhaler or an aerosol spray presentation from a pressurized container, pump, spray, or nebuliser with the use of a suitable propellant, e.g., dichlorodifluoromethane, trichlorofluoromethane, dichlorotetrafluoroethane, a hydrofluoroalkane such as 1,1,1,2-tetrafluoroethane or 1,1,1,2,3,3,3-heptafluoropropane, carbon dioxide, or other suitable gas. In the case of a pressurized aerosol, the dosage unit may be determined by providing a valve to deliver a metered amount. The pressurized container, pump, spray, or nebuliser may contain a solution or suspension of the active compound, e.g., using a mixture of ethanol and the propellant as the solvent, which may additionally contain a lubricant, e.g., sorbitan trioleate. Capsules and cartridges (made, for example, from gelatin) for use in an inhaler or insufflator may be formulated to contain a powder mix of the bacteriophage and/or polypeptide of the invention and a suitable powder base such as lactose or starch.

For administration in the form of a suppository or pessary, the pharmaceutical or veterinary composition can be applied topically in the form of a gel, hydrogel, lotion, solution, cream, ointment, or dusting powder. Compositions of the invention may also be administered by the ocular route. For ophthalmic use, the compositions of the invention can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

Dosages and desired drug concentrations of the pharmaceutical and veterinary composition compositions of the present invention may vary depending on the particular use. The determination of the appropriate dosage or route of administration is within the skill of an ordinary physician. Animal experiments can provide reliable guidance for the determination of effective doses in human therapy.

For transdermal administration, the pharmaceutical or veterinary composition can be formulated into ointment, cream or gel form and appropriate penetrants or detergents could be used to facilitate permeation, such as dimethyl sulfoxide, dimethylacetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Disease Treatment

The invention encompasses the treatment of diseases and metabolic disorders caused by bacteria. The diseases or disorders caused by bacteria may be selected from the group consisting of skin chronic inflammation such as acne (acne vulgaris), progressive macular hypomelanosis, abdominal cramps, acute epiglottitis, arthritis, bacteraemia, bloody diarrhea, botulism, Brucellosis, brain abscess, cardiomyopathy, chancroid venereal disease, Chlamydia, Crohn's disease, conjunctivitis, cholecystitis, colorectal cancer, polyposis, dysbiosis, Lyme disease, diarrhea, diphtheria, duodenal ulcers, endocarditis, erysipelothricosis, enteric fever, fever, glomerulonephritis, gastroenteritis, gastric ulcers, Guillain-Barre syndrome tetanus, gonorrhoea, gingivitis, inflammatory bowel diseases, irritable bowel syndrome, leptospirosis, leprosy, listeriosis, tuberculosis, Lady Widermere syndrome, Legionaire's disease, meningitis, mucopurulent conjunctivitis, multi-drug resistant bacterial infections, multi-drug resistant bacterial carriage, myocarditis, myonecrosis-gas gangrene, *Mycobacterium avium* complex, neonatal necrotizing enterocolitis, nocardiosis, nosocomial infection, otitis, periodontitis, phalyngitis, pneumonia, peritonitis, purpuric fever, Rocky Mountain spotted fever, shigellosis, syphilis, sinusitis, sigmoiditis, septicaemia, subcutaneous abscesses, tularaemia, tracheobronchitis, tonsillitis, typhoid fever, ulcerative colitis, urinary infection, whooping cough, Non-alcoholic Fatty Liver Disease (NAFLD), Nonalcoholic steatohepatitis (NASH).

The infection caused by bacteria may be selected from the group consisting of infections, preferably intestinal infections such as esophagitis, gastritis, enteritis, colitis, sigmoiditis, rectitis, and peritonitis, urinary tract infections, vaginal infections, female upper genital tract infections such as salpingitis, endometritis, oophoritis, myometritis, parametritis and infection in the pelvic peritoneum, respiratory tract infections such as pneumonia, intra-amniotic infections, odontogenic infections, endodontic infections, fibrosis, meningitis, bloodstream infections, nosocomial infection such as catheter-related infections, hospital acquired pneumonia, post-partum infection, hospital acquired gastroenteritis, hospital acquired urinary tract infections, or a combination thereof. Preferably, the infection according to the invention is caused by a bacterium presenting an antibiotic resistance. In a particular embodiment, the infection is caused by a bacterium as listed above in the targeted bacteria.

The disclosure also concerns a pharmaceutical or veterinary composition of the invention for the treatment of a metabolic disorder including, for example, obesity, type 2 diabetes and nonalcoholic fatty liver disease. Indeed, emerging evidence indicates that these disorders are characterized by alterations in the intestinal microbiota composition and its metabolites (Tilg et al., Nature Reviews Immunology, volume 20, pages 40-54, 2020). The pharmaceutical or veterinary composition may thus be used to deliver in some intestinal bacteria a nucleic acid of interest which can alter the intestinal microbiota composition or its metabolites (e.g. by inducing expression, overexpression or secretion of some molecules by said bacteria, for example molecules having a beneficial role on metabolic inflammation). The disclosure also concerns the use of a pharmaceutical or veterinary composition of the invention for the manufacture of a medicament for the treatment of a metabolic disorder including, for example, obesity, type 2 diabetes and nonalcoholic fatty liver disease. It also relates to a method for treating a metabolic disorder including, for example, obesity, type 2 diabetes and nonalcoholic fatty liver disease, comprising administering to a subject having a metabolic disorder in need of treatment the provided pharmaceutical or veterinary composition, in particular a therapeutically effective amount of the provided pharmaceutical or veterinary composition.

In a particular embodiment, the invention concerns a pharmaceutical or veterinary composition for use in the treatment of pathologies involving bacteria of the human microbiome, such as inflammatory and auto-immune diseases, cancers, infections or brain disorders. Indeed, some bacteria of the microbiome, without triggering any infection, can secrete molecules that will induce and/or enhance inflammatory or auto-immune diseases or cancer development. More specifically, the present invention relates also to modulating microbiome composition to improve the efficacy of immunotherapies based, for example, on CAR-T (Chimeric Antigen Receptor T) cells, TIL (Tumor Infiltrating Lymphocytes) and Tregs (Regulatory T cells) also known as suppressor T cells. Modulation of the microbiome composition to improve the efficacy of immunotherapies may also include the use of immune checkpoint inhibitors well known in the art such as, without limitation, PD-1 (programmed cell death protein 1) inhibitor, PD-L1 (programmed death ligand 1) inhibitor and CTLA-4 (cytotoxic T lymphocyte associated protein 4).

Some bacteria of the microbiome can also secrete molecules that will affect the brain.

Therefore, a further object of the invention is a method, in particular a non-therapeutic method, for controlling the microbiome of a subject, comprising administering an effective amount of the pharmaceutical composition as disclosed herein in said subject. A further object of the invention is the pharmaceutical composition of the invention further use for controlling the microbiome of a subject.

In a particular embodiment, the invention also relates to a method for personalized treatment for an individual in need of treatment for a bacterial infection comprising: i) obtaining a biological sample from the individual and determining a group of bacterial DNA sequences from the sample; ii) based on the determining of the sequences, identifying one or more pathogenic bacterial strains or species that were in the sample; and iii) administering to the individual a pharmaceutical composition according to the invention capable of recognizing each pathogenic bacterial strain or species identified in the sample and to deliver the packaged payload. The present invention also concerns a pharmaceutical composition of the invention for use in a method for personalized treatment for an individual in need of treatment for a bacterial infection, said method comprising: i) obtaining a biological sample from the individual and determining a group of bacterial DNA sequences from the sample; ii) based on the determining of the sequences, identifying one or more pathogenic bacterial strains or species that were in the sample; and wherein the pharmaceutical composition is capable of recognizing each pathogenic bacterial strain or species identified in the sample and to deliver the packaged plasmid.

Preferably, the biological sample comprises pathological and non-pathological bacterial species, and subsequent to administering the pharmaceutical or veterinary composition according to the invention to the individual, the amount of pathogenic bacteria on or in the individual are reduced, but the amount of non-pathogenic bacteria is not reduced.

In another particular embodiment, the invention concerns a pharmaceutical or veterinary composition according to the invention for use in order to improve the effectiveness of drugs. Indeed, some bacteria of the microbiome, without being pathogenic by themselves, are known to be able to metabolize drugs and to modify them in ineffective or harmful molecules.

In another particular embodiment, the invention concerns the in-situ bacterial production of any compound of interest, including therapeutic compound such as prophylactic and therapeutic vaccine for mammals. The compound of interest can be produced inside the targeted bacteria, secreted from the targeted bacteria or expressed on the surface of the targeted bacteria. In a more particular embodiment, an antigen is expressed on the surface of the targeted bacteria for prophylactic and/or therapeutic vaccination.

Method for Counter-Selection In Situ

In a particular embodiment, the vector encodes a DNA modifying enzyme, in particular a programmed nuclease, that can discriminate between targeted bacteria that have been genetically modified in situ and targeted bacteria in which the modification has not occurred, leading to the specific killing of the targeted bacteria in which the modification has not occurred.

In a particular embodiment, the nuclease can be a RNA-guided nuclease.

In a particular embodiment, the design of the vector increases the chances that the killing effect mediated by said programmed nuclease is delayed, thereby providing enough time for the target DNA sequence to be edited by the base-editing or prime-editing enzyme/system.

The invention also provides compositions and methods to ensure a robust alteration of all targeted bacteria within a microbiome population, thanks to the delivery of a nuclease programmed to discriminate between targeted bacteria that have been genetically modified in situ and targeted bacteria in which the modification has not occurred, leading to the specific killing of those in which the modification has not occurred. In a particular embodiment, the vector of the invention is thus used in combination with a nucleic acid encoding a nuclease programmed to discriminate between targeted bacteria that have been genetically modified in situ and targeted bacteria in which the modification has not occurred, leading to the specific killing of those in which the modification has not occurred. In a particular embodiment, the delivery of such a programmed nuclease is either on the same vector as the one carrying the base-editing nuclease, or on a different vector. In a particular embodiment, the delivery of such programmed nuclease is implemented either simultaneously or after the vector encoding the base-editing nuclease. If delivered simultaneously, the vector can be engineered to have a delayed targeting process for the programmed nuclease leading to a double strand break.

Non-Therapeutic Uses

The present invention also relates to a non-therapeutic use of the bacterial delivery particles of the invention. For instance, the non-therapeutic use can be a cosmetic use or a use for improving the well-being of a subject, in particular a subject who does not suffer from a disease. Accordingly, the present invention also relates to a cosmetic composition or a non-therapeutic composition comprising the bacterial delivery particles of the invention.

Subject, Regimen and Administration

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, or non-mammals such as poultry, that are in need of treatment.

The human subject according to the invention may be a human at the prenatal stage, a new-born, a child, an infant, an adolescent or an adult at any age.

In a preferred embodiment, the subject has been diagnosed with, or is at risk of developing an infection, a disorder and/or a disease preferably due to a bacterium. Diagnostic methods of such infection, disorder and/or disease are well known by the man skilled in the art.

In a particular embodiment, the infection, disorder and/or disease presents a resistance to treatment, preferably the infection, disorder or disease presents an antibiotic resistance.

In a particular embodiment, the subject has never received any treatment prior to the administration of the delivery vehicles according to the invention, preferably a vector according to the invention, particularly a payload packaged into a delivery vehicle according to the invention, preferably a packaged plasmid or phagemid into a bacterial virus particle according to the invention, or of a pharmaceutical or veterinary composition according to the invention.

In a particular embodiment, the subject has already received at least one line of treatment, preferably several lines of treatment, prior to the administration of the delivery vehicles according to the invention, preferably a vector according to the invention, particularly a payload packaged into a delivery vehicle according to the invention, preferably a packaged plasmid or phagemid into a bacterial virus particle according to the invention, or of a pharmaceutical or veterinary composition according to the invention.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with delivery vehicles according to the invention, preferably a vector according to the invention, particularly a payload packaged into a delivery vehicle according to the invention, preferably a packaged plasmid or phagemid into a bacterial virus particle according to the invention, or with a pharmaceutical or veterinary composition according to the invention, is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is about 1 week. Alternatively, the treatment may last as long as the infection, disorder and/or disease persists.

The form of the pharmaceutical or veterinary compositions, the route of administration and the dose of administration of delivery vehicles according to the invention, preferably of a vector according to the invention, particularly of a payload packaged into a delivery vehicle according to the invention, preferably of a packaged plasmid or phagemid into a bacterial virus particle according to the invention, or of a pharmaceutical or veterinary composition according to the invention can be adjusted by the man skilled in the art according to the type and severity of the infection (e.g. depending on the bacteria species involved in the disease, disorder and/or infection and its localization in the patient's or subject's body), and to the patient or subject, in particular its age, weight, sex, and general physical condition.

Particularly, the amount of delivery vehicles according to the invention, preferably a vector according to the invention, particularly a payload packaged into a delivery vehicle according to the invention, preferably a packaged plasmid or phagemid into a bacterial virus particle according to the invention, or of a pharmaceutical or veterinary composition according to the invention, to be administered has to be determined by standard procedure well known by those of ordinary skills in the art. Physiological data of the patient or subject (e.g. age, size, and weight) and the routes of administration have to be taken into account to determine the appropriate dosage, so as a therapeutically effective amount will be administered to the patient or subject.

For example, the total amount of delivery vehicles, particularly a payload packaged into a delivery vehicle according to the invention, preferably a plasmid or phagemid packaged into a bacterial virus particle according to the invention, for each administration is comprised between $10^4$ and $10^{15}$ delivery vehicles.

The present invention further concerns the following embodiments:

1. A method of modifying a naturally occurring bacteria in situ comprising:
   genetically modifying a DNA sequence in the naturally occurring bacteria in situ without introducing a double strand break in the DNA sequence,
   wherein said genetic modification does not lead to the death of bacteria.
2. The method according to embodiment 1, comprising contacting said naturally occurring bacteria with a vector.
3. The method according to embodiment 1, comprising contacting said naturally occurring bacteria with a vector located inside a delivery vehicle.
4. The method according to embodiment 3, wherein said vector located inside a delivery vehicle is a phagemid.
5. The method according to embodiment 1, comprising transducing said naturally occurring bacteria with a packaged phagemid.
6. The method according to embodiment 4 or 5, wherein said phagemid comprises a nucleic acid sequence encoding a dCas9 (dead-Cas9) or nCas9 (nickase Cas9).
7. The method according to embodiment 4 or 5, wherein said phagemid comprises a nucleic acid sequence encoding a dCas9 and a deaminase domain, or a nCas9 and deaminase domain.
8. The method according to embodiment 4 or 5, wherein said phagemid comprises a nucleic acid sequence encoding a dCas9 and a reverse transcriptase domain, or a nCas9 and a reverse transcriptase domain.
9. The method according to any of embodiments 2 to 8, wherein the vector or phagemid further comprises a conditional origin of replication which is inactive in the targeted naturally occurring bacteria but is active in a donor bacterial cell.
10. The method according to embodiment 9, wherein said conditional origin of replication is an origin of replication, the replication of which depends upon the presence of a given protein, peptid, nucleic acid, RNA, molecule or any combination thereof.
11. The method according to embodiment 10, wherein said conditional origin of replication is active in said donor bacterial cell because said donor bacterial cell expresses said given protein, peptid, nucleic acid, RNA, molecule or any combination thereof.
12. The method according to any of embodiments 9-11, wherein said conditional origin of replication is an origin of replication derived from phage-inducible chromosomal islands (PICIs).
13. The method according to embodiment 12, wherein said conditional origin of replication is active in said donor bacterial cell because said donor bacterial cell expresses a rep protein, in particular a primase-helicase.
14. The method according to embodiment 12 or 13, wherein said conditional origin of replication is derived from the origin of replication from the PICI of the *Escherichia coli* strain CFT073.
15. The method according to embodiment 14, wherein said conditional origin of replication comprises or consists of the sequence SEQ ID NO: 7 or SEQ ID NO: 8.
16. The method according to any of embodiments 1-15, wherein said genetic modification is a point mutation.
17. The method according to any of embodiments 1-16, wherein said genetic modification is a point mutation leading to gene disruption.
18. The method according to any of embodiments 1-17, wherein the bacteria with the genetic modification does not have a reduced in vivo growth rate as compared to the same bacteria without the genetic modification.
19. The method according to any of embodiments 1-18, wherein the genetic modification is in a bacterial toxin gene.
20. The method according to embodiment 19, comprising a genetic modification of the ClbP gene in pks+ *E. coli* that results in a single-amino acid mutation and the inactivation of the genotoxic activity of Colibactin toxin, but maintains the antagonistic activity.
21. The method according to embodiment 20, comprising a genetic modification at S95 or K98 of the ClbP gene.
22. The method according to embodiment 21, comprising a genetic modification of S95A, S95R or K98T.
23. The method according to any of embodiments 1-18, wherein the genetic modification is in the *Bacteroides faecis* or *Bacteroides thetaiotaomicron* beta-galactosidase gene.
24. The method according to embodiment 16, wherein the *Bacteroides faecis* or *Bacteroides thetaiotaomicron* beta-galactosidase protein with the genetic modification shows lower homology with human MYH6 cardiac peptide as compared to the *Bacteroides faecis* or *Bacteroides thetaiotaomicron* beta-galactosidase protein without the genetic modification.
25. The method according to any of embodiments 1-18, wherein the genetic modification is in *Propionibacterium propionicum* Ro60 orthologs.
26. The method according to embodiment 25, wherein the genetic modification is in at least one *Propionibacterium propionicum* Ro60 ortholog epitope leading to weaker or no recognition by the human immune system.
27. The method according to any of embodiments 1-26, comprising genetically modifying at least one gene in the naturally occurring bacteria in situ in a human.
28. A method of modulating host—microbiome interaction by genetically modifying naturally occurring bacteria in situ wherein said naturally occurring bacteria is involved in microbiome associated disorder or disease comprising:
   genetically modifying a DNA sequence responsible for the microbiome associated disorder or disease in the naturally occurring bacteria in situ without introducing a double strand break in the DNA sequence,
   wherein said genetic modification reduces the effects of the microbiome associated disorder or disease, and
   wherein said genetic modification does not lead to the death of bacteria.
29. The method according to embodiment 28, wherein the bacteria with the genetic modification does not have a reduced in vivo growth rate as compared to the same bacteria without the genetic modification.
30. A method to prevent or intervene in the course of an auto-immune disease/reaction in a predisposed host by modifying the immunogenic profile of a bacterial population of the host microbiome, comprising:
   contacting the bacterial population with a vector that generates a genetic modification in a DNA sequence coding for an immunogenic component expressed or secreted by the bacteria in at least some of the bacteria of said population without introducing a double strand break in the DNA sequence,
   wherein the genetic modification of the gene coding for the immunogenic component results in loss of its immunogenic component;
   wherein genetic modification does not lead to the direct death of the bacteria.
31. The method according to embodiment 30, wherein the bacteria with the genetic modification does not have a reduced in vivo growth rate as compared to the same bacteria without the genetic modification.

32. The method according to embodiment 30 comprising contacting said bacteria with a phagemid encoding an enzyme that modifies the genome of said bacteria.

33. The method according to embodiment 30, comprising contacting said bacteria with a phagemid encoding an enzyme that is a base-editor.

34. The method according to embodiment 30, comprising contacting said bacteria with a phagemid encoding an enzyme that is a prime-editor.

35. The method according to any of embodiments 28 or 30, wherein the genetic modification is a point mutation that results in a change of amino-acid in a mimic peptide and renders the mimic peptide not immunogenic and/or not recognized by the immune system.

36. The method according to embodiment 28, wherein the genetic modification results in a change of sugar profile on the bacterial membrane.

37. The method according to embodiment 28, wherein the genetic modification results in a change of amino acid in a protein sequence that in turn results in a change of sugar profile on the bacterial membrane.

38. The method according to embodiment 28, wherein the genetic modification results in a change of lipid profile on the bacterial membrane.

39. The method according to embodiment 28, wherein the genetic modification results in a change of amino acid in a protein sequence that in turn results in a change of lipid profile on the bacterial membrane.

40. The method according to any of embodiments 1-30, wherein the genetic modification renders a catalytic site inactive.

41. The method according to any of embodiments 1-30, wherein the genetic modification renders a binding site with a human cell receptor non-functional.

42. The method according to any of embodiments 1-30, wherein the genetic modification renders the bacteria more sensitive to detection by human immune cells.

43. A method for screening for genetic modifications in bacteria comprising:
administering, to a subject, a vector designed to genetically modify at least one base of a DNA sequence of interest in a gene of a naturally occurring bacteria without introducing a double strand break in the DNA sequence,
subsequently collecting a bacterial sample from the subject, and
quantitating the level of bacteria containing a genetic modification in said at least one base of a DNA sequence of interest in said bacterial sample.

44. The method according to embodiment 43, further comprising quantitating the level of bacteria not containing a genetic modification in said at least one base of a DNA sequence of interest.

45. A method for determining the efficiency of a vector at inducing genetic mutations in situ comprising:
administering, to a subject, a vector designed to genetically modify at least one base of a DNA sequence of interest in a gene of a naturally occurring bacteria without introducing a double strand break in the DNA sequence,
subsequently collecting a bacterial sample from the subject,
quantitating the level of bacteria containing a genetic modification in said at least one base of a DNA sequence of interest, and quantitating the level of bacteria not containing a genetic modification in said at least one base of a DNA sequence of interest in said bacterial sample.

46. A method for determining the effect of a genetic mutation on bacterial growth comprising:
administering, to a subject, a vector designed to genetically modify at least one base of a DNA sequence of interest in a gene of a naturally occurring bacteria, without introducing a double strand break in the DNA sequence,
subsequently collecting at least two sequential bacterial samples from the subject,
quantitating the level of bacteria containing a genetic modification in said at least one base of a DNA sequence of interest and quantitating the level of bacteria not containing a genetic modification in said at least one base of a DNA sequence of interest in said bacterial samples.

47. The method according to any of embodiments 43 to 46, comprising a genetic modification of the ClbP gene in pks+ E. coli that results in a single-amino acid mutation and the inactivation of the genotoxic activity of Colibactin toxin, but maintains the antagonistic activity.

48. An engineered bacteriophage for modifying a naturally occurring bacteria in situ comprising a nucleic acid encoding a gene editing enzyme/system for transformation of a target bacteria in a mixed bacterial population wherein said gene editing enzyme/system modifies the genome of said target bacteria without introducing a double strand break in the DNA sequence, but does not lead to the death of the target bacteria.

49. The bacteriophage according to embodiment 48 for use for treating a disease or disorder, wherein the gene editing enzyme/system targets a gene within the target bacteria encoding a protein which is directly or indirectly responsible for said disease or disorder.

50. A method to modify the metabolism of a given drug in a host treated with said drug, by modifying at least one drug-targeting enzyme expressed by a bacterial population of the host microbiome, comprising:
contacting the bacterial population with a vector that generates a genetic modification in a DNA sequence coding for a drug-targeting enzyme expressed or secreted by the bacteria in at least some of the bacteria of said population without introducing a double strand break in the DNA sequence,
wherein the genetic modification of the DNA sequence coding for the drug-targeting enzyme results in a modification of the drug metabolism in the host;
wherein genetic modification does not lead to the direct death of the bacteria.

DEFINITIONS

«Vector»

As used herein, the term "vector" refers to any construct of sequences that are capable of expression of a polypeptide in a given host cell. If a vector is used then the choice of vector is dependent upon the method that will be used to transform host bacteria as is well known to those skilled in the art. Vectors can include, without limitation, plasmid vectors and recombinant phage vectors, or any other vector known in that art suitable for delivering a polypeptide of the invention to target bacteria. The skilled artisan is well aware of the genetic elements that must be present on the vector in order to successfully transform, select and propagate host cells comprising any of the isolated nucleotides or nucleic acid sequences of the invention.

«Delivery Vehicle»

As used herein, the term «delivery vehicle» refers to any vehicle that allows the transfer of a payload or vector into a bacterium.

There are several types of delivery vehicle encompassed by the present invention including, without limitation, bacteriophage scaffold, virus scaffold, bacterial virus particle, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation).

Any combination of delivery vehicles is also encompassed by the present invention.

The delivery vehicle can refer to a bacteriophage derived scaffold and can be obtained from a natural, evolved or engineered capsid.

In some embodiment, the delivery vehicle is the payload or vector as bacteria are naturally competent to take up a payload or vector from the environment on their own.

«Payload»

As used herein, the term «payload» refers to any nucleic acid sequence or amino acid sequence, or a combination of both (such as, without limitation, peptide nucleic acid or peptide-oligonucleotide conjugate) transferred into a bacterium with a delivery vehicle.

The term «payload» may also refer to a plasmid, a vector or a cargo.

The payload can be a phagemid or phasmid obtained from natural, evolved or engineered bacteriophage genome. The payload can also be composed only in part of phagemid or phasmid obtained from natural, evolved or engineered bacteriophage genome.

In some embodiment, the payload is the delivery vehicle as bacteria are naturally competent to take up a payload from the environment on their own.

«Nucleic Acid»

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphosphoroamidite linkage and/or deoxyribonucleotides and ribonucleotides nucleic acids. Any combination of the above features of a nucleic acid is also encompassed by the present invention.

"Phagemid" and "Packaged Phagemid"

As used herein, the term "phagemid" or "phasmid" are equivalent and refer to a recombinant DNA vector comprising at least one sequence of a bacteriophage genome and which is preferably not able of producing progeny, more particularly a vector that derives from both a plasmid and a bacteriophage genome. A phagemid of the disclosure comprises a phage packaging site and optionally an origin of replication (ori), in particular a bacterial and/or phage origin of replication. In one embodiment, the phagemid does not comprise a origin of replication and thus cannot replicate by itself once injected into a bacterium. Alternatively, the phagemid comprises a plasmid origin of replication, in particular a bacterial and/or phage origin of replication.

As used herein, the term "packaged phagemid" refers to a phagemid which is encapsidated in a bacteriophage scaffold, bacterial virus particle or capsid. Particularly, it refers to a bacteriophage scaffold, bacterial virus particle or capsid devoid of a wild-type bacteriophage genome. The packaged phagemid may be produced with a helper phage strategy, well known from the man skilled in the art. The helper phage comprises all the genes coding for the structural and functional proteins that are indispensable for the phagemid according to the invention to be encapsidated. The packaged phagemid may be produced with a satellite virus strategy, also known from the man skilled in the art. Satellite virus are subviral agent and are composed of nucleic acid that depends on the co-infection of a host cell with a helper virus for all the morphogenetic functions, whereas for all its episomal functions (integration and immunity, multicopy plasmid replication) the satellite is completely autonomous from the helper. In one embodiment, the satellite genes can encode proteins that promote capsid size reduction of the helper phage, as described for the P4 Sid protein that controls the P2 capsid size to fit its smaller genome.

«Peptide»

As used herein, the term "peptide" refers both to a short chain of at least 2 amino acids linked between each other and to a part of, a subset of, or a fragment of a protein which part, subset or fragment being not expressed independently from the rest of the protein. In some instances, a peptide is a protein. In some other instances, a peptide is not a protein and peptide only refers to a part, a subset or a fragment of a protein. Preferably, the peptide is from 4, 5, 6, 7, 8, 9, 10, 11, 12, 13, 14, 15 amino acids to 4, 5, 6, 7, 8, 9, 10, 11, 12, 13, 14, 15, 20, 25, 30, 40, 50, 100, 200 amino acids in size.

"Homology" and "Identity"

By "homology" is meant herein the amino acid sequence of two or more amino acid molecules is partially or completely identical. In certain embodiments the homologous amino acid sequence has 30%, 40%, 50%, 60%, 70%, 80%, 90%, or 95% sequence similarity or identity to the amino acid sequence of reference.

As used herein, the percent homology between two sequences is equivalent to the percent identity between the two sequences. The percent identity is calculated in relation to polymers (e.g., polynucleotide or polypeptide) whose sequences have been aligned. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4: 11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using a BLOSUM62 matrix, a BLOSUM30 matrix or a PAM250 matrix, and a gap weight of 16, 14, 12, 10, 8, 6, or 4 and a length weight of 1, 2, 3, 4, 5, or 6. In a specific embodiment the BLOSUM30 matrix is used with gap open penalty of 12 and gap extension penalty of 4.

Brief description of the sequences

| SEQ ID NO: | Description | Type |
|---|---|---|
| 1 | Payload encoding Adenine base editor (ABE8e) and guideRNA targeting mCherry | DNA |
| 2 | Payload encoding Adenine base editor (ABE8e) and guideRNA targeting ß-lactamase | DNA |
| 3 | Payload encoding Cytosine base editor (evoAPOBEC1-nCas9-UGI) and guideRNA targeting mCherry | DNA |
| 4 | Payload encoding Cytosine base editor (evoAPOBEC1-nCas9-UGI) and guideRNA targeting ß-lactamase | DNA |
| 5 | mCherry gene | DNA |
| 6 | ß-lactamase gene | DNA |
| 7 | Primase ori deltaGAAABCC | DNA |
| 8 | Primase ori devoid of restriction sites | DNA |
| 9 | insulin B9-25 epitope | Protein |
| 10 | T cell (β2GPI) epitope | Protein |
| 11 | B cell epitope | Protein |
| 12 | primase ori from the PICI of the *Escherichia coli* strain CFT073 | DNA |
| 13 | Restriction site | DNA |
| 14 | PICI primase-helicase | Protein |
| 15 | PICI primase-helicase | DNA |
| 16 | Ro60 B cell epitope | Protein |
| 17 | Ro60 T cell epitope (aa 316-335) | Protein |
| 18 | Ro60 T cell epitope (aa 369-383) | Protein |
| 19-2313 | Candidate mimic peptides | Protein |
| 2314 | RFP gene | DNA |
| 2315 | Payload encoding prime editor (PE) and pegRNA targeting RFP | DNA |
| 2316 | ClbP | Protein |
| 2317 | ClbP gene | DNA |
| 2318 | FimH | Protein |
| 2319 | FimH gene | DNA |
| 2320 | Blc | Protein |
| 2321 | Blc gene | DNA |
| 2322 | beta-galactosidase | Protein |
| 2323 | beta-galactosidase gene | DNA |
| 2324 | MYH6$_{614-629}$ | Protein |
| 2325 | Payload encoding prime editor (PE) and pegRNA targeting RFP and containing an inducible promoter | DNA |

EXAMPLES

Example 1—Method to Prevent Colorectal Cancer

A phagemid is generated containing a phage packaging site, a base editor enzyme containing a dCas9 or nCas9 fused to a deaminase domain for inducing genetic modifications or a primer editor enzyme containing a dCas9 or nCas9 fused to a reverse transcriptase domain for inducing genetic modifications.

Packaged phagemids are produced following a standard thermal induction protocol[26].

The packaged phagemid contacting the bacteria results in single-amino acid mutations of the ClbP gene in pks+ *E. coli* and the inactivation of the genotoxic activity of the Colibactin toxin, but maintains the antagonistic activity of the toxin. The single-amino acid mutations of the ClbP gene in pks+ *E. coli* are a genetic modification selected from the group consisting of S95A, S95R and K98T[1]. The bacteriophage vector is produced in *E. coli* to high titers and a pharmaceutical composition is prepared. The pharmaceutical composition is administered to human patients to generate in-situ genetic modification of the pks+ *E. coli* of the patient. The administration results in a population of *E. coli* in the patient in which the genotoxic activity of the Colibactin toxin has been inactivated, but the antagonistic activity of the toxin is maintained. Additional administrations over time further result in a diminution of the percentage of *E. coli* in the patient having a Colibactin toxin with genotoxic activity, while increasing the percentage of *E. coli* in the patient having a Colibactin toxin without genotoxic activity. In this way, the exposure of the patient to the negative effects of the genotoxic activity of the Colibactin toxin can be minimized.

Example 2—Method to Stop the Progression of Myocarditis

A method to stop the progression of myocarditis towards lethal cardiomyopathy by in situ genetic modification of the peptidic sequence of *Bacteroides faecis* or *Bacteroides thetaiotaomicron* beta-galactosidase that shows high homology with human MYH6 cardiac peptide is developed[2].

A phagemid is generated containing a phage packaging site, a base editor enzyme containing a dCas9 or nCas9 fused to a deaminase domain for inducing genetic modifications or a primer editor enzyme containing a dCas9 or nCas9 fused to a reverse transcriptase domain for inducing genetic modifications.

Packaged phagemids are produced following a standard thermal induction protocol[26].

The packaged phagemid contacting the bacteria results in single-amino acid mutations in the peptidic sequence of *Bacteroides faecis* or *Bacteroides thetaiotaomicron* beta-galactosidase that decreases its homology with human MYH6 cardiac peptide, but maintains the activity of the enzyme. Multiple single-amino acid mutations are analyzed, starting with conservative mutations. The bacteriophage vector is produced in *E. coli*. to high titers and a pharmaceutical composition is prepared. The pharmaceutical composition is administered to human patients to generate in-situ genetic modification of the *Bacteroides* of the patient. The administration results in a population of *Bacteroides* in the patient in which the peptidic sequence of *Bacteroides faecis* or *Bacteroides thetaiotaomicron* beta-galactosidase has decreased homology with human MYH6 cardiac peptide. Additional administrations over time further result in a diminution of the percentage of *Bacteroides* in the patient having a peptidic sequence of *Bacteroides* beta-galactosidase with high homology with human MYH6 cardiac peptide, while increasing the percentage of *Bacteroides* in the patient having a peptidic sequence of *Bacteroides* beta-galactosidase with low homology with human MYH6 cardiac peptide. In this way, the exposure of the patient to the negative auto-immune effects caused by the immune cross-reactivity of the *Bacteroides* protein and the human MYH6 cardiac peptide can be minimized.

Example 3—Screening of Vectors

A phagemid is generated containing a phage packaging site, a base editor enzyme containing a dCas9 or nCas9 fused to a deaminase domain for inducing genetic modifications or a primer editor enzyme containing a dCas9 or nCas9 fused to a reverse transcriptase domain for inducing genetic modifications.

Packaged phagemids are produced following a standard thermal induction protocol[26].

The packaged phagemid contacting the bacterial population results in single-amino acid mutations of the ClbP gene in pks+ *E. coli* and the inactivation of the genotoxic activity of the Colibactin toxin. The single-amino acid mutations of the ClbP gene in pks+ *E. coli* will be a genetic modification selected from the group consisting of S95A, S95R and K98T[1].

The phagemid will be contacted with pks+ *E. coli* in vitro. The growth of modified and non-modified *E. coli* will be tested in liquid and solid culture with routine culture techniques to determine the effect of the modifications on growth in vitro.

The phagemid vectors will be then produced in *E. coli*. to high titers and a pharmaceutical composition will be prepared.

The pharmaceutical composition will be administered to a subject mouse to generate in-situ genetic modification of the pks+ *E. coli* of the mouse.

Fecal samples will be collected at daily timepoints and tested by PCR and sequencing to quantitate the levels of modified and un-modified *E. coli*. to determine the percentages of each over time. The comparison of levels of modified and un-modified *E. coli* over time allows for screening for the genetic modifications in the bacteria, for determining the efficiency of vectors at inducing these genetic mutations, and for determining the effects of these mutations on bacterial growth.

Example 4—Editing of Commensals Bacteria Expressing Ro60 Orthologue for Systemic Lupus Erythematosus (SLE) or Subacute Cutaneous Lupus Erythematosus (SCLE) Prevention or Treatment A method to stop the apparition or progression of systemic lupus erythematosus (SLE) or subacute cutaneous lupus erythematosus (SOLE), by in situ genetic modification of the bacterial Ro60 orthologs, more specifically the epitopes of these orthologs.

A phagemid is generated containing a phage packaging site, a base editor enzyme containing a dCas9 or nCas9 fused to a deaminase domain for inducing genetic modifications or a primer editor enzyme containing a dCas9 or nCas9 fused to a reverse transcriptase domain for inducing genetic modifications.

Packaged phagemids are produced following a standard thermal induction protocol[26].

The packaged phagemid contacting the bacterial population results in amino acid mutations in the peptidic sequence of the bacterial Ro60 orthologs that decreases its homology with human Ro60 peptide, but maintains the activity of the enzyme. Multiple single-amino acid mutations are analyzed, starting with conservative mutations. The bacteriophage vector is produced to high titers and a pharmaceutical composition is prepared. The pharmaceutical composition is administered to human patients to generate in-situ genetic modification of the patient. The administration results in one or several amino acid mutations in epitope regions of R060 orthologue for one or several commensal bacteria such as *Propionibacterium propionicum*.

The mutation is one or several non-synonymous mutations in:
the Ro60 B cell epitope (aa 169-190) (TKYKQRNGWSHKDLLRLSHLKP, SEQ ID NO: 16), more specifically the amino acid change will be in the bolded amino acids (TKYKQRNGWSHKDLLRLSHLKP, SEQ ID NO: 16).
- the Ro60 T cell epitope (aa 316-335) (KARIHPFHILIALETYKTGH, SEQ ID NO: 17) more specifically the amino acid change will be in the bolded amino acids (KARIHPFHILIALETYKTGH, SEQ ID NO: 17).
- the Ro60 T cell epitope (aa 369-383) (KRFLAAVDVSASMNQ, SEQ ID NO: 18) more specifically the amino acid change will be in the bolded amino acids (KRFLAAVDVSASMNQ, SEQ ID NO: 18).

A non-limiting list of human commensal bacteria whose genome contains a Ro60 ortholog is: *Actinomyces massiliensis* F0489 (HMPREF1318_2237), *Actinomyces* sp. Oral taxon 414 (AM609_00765), *Corynebacterium amycolatum* SK46 (CORAM0001_1910), *Mycobacterium smegmatis* (strain ATCC 700084/mc(2)155) (MSMEG_1193), *Parascardovia denticolens* IPLA 20019 (A200_07914), *Propionibacterium* prop F0230a (HMPREF9154_0590), *Segniliparus rugosus* ATCC BAA-974 (HMPREF9336_02315), *Streptomyces* sp. HGB0020 (HMPREF1211_06263), *Bacteroides theta* 7330 (Btheta7330_01248), *Chryseobacterium gleum* ATCC 35910 (HMPREF0204_10833), *Prevotella* sp. CAG:1092 (BN465_02442), *Clostridium* sp. BL8 (M918_10850), Paenibacillussp. HGF7 (HMPREF9413_2200), *Paenibacillus* sp. HGH0039 (HMPREF1207_01859), *Eikenella corrodens* ATCC 23834 (EIKCOROL_00065), *Kingella oralis* ATCC 51147 (GCWU000324_03050), *Neisseria elongata* subsp. glycolytica ATCC 29315 (NEIELOOT_02899), *Neisseria flavescens* strain CD-NF1 (TV01_0020), *Neisseria macacae* ATCC 33926 (HMPREF9418_1500), *Neisseria mucosa* strain C6A (E517_04055), *Neisseria shayeganii* 871 (HMPREF9371_0707), *Neisseria sicca* ATCC 29256 (NEISICOT_02760), *Neisseria* sp. GT4A_CT1 (HMPREF1028_01178), *Neisseria* sp. oral taxon 020 str. F0370 (HM PREF9120_02756), *Neisseria subflava* NJ9703 (NEISUBOT_04391), *Cardiobacterium valvarum* F0432 (HMPREF9080_02018), *Synergistes* sp. 3_1_syn1 (HMPREF1006_01942).

More preferably the human commensal bacteria targeted by bacteriophage vector are: *Propionibacterium propionicum, Corynebacterium amycolatum, Actinomyces massiliensis, Bacteroides thetaiotaomicron.*

Example 5—Editing of Pathogenic *Escherichia coli* In Situ

*E. coli* is a commensal enterobacteria but specific strains have been associated with numerous pathology inside and outside the gut among which inflammatory bowel disease (IBD), urinary tract infection (UTI), Hemolytic uremic syndrome (HUS), Gastroenteritis or colorectal cancer. The pathogenicity of these specific strains originates from virulence genes some of which are acquired by horizontal gene transfer such as shiga toxin genes (stx) carried by temperate phages or by mutations in specific genes.

A method to reduce or abolish the pathogenic properties of the gut bacteria *Escherichia coli* by in situ genetic modification of peptidic sequence of virulence gene notably genes involved in the inflammatory properties of *E. coli* is described below.

A phagemid is generated containing a phage packaging site, a base editor enzyme containing a dCas9 or nCas9 fused to a deaminase domain for inducing genetic modifications or a primer editor enzyme containing a dCas9 or nCas9 fused to a reverse transcriptase domain for inducing genetic modifications. Packaged phagemids are produced following a standard thermal induction protocol[26].

The phagemid contact the bacterial population resulting in the mutation of one or several non-synonymous mutations in:

- the FimH gene that results in reverting the following mutations: N70S and S78N associated with AEIC strains[3].
- the ChiA gene that results in reverting the following mutations: K362Q, K370E, A378V, E388V, V548E[24]
- the OmpA gene that results in reverting the following mutation: A200V[25]
- the OmpC gene that results in reverting the following mutation: V220I, D232A[25]
- the OmpF gene that results in reverting the following mutation: E51V, M60K[25]
- the blc gene in *E. coli* that results in reverting the following mutation G84E (G251A at the nucleotide level) potentially associated to gut inflammation[4]

Example 6—Editing of *Staphylococcus epidermidis* In Situ

*Staphylococcus epidermidis* is with *Cutibacterium acnes* one of the two most prevalent and abundant commensal bacteria on the human skin. As such it has been shown to prevent colonization by pathogenic bacteria like its close relative *Staphylococcus aureus*, prevent skin cancer or also modulate the human immune system. However, it is also a growing concern due to its opportunistic pathogenic characteristic and its growing resistance to antibiotics. These pathogenic traits of *S. epidermis* might be encoded on specific virulence genes or cluster and some of these might spread across strains by horizontal gene transfer.

A method to reduce or abolish the pathogenic properties of *S. epidermidis* by in situ genetic modifications of peptidic sequences of virulence genes is described below.

A phagemid is generated containing a phage packaging site, a base editor enzyme containing a dCas9 or nCas9 fused to a deaminase domain for inducing genetic modifications or a primer editor enzyme containing a dCas9 or nCas9 fused to a reverse transcriptase domain for inducing genetic modifications.

Packaged phagemids are produced following a standard thermal induction protocol[26].

The packaged phagemid contacting the bacterial population results in one or several genetic mutations that lead to reduction or elimination of the pathogenicity. This can be done by for example: non-synonymous mutations, mutations leading to gene disruption such as introduction of stop codons or mutations in regulatory sequences such as promoter, transcription binding sites.

The genetic mutations is targeted towards one or several genes associated with *S. epidermidis* infection as described in Méric et al[27] and listed here: id1001_1081, SE_p608, SE0037, SE0038, SE_p609, id1001_1086, SE0058, SE_p205, SE_p603, SEA0027, SE0036, SE0033, SE0053, SE0055, SE_p522, SE_p610, SE_p611, id1001_1083, id1067_0124, id268_0008, SE0090, SE2153, id1001_0181, id1067_0123, id1074_1993, SE0023, SE0030, SE0103, SE0120, SE0129, SE_p607, SEA0003, id1001_2175, id1001_2181, SE0031, SE0069, SE0076, SE0107, SE0115, SE_p602, SE_p606, SEA0022, SEA0030, id2_1533, id1001_0179, id1001_0180, id1001_0186, id1001_0194, id1001_0203, id1001_2173, id1001_2184, id1001_2209, id1067_0125, id1067_0126, id1074_0268, id1075_0004, id1092_0129, SE0004, SE0020, SE0114, SE0127, SE0282, SE1013, SE1106, SE1292, SE2395, SE_p605, SEA0004, SEA0008, id1001_0187, id1001_2183, id1001_2208, id1021_0918, id1074_0267, SE0005, SE0021, SE0050, SE0063, SE0118, SE1588, SE1632, SE1920, SE_p507, SEA0002, SEA0020, SEA0021, id1001_0910, id1001_2159, id1001_2206, id1021_0613, id1032_2361, id1032_2362, id1067_0112, id1067_0226, id1067_0227, id1067_1124, id429_2314, SE0045, SE0051, SE0054, SE0101, SE0109, SE0112, SE0116, SE0119, SE0145, SE0175, SE0803, SE0852, SE1092, SE1102, SE1103, SE1107, SE1118, SE1128, SE1429, SE1455, SE1587, SE1607, SE1983, SE2011, SE2079, SE2208, SE2251, SE2260, SE2409, SE_p103, SE_p508, SE_p521, SEA0005, id1001_0007, id1001_0010, id1001_0183, id1001_0191, id1001_0199, id1001_0912, id1001_1283, id1001_2163, id1001_2164, id1001_2169, id1001_2174, id1001_2185, id1031_0178, id1067_0113, id1074_2138, id429_2315, id429_2316, id429_2317, id429_2319, SE0001, SE0009, SE0016, SE0032, SE0071, SE0102, SE0104, SE0106, SE0108, SE0111, SE0122, SE0146, SE0148, SE0182, SE0197, SE0230, SE0231, SE0240, SE0263, SE0273, SE0306, SE0629, SE0800, SE0804, SE0805, SE0815, SE0817, SE0825, SE0828, SE1037, SE1094, SE1096, SE1105, SE1458, SE1605, SE1606, SE1613, SE1728, SE1917, SE1919, SE1921, SE2160, SE2192, SE2220, SE2257, SE_p410, id1001_0011, id1001_0182, id1001_0190, id1001_1084, id1001_1085, id1001_1264, id1001_1972, id1001_1984, id1001_1986, id1001_2203, id1005_0195, id1005_1733, id1005_1734, id1021_0933, id1021_1637, id1021_1670, id1021_1674, id1031_0580, id1031_0911, id1031_0919, id1031_0920, id1031_0922, id1031_1192, id1067_0106, id1067_0107, id1067_0111, id1067_1095, id1067_1493, id1091_1647, id505_1243, SE0002, SE0003, SE0008, SE0010, SE0019, SE0034, SE0064, SE0105, SE0110, SE0128, SE0137, SE0140, SE0157, SE0162, SE0181, SE0183, SE0186, SE0191, SE0241, SE0248, SE0253, SE0254, SE0266, SE0268, SE0307, SE0331, SE0470, SE0692, SE0693, SE0694, SE0802, SE0806, SE0841, SE0917, SE1059, SE1083, SE1090, SE1104, SE1211, SE1459, SE1598, SE1628, SE1637, SE1649, SE1770, SE1772, SE1777, SE1872, SE1897, SE1900, SE1918, SE1925, SE1926, SE1927, SE1931, SE1985, SE2021, SE2042, SE2044, SE2045, SE2091, SE2124, SE2152, SE2193, SE2201, SE2221, SE2222, SE2244, SE2246, SE2250, SE2401, SE2403, SE2408, SE_p203, SE_p206, SE_p405, SE_p406, SE_p506, SEA0001, SEA0029, id2_1530, id1001_0188, id1001_0911, id1001_1285, id1001_1982, id1005_1719, id1021_0758, id1021_0930, id1021_1658, id1021_1663, id1021_2114, id1031_1153, id1031_1190, id1031_1202, id1031_1222, id1031_1428, id1067_1094, id1067_1098, id1067_1099, id1067_1106, id1067_1135, id1091_2272, id1120_2061, id262_0707, id262_0708, id304_0202, id53_0678, SE0013, SE0015, SE0022, SE0121, SE0126, SE0135, SE0142, SE0149, SE0152, SE0185, SE0194, SE0196, SE0212, SE0226, SE0232, SE0237, SE0242, SE0243, SE0259, SE0262, SE0269, SE0272, SE0274, SE0275, SE0276, SE0278, SE0279, SE0281, SE0299, SE0305, SE0355, SE0435, SE0456, SE0604, SE0673, SE0689, SE0701, SE0704, SE0705, SE0707, SE0716, SE0779, SE0782, SE0808, SE0814, SE0818, SE0836, SE0839, SE0990, SE1082, SE1097, SE1108, SE1109, SE1122, SE1136, SE1138, SE1196, SE1207, SE1288, SE1456, SE1464, SE1546, SE1574, SE1580, SE1585, SE1589, SE1603, SE1604, SE1643, SE1735, SE1773, SE1827, SE1836, SE1899, SE1914, SE1915, SE1938, SE1946, SE2005, SE2022, SE2036, SE2041, SE2043, SE2052, SE2071, SE2074, SE2090, SE2116, SE2148, SE2149, SE2154, SE2167, SE2175, SE2194, SE2198, SE2199, SE2210, SE2215, SE2223, SE2225, SE2229, SE2259, SE2306, SE2314, SE2333, SE2337, SE2342, SE2379, SE2388, SE2394, SE_p411, SEA0006, id1001_0185, id1001_2167, id1001_2190, id1005_0702, id1005_0703, id1005_0704, id1021_0787, id1021_1631, id1021_1651, id1021_1652, id1005_1752, id1021_1667, id1021_1669, id1021_1671, id1021_1673, id1031_1154, id1031_1160, id1031_1169, id1031_1173, id1031_1179, id1031_1182, id1031_1431, id1031_2369, id1067_1117, id1067_1130, id1068_0108, id1068_0584, id1074_1751, id1074_2133, id1091_2269, id1092_1189, id267_0755, id324_1262, SE0014, SE0066, SE0117, SE0123, SE0134, SE0144, SE0163, SE0180, SE0195, SE0223, SE0229, SE0250, SE0251, SE0255, SE0261, SE0280, SE0301, SE0410, SE0444, SE0450, SE0455, SE0615, SE0637, SE0657, SE0663, SE0664, SE0669, SE0670, SE0683, SE0684, SE0690, SE0700, SE0706, SE0713, SE0785, SE0790, SE0797, SE0813, SE0816, SE0832, SE0909, SE1075, SE1080, SE1085, SE1089, SE1121, SE1132, SE1133, SE1175, SE1183, SE1184, SE1210, SE1212, SE1311, SE1348, SE1397, SE1408, SE1442, SE1460, SE1470, SE1516, SE1577, SE1581, SE1629, SE1635, SE1726, SE1727, SE1779, SE1785, SE1932, SE1949, SE1953, SE1954, SE1957, SE1959, SE1978, SE2012, SE2019, SE2023, SE2037, SE2046, SE2053, SE2054, SE2075, SE2085, SE2087, SE2088, SE2093, SE2094, SE2095, SE2114, SE2186, SE2191, SE2197, SE2213, SE2228, SE2230, SE2232, SE2242, SE2245, SE2247, SE2252, SE2253, SE2255, SE2256, SE2258, SE2298, SE2380, SE2384, SE2393, SE2396, SE2397, SE2406, SE2407, SE2411, SE2412, SE2415, SE_p409, SEA0033, id2_0245, id1001_0986, id1001_2165, id1021_0310, id1021_1615, id1021_1628, id1021_1635, id1021_1638, id1021_1654, id1021_1655, id1021_1659, id1021_1668, id1031_1165, id1031_1170, id1031_1171, id1031_1172, id1031_1174, id1031_1178, id1031_1181, id1031_1183, id1031_1224, id1031_1432, id1032_2373, id1067_1146, id1068_0610, id1074_0173, id1121_0371, id267_0744, id267_0753, id268_1096, id277_0533, id277_0629, id284_0382, id312_1160.

Preferably the genetic mutations is targeted towards one or several genes associated with S. epidermidis infection in the following list: SE0023, SE0101, SE0121, SE0128, SE0275, SE0281, SE0307, SE1105, SE1128, SE1459, SE2197, SE2245, SE2259, SE_p521, id1001_2159, id1068_0108, id1091_1647, SE0197, SE0704, SE0705, SE0706, SE0707, SE1632, SE2201, id1001_0010, SE0004, SE0030, SE0031, SE0033, SE0036, SE0050, SE0053, SE0055, SE0076, SE0090, SE0111, SE1897, id1067_0123, id1067_0124, id1067_0125, id1067_0126, id1067_0226, id1067_0227, SE0102, SE0103, SE0104, SE0105, SE0106, SE0107, SE0108, SE0110, SE0117, SE0157, SE0175, SE0673, SE0818, SE0828, SE1311, SE1637, id1067_1493, id324_1262.

Example 7—Base Editing of mCherry on the E. coli Genome after Transformation in Vitro This example presents a method for the base editing of the nucleic acid sequence encoding fluorescent protein mCherry (SEQ ID NO: 5) on the E. coli MG1655 genome after transformation with a DNA payload encoding a base editor. Fluorescence was measured by flow cytometry of individual colonies after transformation and overnight selection on chloramphenicol plates.

Figure 4A:
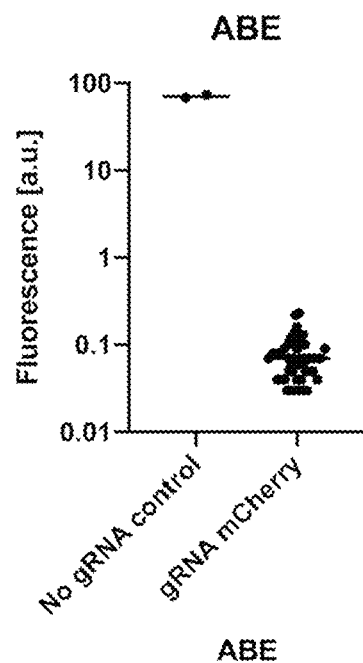
FIGS. 4A-B presents graphs showing base editing of mCherry on the *E. coli* genome after transformation in vitro.
Figure 7:
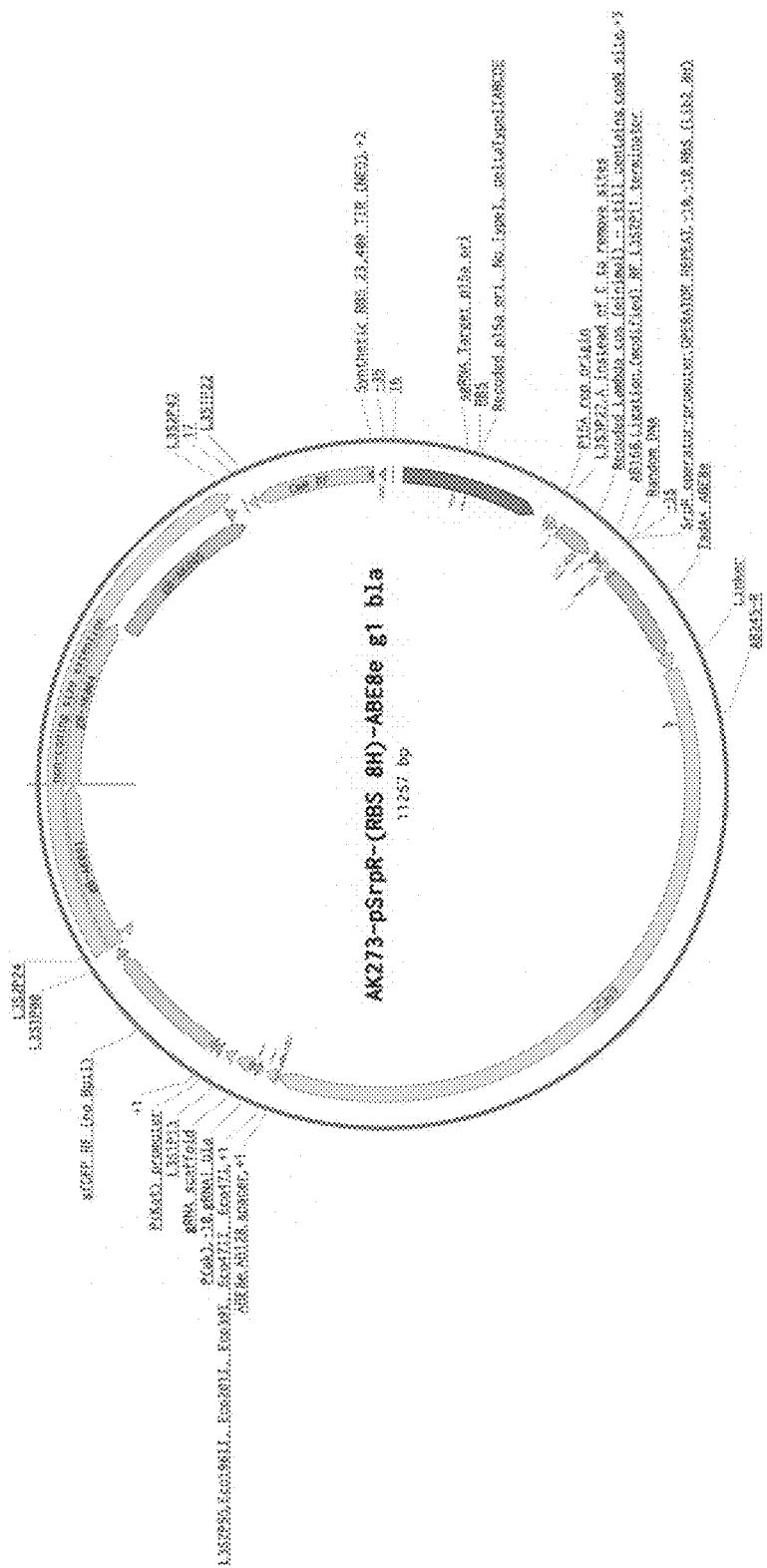
FIGS. 7 and 8 depict the plasmid maps of the constructed base editors. Adenine base editing was exemplarily performed by ABE8e (FIG. 7; SEQ ID NO: 2). ABE8e comprises an evolved TadA* gene fused to a nCas9 (D10A). Cytosine base editing was exemplarily performed by evoAPOBEC1-nCas9-UGI (FIG. 8; SEQ ID NO: 4). The UGI fused to the nCas9 (D10A) prevents the repair of U:G mismatches back into C:G base pairs. The DNA payloads carry a cos site for packaging into lambda phagemid particles.

As shown on FIG. 4A, the adenine base editor ABE8e (SEQ ID NO: 1, plasmid map shown on FIG. 7) deactivated the active site of mCherry (tripeptide: M71, Y72, G73) while enabling the translation of the full-length protein.

Figure 4B:
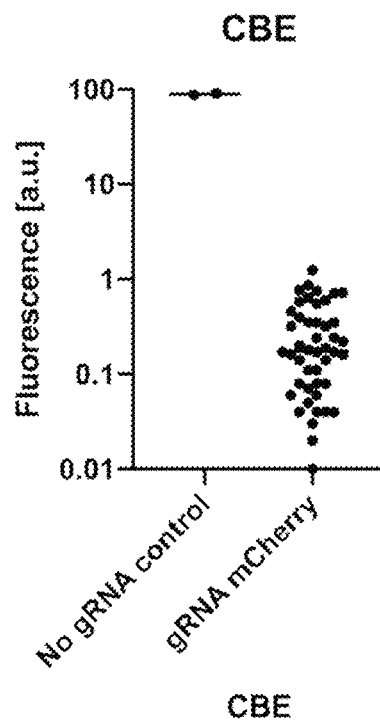
Figure 8:
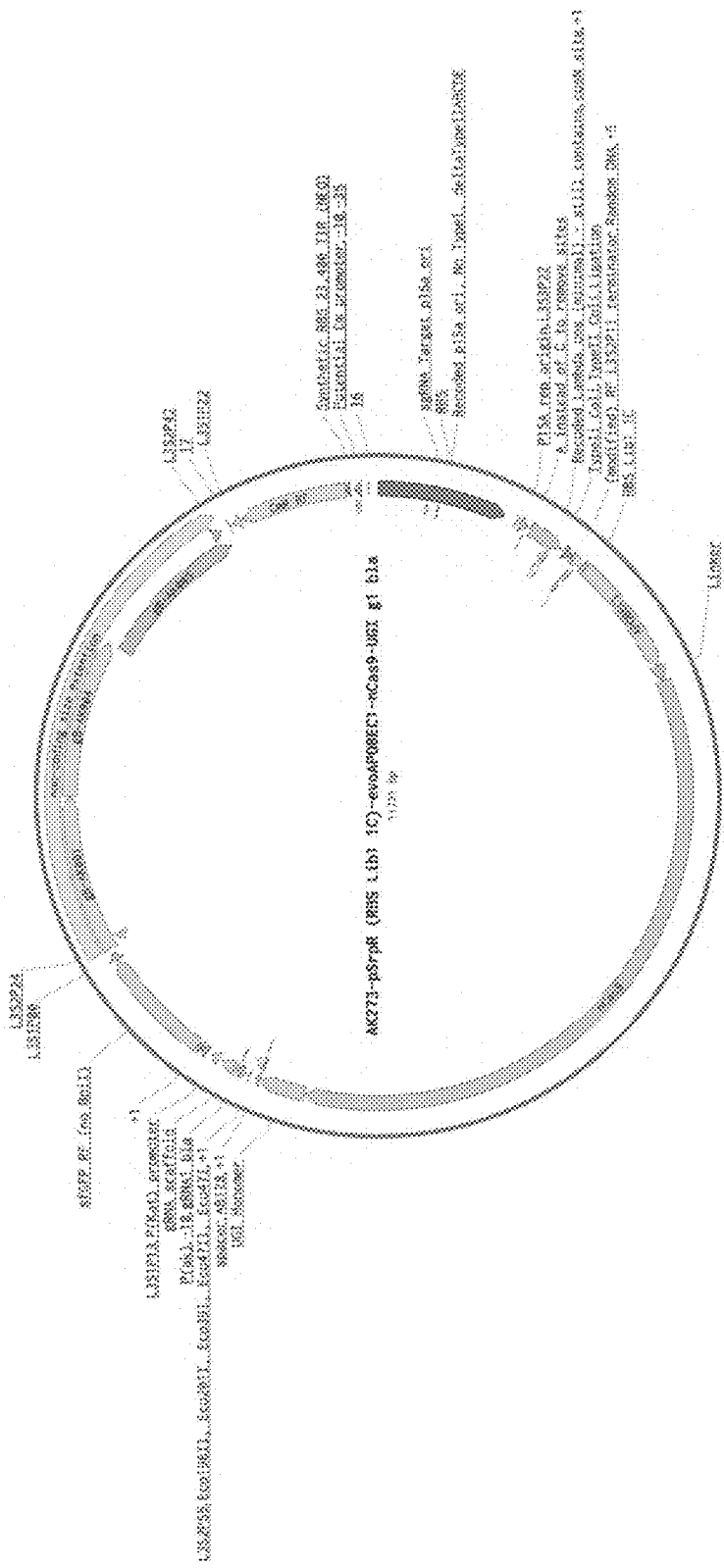

As shown on FIG. 4B, the cytosine base editor (evoAPOBEC1-nCas9-UGI; SEQ ID NO: 3, plasmid map shown on FIG. 8) inserted a stop codon (Q114) into the target gene mCherry resulting in the loss of fluorescence.

As a control, base editors were transformed in the absence of a guideRNA (2 colonies analysed) leading to fluorescent mCherry expression.

All of the 48 analysed colonies targeting mCherry via the same guideRNA were successfully edited, leading to a loss of fluorescence. The mCherry gene of five colonies was sequenced, which confirmed successful base editing.

Figure 5A:
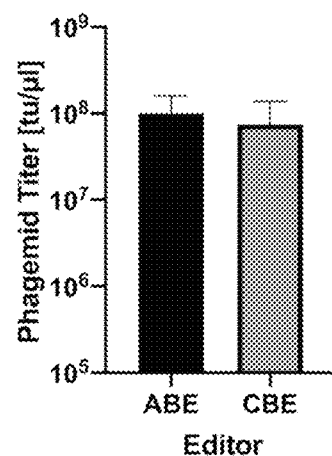
FIGS. 5A-C presents histograms and graphs showing base editing of β-lactamase on the *E. coli* genome after phagemid transduction in vitro.

Example 8—Base Editing of β-Lactamase on the E. coli Genome after Packaged Phagemid Transduction In Vitro This example presents a method for the base editing of the nucleic acid sequence encoding β-lactamase (SEQ ID NO: 6) on the E. coli MG1655 genome after packaged phagemid transduction in vitro. As shown on FIG. 5A, production of packaged lambda phagemids (within a bacterial delivery vehicle comprising an A8 gpJ protein and a P2 STF protein enabling transduction into MG1655 strain) encoding a base editor (ABE or CBE) and a transcribed guideRNA targeting the active site of the β-lactamase gene (K71E) on the genome, and further carrying a lambda packaging sequence, a chloramphenicol resistance marker, and a p15A origin of replication, resulted in titers of ~$10^8$ transduction units (tu) per µl.

Cells were plated on carbenicillin plates 2 hours post transduction in order to analyse base editing efficiency.

Figure 5B:
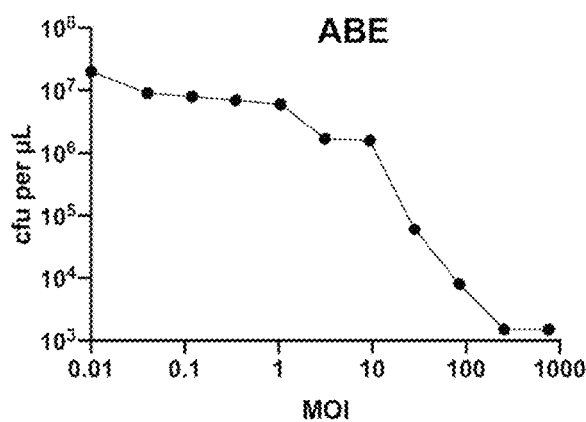
Figure 5C:
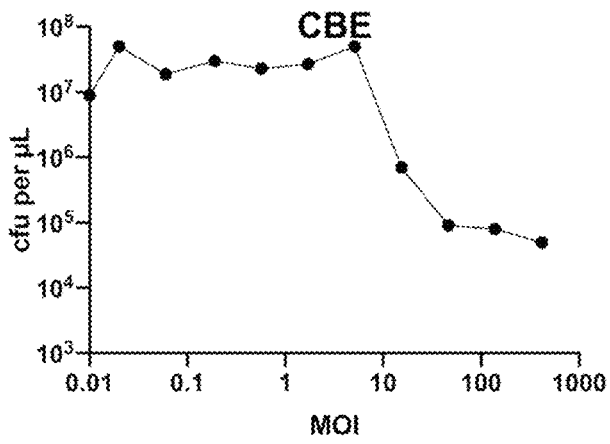

As shown on FIG. 5B, the efficiency of adenine base editing (using ABE8e; SEQ ID NO: 2) targeting the active site of the β-lactamase gene (K71E) on the genome was multiplicity of infection (MOI)-dependent. The efficiency of cytosine base editing (using evoAPOBEC1-nCas9-UGI; SEQ ID NO: 4) inserting a stop codon into the β-lactamase gene on the bacterial genome was also MOI-dependent (FIG. 5C). ABE or CBE resulted in ~4 log or ~3 log reduction of cell growth at high MOIs, respectively.

Example 9—Adenine Base Editing of β-Lactamase after Transduction into E. coli in OligoMM Mice In Vivo This example presents a method for the adenine base editing (using ABE8e, SEQ ID NO: 2) of a target gene (β-lactamase; SEQ ID NO: 6) after phagemid transduction into E. coli in an oligo-mouse-microbiota model in vivo.

The packaged phagemid titer (within a bacterial delivery vehicle comprising an A8 gpJ protein and a P2 STF protein enabling transduction into MG1655 strain) for the in vivo experiment was $1.5 \times 10^9$ transduction units per µl (tu/µl). Said phagemid carries the expressed adenine base editor ABE8e under the SrpR promoter and a constitutively transcribed guideRNA targeting the active site of the β-lacta-mase gene (K71E) on the genome. Furthermore, said phagemid carries a lambda packaging sequence, a chloramphenicol resistance marker, and a p15A origin of replication.

An *E coli* strain carrying the β-lactamase gene was administered to 10 individual mice aged 7 weeks at $10^7$ CFU per mouse. Two packaged phagemid doses (100 µl packaged phagemid+100 µl sucrose bicarbonate per mouse) were orally administered to the mice at 0 h and 30 h. Stool samples were analysed 0, 6, and 48 hours post initial phagemid transduction (48, 96, 88 colonies, respectively).

Cells were plated on streptomycin, chloramphenicol, and carbenicillin plates in order to analyse delivery and editing efficiency. Editing of the active site of β-lactamase (K71E) resulted in a loss of cell growth on carbenicillin plates.

Figure 6:
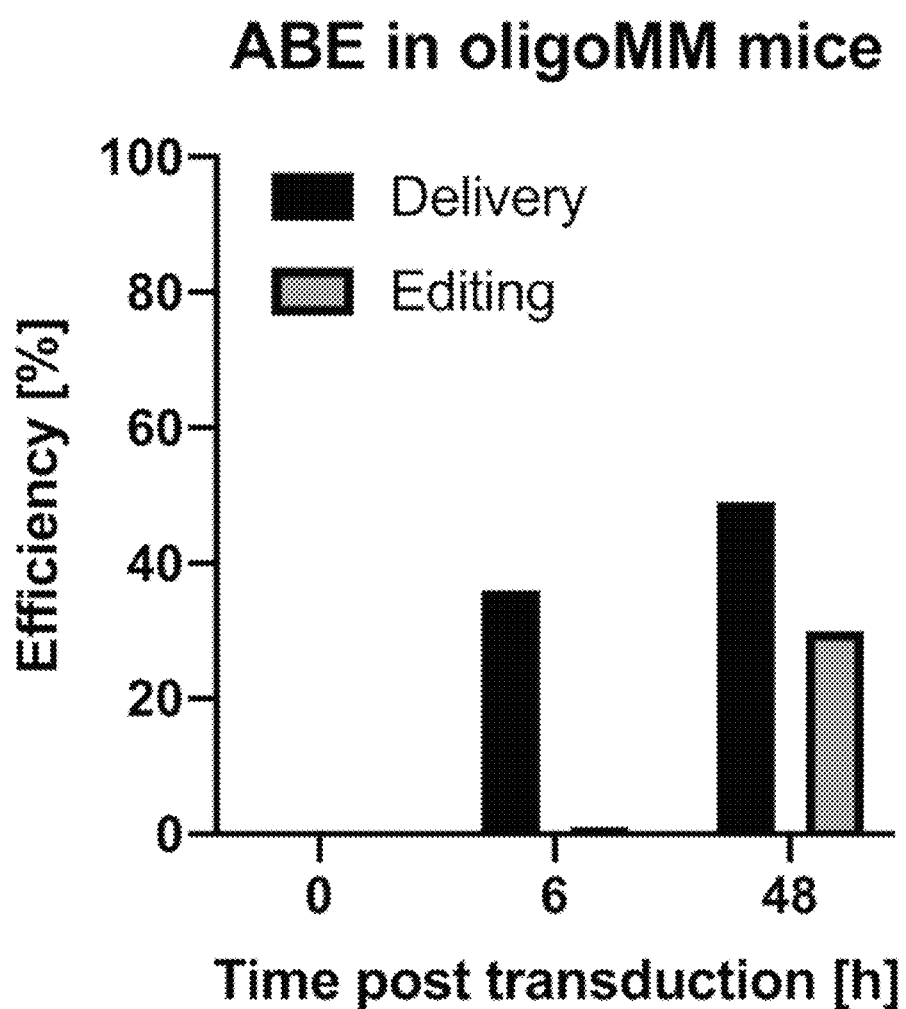
FIG. 6 presents histograms showing adenine base editing of β-lactamase after transduction into *E. coli* in oligoMM mice in vivo. The packaged phagemids titer for the in vivo experiment was $1.5 \times 10^9$ transduction units (tu)/µl. Stool samples were analysed 0, 6, and 48 hours post transduction (48, 96, 88 colonies, respectively). Cells were plated on streptomycin, chloramphenicol, and carbenicillin plates in order to analyse delivery and editing efficiency. Editing of the active site of β-lactamase (K71) results in a loss of cell growth on carbenicillin plates.

As shown on FIG. 6, after 48 hours, ~49% of the targeted bacteria population carried the DNA payload and ~30% of the whole population were base edited in vivo. The percentage of payload delivery could be further increased by higher phagemid titers and/or cumulative doses.

Figure 9:
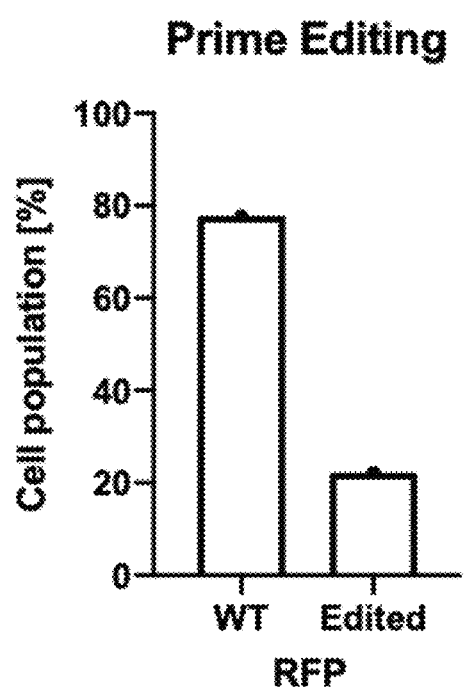
FIG. 9 displays histograms showing prime editing of Red Fluorescent Protein (RFP) on the *E. coli* genome in vitro. The genomic RFP gene was amplified from 18 individual colonies and the resulting PCR fragments were sequenced. The editing efficiency was calculated from these data.

Example 10—Prime Editing of Red Fluorescent Protein (RFP) on the *E. coli* Genome In Vitro This example presents a method for the prime editing of the nucleic acid sequence encoding the Red Fluorescent Protein RFP (SEQ ID NO: 2314) on the *E. coli* genome after transformation with a DNA payload (FIG. 9). The payload encodes a prime editor (PE; payload of sequence SEQ ID NO: 2315), a transcribed prime editing guide RNA (pegRNA), a lambda packaging sequence, a chloramphenicol resistance marker, and a p15A origin of replication. The pegRNA consists of an extended single guide RNA containing a primer binding site and a reverse transcriptase sequence in order to replace RFP's amino acid E16 (<u>G</u>AA) with a stop codon (<u>T</u>AA) on the bacterial genome.

The prime editor (PE; payload of sequence SEQ ID NO: 2315) was engineered to insert a stop codon at position E16 of the target gene RFP resulting in a loss of red fluorescence.

As a control, the prime editor was transformed in the absence of a pegRNA leading to fluorescent RFP production.

The genomic RFP gene was amplified from 18 individual colonies after transformation and overnight selection on chloramphenicol plates. The resulting PCR fragments were sequenced and the editing efficiency calculated.

As shown in FIG. 9, the stop codon was present in four of these individual colonies (~22% of the bacterial population) confirming successful prime editing.

Example 11: Description of the System Used for Non-Replicative Payloads

Figure 11:
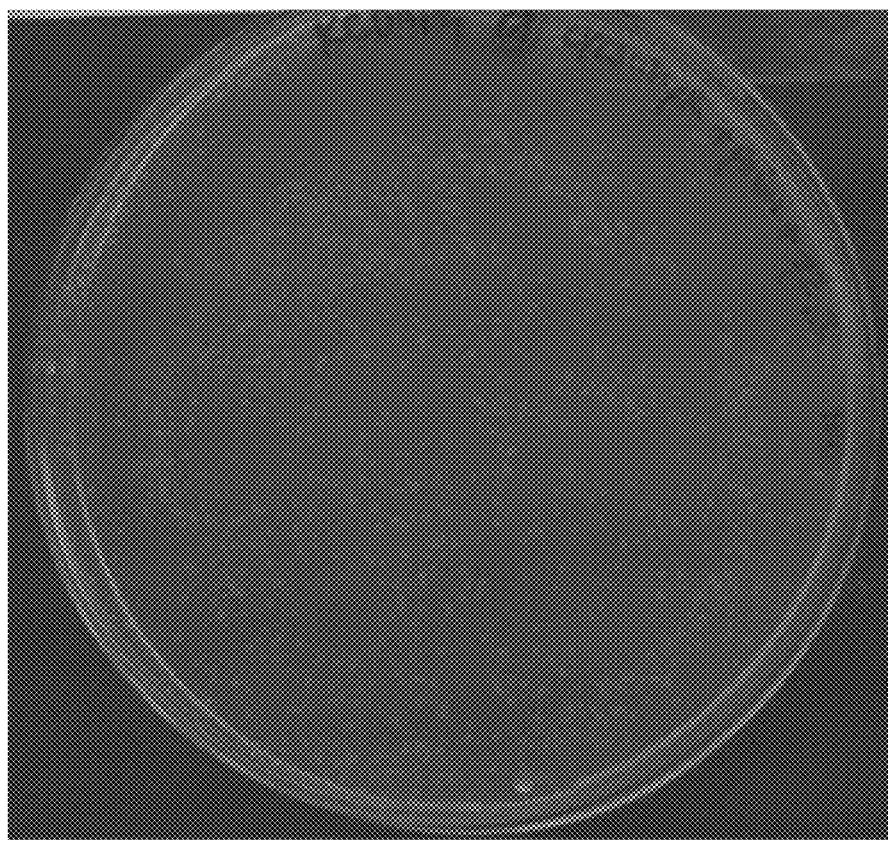
FIG. 11 displays a picture showing transformation of a 2.3 kb payload containing the primase-origin of replication in a production strain harboring an inducible primase RBS library in trans.

The inventors developed a system in which the payload contains the 282-bp primase origin and the primase protein is supplied in trans (SEQ ID NO: 8 and SEQ ID NO: 14). To simplify the engineering process, the PICI primase gene was extracted from the genome of *E. coli* CFT073, cloned into a plasmid under the control of an inducible system and an RBS (ribosome-binding site) library generated. This series of plasmids were cloned in the lambda production strain s1965. Next, the inventors constructed a small payload harboring the primase-ori instead of the p15a-based origin of replication to yield a 2.3 kb payload. Since this plasmid is, in principle, non-replicative, competent cells of s1965 harboring the RBS library of inducible primase constructs were made, the plasmid transformed in them and plated in LB agar+kanamycin and chloramphenicol in the presence of the inducer DAPG (to induce the expression of the primase in trans). Next day, the inventors observed that the plates contained hundreds of colonies, suggesting that the primase-origin system in trans works (FIG. 11).

Several clones were sequenced to verify that the plasmid contained no p15a-based origin and that they also contained an intact primase gene with an RBS coming from the library.

After that, 7 of these clones were grown overnight and lambda productions were carried out in the presence of kanamycin, chloramphenicol and DAPG. As a control, the inventors included the original 2.8 kb plasmid containing a derivative of the p15a origin of replication to compare titers.

To verify the sequence of the RBS variants obtained, the plasmid encoding the inducible primase in the 7 clones tested was miniprepped and sequenced. They were also transformed into MG1655 cells (s003): these strains were used to verify the titers obtained, since the payloads should not be replicative in the absence of the primase protein supplied in trans.

Figure 12:
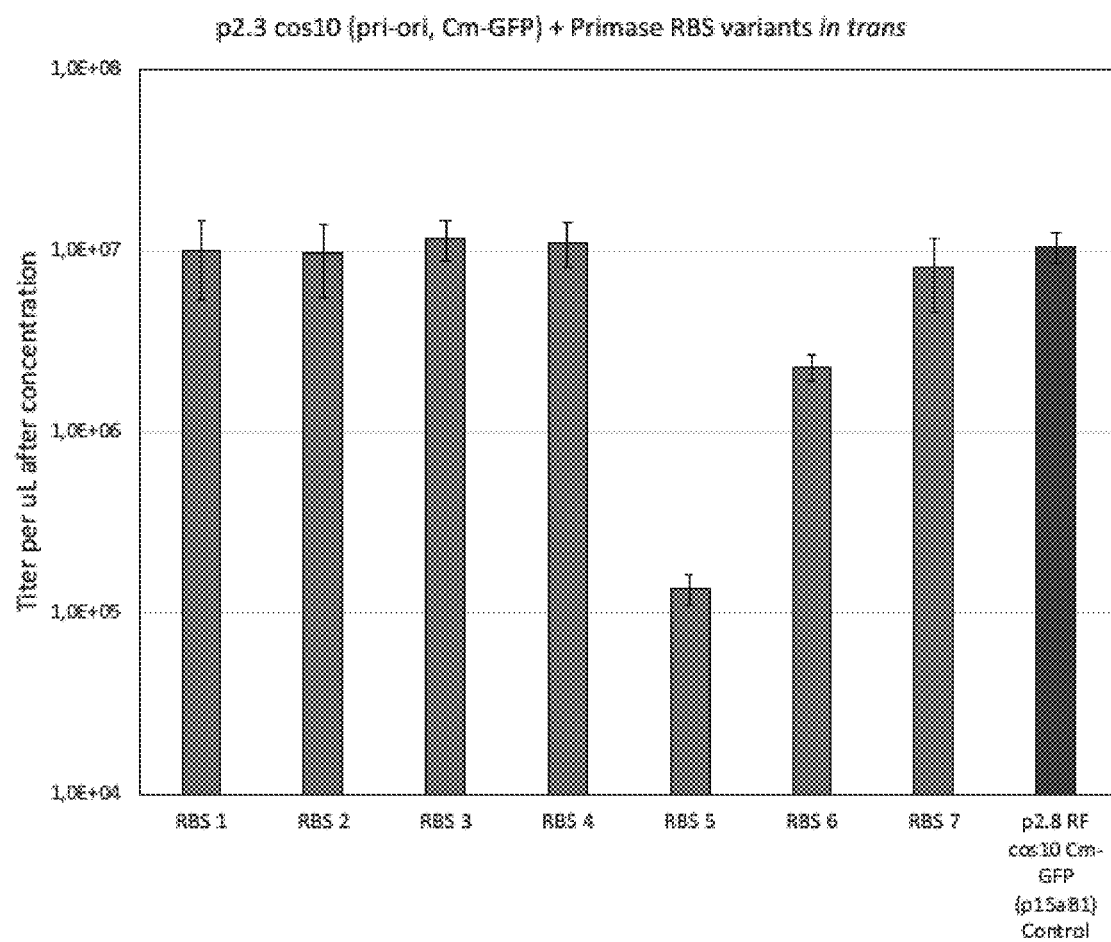
FIG. 12 displays histograms comparing packaged phagemids titers obtained with a plasmid containing the primase-ori in production strains tested against 7 different primase RBS. Right column, in black, control plasmid with a p15a-derived origin of replication. Titers shown are after a 10× concentration.

As can be seen on FIG. 12, the titers of 5 out of 7 primase-containing samples, as measured in MG1655 containing the primase plasmid in trans, were the same as those of a packaged phagemid carrying the original modified p15a origin.

Figure 13:
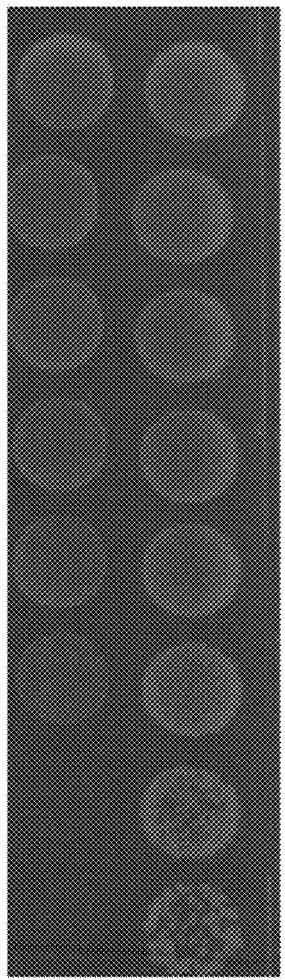
FIG. 13 displays a picture comparing cells transduced with a primase-ori plasmid (top row) and a p15a-based packaged phagemids on LB agar plus 25 μg/mL chloramphenicol.

Finally, the inventors tested if the primase-ori containing payloads could replicate in MG1655 strains without the primase plasmid in trans. To do this, serial 5× dilutions of the primase-ori containing plasmids coming from the production strains with different primase RBS, plus a p15a-origin control, were transduced into a dense culture (0D600~0.8) of MG1655 and plated on LB agar plates containing chloramphenicol. As can be seen on FIG. 13, while the p15a-origin control shows healthy colonies up to the last dilution, indicative of active plasmid replication, the samples containing the primase-containing payload show colonies only at high MOIs: since the strain will lose the payload by division, those drops that contained a high number of transduced bacteria will appear as dense spots since division will be halted at high cell densities; as the MOIs are reduced, the spots become more transparent and single colonies are hard to distinguish, indicative of cells that are dying due to plasmid loss and exposure to antibiotics. This is also indicative of a burst of expression of the chloramphenicol acetyltransferase gene upon transduction, which, in the absence of active replication, will get diluted over time; this may cause the receiver cells to survive for a certain amount of time until the intracellular concentration of chloramphenicol acetyltransferase drops below a critical level to support growth in antibiotic-supplemented media.

Figure 10:
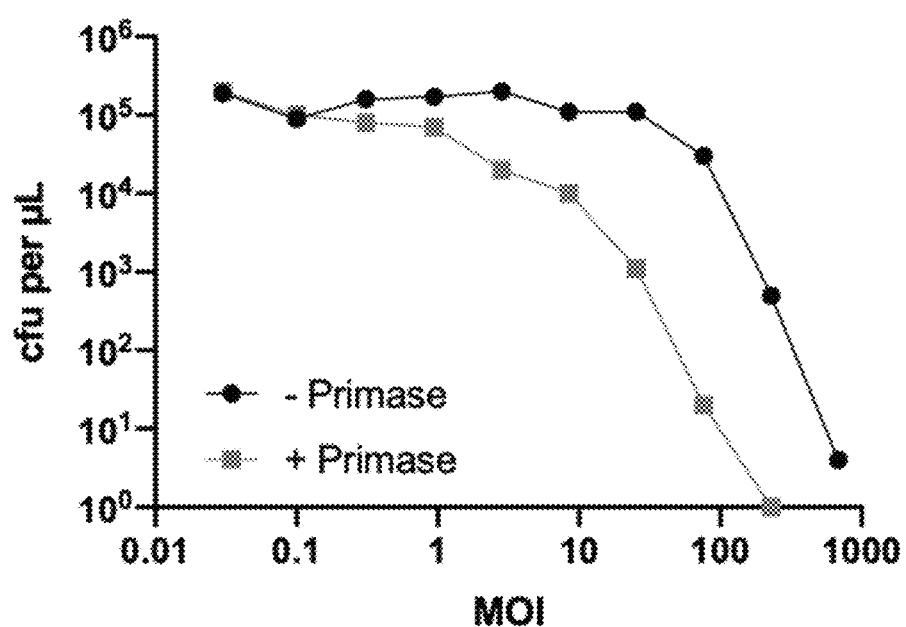
FIG. 10 displays a graph showing adenine base editing of β-lactamase on the *E. coli* genome after packaged phagemid transduction in vitro using a non-replicative payload based on a primase-helicase. An MG1655 strain encoding the β-lactamase gene was transduced in the presence or absence of the primase-helicase protein expressed inside the cell. Transduced cells were plated on LB and LB (carbenicillin) plates 2 hours post transduction at different multiplicity of infections (MOI). The next day, base editing efficiency was analyzed via colony counting.

Example 12—Adenine Base Editing of β-Lactamase on the *E. coli* Genome after Packaged Phagemid Transduction In Vitro Using a Non-Replicative Payload This example presents a method for the base editing of the nucleic acid sequence encoding β-lactamase (SEQ ID NO: 6) on the *E. coli* MG1655 genome after packaged phagemid transduction in vitro using a non-replicative payload based on a primase-helicase as disclosed in Example 11 (FIG. 10). The non-replicative payload consists of an adenine base editor (ABE8e), a transcribed guideRNA targeting the active site of the β-lactamase gene (K71E) on the genome, a lambda packaging sequence, a chloramphenicol resistance marker, and the conditional origin of replication (dependent on the presence of a primase-helicase) of sequence SEQ ID NO: 8. Production of lambda phagemids, packaged inside a bacterial delivery vehicle comprising an A8 gpJ protein and a p2 STF protein for delivery into *E. coli* MG1655, resulted in titers of 7.4×10$^7$ transduction units per µl (tu/µl).

Transduced cells were plated on LB and LB (carbenicillin) 2 hours post transduction at different multiplicity of infections (MOI). The next day, base editing efficiency was analyzed via colony counting.

As can be seen on FIG. 10, the efficiency of adenine base editing targeting the active site of the β-lactamase gene (K71E) on the genome was multiplicity of infection (MOI)-dependent. A base editing efficiency of >4 logs was obtained at high MOIs using the non-replicative payload, confirming the efficiency of base editing even using a conditional origin of replication which prevents replication of the payload inside the targeted *E. coli* MG1655 bacteria.

Example 13—Base Editing of β-Lactamase on the *E. coli* Genome after Phagemid Transduction in OligoMM Mice In Vivo Using a Non-Replicative Payload Based on a Primase-Helicase This example presents a method for the adenine base editing (ABE8e-primase, SEQ ID NO: 2) of a target gene (e.g. β-lactamase; SEQ ID NO: 6) after packaged phagemid transduction in vivo into *E. coli* in an mouse colonization model. The packaged phagemids titer for the in vivo experiment was 1.5×10$^{10}$ transduction units per µl (tu/µl) after purification.

Figure 14:
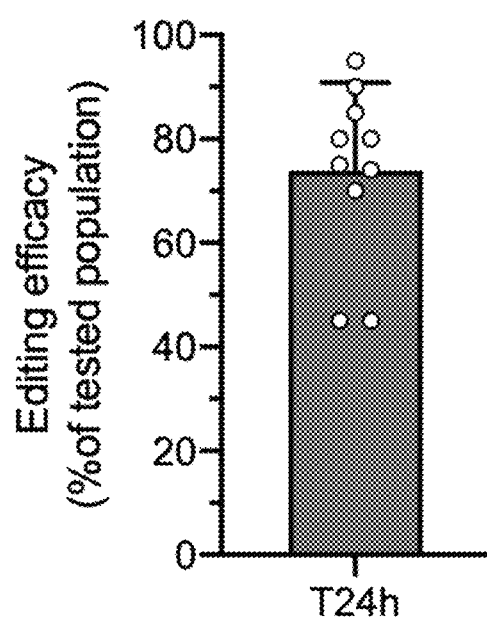
FIG. 14 displays histograms showing adenine base editing of β-lactamase after packaged phagemid transduction into $E.$ $coli$ in ten oligoMM mice using a non-replicative payload based on a primase-helicase. Delivery and editing efficiency of adenine base editing in vivo. The packaged phagemid titer for the in vivo experiment was $1.5*10^{10}$ to/μl. Stool samples were analysed 24 h post transduction. Cells were plated on streptomycin and streptomycin/carbenicillin in order to analyse editing efficiency (20 colonies per mouse). Editing of the active site of β-lactamase (K71) resulted in a loss of cell growth on carbenicillin plates. After 24 hours, base editing efficacy was ~75% of the whole population on average.

An *E. coli* strain carrying the β-lactamase gene in the genome was orally administered to 10 female mice aged 7 weeks at 10$^7$ CFU per mouse. A packaged phagemids dose of 1.5×10$^{12}$ to (ie 100 µl, buffered with 100 µl of sucrose bicarbonate) was orally administered to the mice (T0). Stool samples were collected immediately before this administration, as well as 24 hours after (T24h). Stool homogenates were plated on selective medium, and individual clones were further repatched on agar plates with or without carbenicillin in order to analyse editing efficiency (20 colonies per mouse and per time point). Editing of the active site of β-lactamase (K71E) resulted in a loss of bacterial growth on carbenicillin plates. At T24 h, ~75% of the whole population was base-edited on average (see FIG. 14).

Example 14—Prime Editing of β-Lactamase on the *E. coli* Genome after Phagemid Transduction In Vitro This example presents a method for the prime editing of the nucleic acid sequence encoding the Red Fluorescent Protein RFP (SEQ ID NO: 2314) on the *E. coli* genome after transduction with a DNA payload. The payload (SEQ ID NO: 2325) encodes a prime editor (PE), a transcribed prime editing guide RNA (pegRNA) under the inducible promoter pBetI, a lambda packaging sequence, a chloramphenicol resistance marker, and a p15A origin of replication. The pegRNA consists of an extended single guide RNA containing a primer binding site and a reverse transcriptase sequence in order to replace RFP's amino acid E16 (GAA) with a stop codon (TAA) on the bacterial genome.

The prime editor was engineered to insert a stop codon at position E16 of the target gene RFP resulting in a loss of red fluorescence.

Production of packaged phagemids comprising an A8 gpJ protein and a p2 STF protein for delivery into *E. coli* MG1655, resulted in titers of 2.6×10$^7$ transduction units per µl (tu/µl).

The fluorescence of colonies was analyzed by flow cytometry after overnight selection on chloramphenicol and 10 mM choline chloride and repatching on chloramphenicol plates. The genomic RFP was amplified from non-fluorescent colonies and the resulting PCR fragments were sequenced and the editing efficiency calculated. The stop codon was present in one of these individual colonies confirming successful prime editing after phagemid transduction.

Example 15—Editing of *E. faecalis, E. faecium* and/or *L. brevis* Expressing Tyrosine Decarboxylase for Preventing L-DOPA Inactivation when Treating Subjects Suffering from Parkinson's Disease In recent years, it was shown that the microbial decarboxylases that are part of gut microbial organisms appear to be able to metabolise L-DOPA (levodopa). Novel bacterial L-DOPA metabolism by tyrosine decarboxylases (tyrDCs) has been identified, dominantly driven by *Enterococcus faecalis* (Maini Rekdal et al. Science 2019; 364) but also *E. faecium* and *L. brevis*. Mutating these tyrDCs in *E. faecalis, E. faecium* and/or *L. brevis* can block this bacterial L-DOPA-to-dopamine metabolism, thereby improving drug efficacy.

A method to prevent the expression of a functional tyrosine decarboxylase of *Enterococcus faecalis, E. faecium* and/or *L. brevis* by in situ genetic modification of the gene sequence encoding said tyrosine decarboxylase is described below.

A phagemid is generated containing a phage packaging site, a base editor enzyme containing a dCas9 or nCas9 fused to a deaminase domain for inducing genetic modifications or a prime editor enzyme containing a dCas9 or nCas9 fused to a reverse transcriptase domain for inducing genetic modifications, and a transcribed guideRNA targeting the catalytic site of tyrosine decarboxylase. The guideRNA is designed to introduce a stop codon in the catalytic site of said enzyme, rendering it inactive.

Packaged phagemids are produced following a standard thermal induction protocol[26].

The phagemid contacts the bacterial population resulting in at least one mutation resulting a stop codon in the catalytic site of tyrosine decarboxylase.

Treating patients suffering from Parkison's disease with L-DOPA in combination with such packaged phagemids leads to a better efficacy of L-DOPA.

Example 16—Editing of *Clostridium sporogenes* Expressing DHPAA Synthase for Preventing L-DOPA Deamination when Treating Subjects Suffering from Parkinson's Disease Levodopa is absorbed in the small intestine, however, 9-10% of unabsorbed "residual" L-dopamine is metabolised further down in the gut (this percentage increases with age and administered drug dose). The metabolite that results from this reaction—DHPPA—affects gut motility and constipation. This deamination can be mediated by *Clostridium sporogenes* which expresses DHPAA synthase. Constipation is a known side effect of Levodopa and inhibitors of this deamination could be beneficial.

A method to prevent the expression of a functional DHPAA synthase of *C. sporogenes* by in situ genetic modification of the gene sequence encoding said DHPAA synthase is described below.

A phagemid is generated containing a phage packaging site, a base editor enzyme containing a dCas9 or nCas9 fused to a deaminase domain for inducing genetic modifications or a prime editor enzyme containing a dCas9 or nCas9 fused to a reverse transcriptase domain for inducing genetic modifications, and a transcribed guideRNA targeting the catalytic site of DHPAA synthase The guideRNA is designed to introduce a stop codon in the catalytic site of said enzyme, rendering it inactive.

Packaged phagemids are produced following a standard thermal induction protocol[26].

The phagemid contacts the bacterial population resulting in at least one mutation resulting in a stop codon in the catalytic site DHPAA synthase.

Treating patients suffering from Parkison's disease with L-DOPA in combination with such packaged phagemids leads to reduced side effects, in particular reduced constipation.

Lengthy table referenced here

US11534467-20221227-T00001

Please refer to the end of the specification for access instructions.

Lengthy table referenced here

US11534467-20221227-T00002

Please refer to the end of the specification for access instructions.

REFERENCES

1. Massip, C. et al. Deciphering the interplay between the genotoxic and probiotic activities of *Escherichia coli* Nissle 1917. Plos Pathog 15, e1008029 (2019).
2. Gil-Cruz, C. et al. Microbiota-derived peptide mimics drive lethal inflammatory cardiomyopathy. Science 366, 881-886 (2019).
3. Dreux, N. et al. Point Mutations in FimH Adhesin of Crohn's Disease-Associated Adherent-Invasive *Escherichia coli* Enhance Intestinal Inflammatory Response. Plos Pathog 9, e1003141 (2013).
4. Zou, D. et al. A SNP of bacterial blc disturbs gut lysophospholipid homeostasis and induces inflammation through epithelial barrier disruption. Ebiomedicine 52, 102652 (2020).
5. Tomida, S. et al. Pan-Genome and Comparative Genome Analyses of *Propionibacterium acnes* Reveal Its Genomic Diversity in the Healthy and Diseased Human Skin Microbiome. *mBio* 4, e00003-13 (2013).
6. Negi, S., Singh, H. & Mukhopadhyay, A. Gut bacterial peptides with autoimmunity potential as environmental trigger for late onset complex diseases: In—silico study. Plos One 12, e0180518 (2017).
7. Greiling, T. M. et al. Commensal orthologs of the human autoantigen Ro60 as triggers of autoimmunity in lupus. *Sci Transl Med* 10, eaan2306 (2018).
8. Garcia, A. R. et al. Peripheral tolerance to insulin is encoded by mimicry in the microbiome. *Biorxiv* 2019.12.18.881433 (2019) doi:10.1101/2019.12.18.881433.
9. Rees, H. A. & Liu, D. R. Base editing: precision chemistry on the genome and transcriptome of living cells. *Nat Rev Genet* 19, 770-788 (2018).
10. Anzalone, A. V. et al. Search-and-replace genome editing without double-strand breaks or donor DNA. *Nature* 576, 149-157 (2019).
11. Sharon, E. et al. Functional Genetic Variants Revealed by Massively Parallel Precise Genome Editing. *Cell* 175, 544-557.e16 (2018).
12. Farzadfard, F. & Lu, T. K. Genomically encoded analog memory with precise in vivo DNA writing in living cell populations. Science 346, 1256272 (2014).
13. Wannier, T. M. et al. Improved bacterial recombineering by parallelized protein discovery. Bionciv 2020.01.14.906594 (2020) doi:10.1101/2020.01.14.906594.
14. Karberg, M. et al. Group II introns as controllable gene targeting vectors for genetic manipulation of bacteria. *Nat Biotechnol* 19, 1162-7 (2001).
15. Simon, A. J., Ellington, A. D. & Finkelstein, I. J. Retrons and their applications in genome engineering. *Nucleic Acids Res* 47, 11007-11019 (2019).
16. Jinek, M. et al. A programmable dual-RNA-guided DNA endonuclease in adaptive bacterial immunity. *Sci New York N Y* 337, 816-21 (2012).
17. Cox, D. B. T. et al. RNA editing with CRISPR-Cas13. Science 358, 1019-1027 (2017).
18. Koonin, E. V., Makarova, K. S. & Zhang, F. Diversity, classification and evolution of CRISPR-Cas systems. *Current Opinion in Microbiology* 37, 67-78 (2017).
19. Makarova, K. S. et al. Evolutionary classification of CRISPR-Cas systems: a burst of class 2 and derived variants. *Nat Rev Microbiol* 18, 67-83 (2020).
20. Fonfara, I. et al. Phylogeny of Cas9 determines functional exchangeability of dual-RNA and Cas9 among orthologous type II CRISPR-Cas systems. *Nucleic Acids Research* 42, 2577-2590 (2014).
21. Abudayyeh, O. O. et al. RNA targeting with CRISPR-Cas13. Nature 550, 280 (2017).
22. Costa, T. R. D. et al. Secretion systems in Gram-negative bacteria: structural and mechanistic insights. *Nat Rev Microbiol* 13, 343-359 (2015).
23. Anné, J., Economou, A. & Bernaerts, K. Protein and Sugar Export and Assembly in Gram-positive Bacteria. 267-308 (2016) doi:10.1007/82_2016_49.
24. Camprubí-Font, C., Ewers, C., Lopez-Siles, M. & Martinez-Medina, M. Genetic and Phenotypic Features to Screen for Putative Adherent-Invasive *Escherichia coli*. *Front Microbiol* 10, 108 (2019).
25. Camprubí-Font, C., Castillo, B. R. D., Barrabés, S., Martínez-Martínez, L. & Martinez-Medina, M. Amino Acid Substitutions and Differential Gene Expression of Outer Membrane Proteins in Adherent-Invasive *Escherichia coli*. Front Microbiol 10, 1707 (2019).
26. Wang, I.-N. Lysis Timing and Bacteriophage Fitness. Genetics 172, 17-26 (2005).
27. Méric, G. et al. Disease-associated genotypes of the commensal skin bacterium *Staphylococcus epidermidis*. Nat Commun 9, 5034 (2018).
28. Ruff, W. E. et al. Pathogenic Autoreactive T and B Cells Cross-React with Mimotopes Expressed by a Common Human Gut Commensal to Trigger Autoimmunity. Cell Host Microbe 26, 100-113.e8 (2019).
29. Chen, L et al. Precise and programmable C:G to G:C base editing in genomic DNA. Biorxiv (2020).
30. Kurt, I et al. CRISPR C-to-G base editors for inducing targeted DNA transversions in human cells. Nature Biotechnology (2020).
31. Zhao, D et al. New base editors change C to A in bacteria and C to G in mammalian cells. Nature Biotechnology (2020).

32. Komor, A et al. Programmable editing of a target base in genomic DNA without double-stranded DNA cleavage. Nature 533:420-4. (2016).
33. Gaudelli, N. M. et al. Programmable base editing of A·T to G·C in genomic DNA without DNA cleavage. Nature 551(7681) 464-471 (2017).
34. Liu, D et al. A:T to C:G base editors and uses thereof. Patent application WO2020181180 (2020).
35. Liu, D et al. A:T to T:A base editing through adenine deamination and oxidation. Patent application WO2020181202 (2020).
36. Liu, D et al. T:A TO A:T base editing through adenosine methylation. Patent application WO2020181193 (2020).
37. Liu, D et al. T:A TO A:T base editing through thymine alkylation. Patent application WO2020181178 (2020).
38. Liu, D et al. T:A TO A:T base editing through adenine excision. Patent application WO2020181195 (2020).
39. Grunewald, J et al. A dual-deaminase CRISPR base editor enables concurrent adenine and cytosine editing, Nature Biotechnology (2020).
40. Li, C et al. Targeted, random mutagenesis of plant genes with dual cytosine and adenine base editors, Nature Biotechnology (2020).
41. Chen et al. Programmable C:G to G:C genome editing with CRISPR-Cas9-directed base excision repair proteins. Nature Communications 12:1384 (2021)

LENGTHY TABLES

The patent contains a lengthy table section. A copy of the table is available in electronic form from the USPTO web site (https://seqdata.uspto.gov/?pageRequest=docDetail&DocID=US11534467B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11534467B2). An electronic copy of the "Sequence Listing" will also be available from the USPTO upon request and payment of the fee set forth in 37 CFR 1.19(b)(3).

We claim:

1. A method of modifying a naturally occurring bacteria in situ in a subject comprising:
    administering to the subject a vector in a delivery vehicle, wherein the vector encodes a gene editing enzyme or system targeting a specific nucleotide sequence in the bacteria;
    genetically modifying a DNA sequence to generate at least one change in the targeted nucleotide sequence in the naturally occurring bacteria in situ without introducing a double strand break in the DNA sequence,
    wherein said genetic modification does not lead to the death of bacteria.
2. The method of claim 1, wherein said vector is a phagemid.
3. The method of claim 1, wherein the vector is a packaged phagemid.
4. The method of claim 3, wherein the phagemid comprises a nucleic acid sequence encoding a dCas9 (dead-Cas9).
5. The method of claim 3, wherein the phagemid comprises a nucleic acid sequence encoding an nCas9 (nickase Cas9).
6. The method of claim 4, wherein the phagemid comprises a nucleic acid sequence encoding a fusion protein of the dCas9 and a deaminase domain.
7. The method of claim 5, wherein the phagemid comprises a nucleic acid sequence encoding a fusion protein of the nCas9 and a deaminase domain.
8. The method of claim 1, wherein the vector further comprises a conditional origin of replication which is inactive in the targeted naturally occurring bacteria.
9. The method of claim 1, wherein the gene editing enzyme further comprises one or two uracil DNA glycosylase inhibitor domain(s) (UGI).
10. The method of claim 1, wherein the gene editing enzyme further comprises Mu-GAM.
11. The method of claim 1, wherein the gene editing enzyme is a dual base editor.
12. The method of claim 1, wherein the gene editing enzyme further comprises a reverse transcriptase domain.
13. The method of claim 1, wherein the gene editing enzyme further comprises an inhibitor of base repair.
14. The method of claim 1, wherein the gene editing system is a retron based system.
15. The method of claim 1, wherein said genetic modification is a point mutation.
16. The method of claim 1, wherein said genetic modification is a point mutation leading to gene disruption.
17. The method of claim 1, wherein the genetic modification is in a bacterial toxin gene.
18. The method of claim 1, wherein the vector generates a genetic modification in a DNA sequence coding for an immunogenic component expressed or secreted by the bacteria.
19. The method of claim 1, wherein the genetic modification is a point mutation that results in a change of an amino acid in a mimic peptide, wherein said mimic peptide is a bacterial antigen that mimics a human protein.
20. The method of claim 1, wherein the bacteria with the genetic modification does not have a reduced in vivo growth rate as compared to the same bacteria without the genetic modification.

21. The method of claim 1, wherein said naturally occurring bacteria is involved in a microbiome associated disorder or disease.

22. The method of claim 1, wherein the naturally occurring bacteria is *Bacteroides faecis* or *Bacteroides thetaiotaomicron* and the genetic modification is in the *Bacteroides faecis* or *Bacteroides thetaiotaomicron* beta-galactosidase gene.

23. The method of claim 22, wherein the genetic modification in the beta-galactosidase gene results in a change in the amino acid sequence of the beta-galactosidase protein and results in lower identity with human MYH6 cardiac peptide (SEQ ID NO: 2324) as compared to the *Bacteroides faecis* or *Bacteroides thetaiotaomicron* beta-galactosidase protein without the genetic modification, wherein the changed amino acid corresponds to Leu9, Leu11, Met12, Ala13, Leu15, Thr18, Ala20, Ser21, and Ala22 of SEQ ID NO: 2322.

\* \* \* \* \*